(12) United States Patent
Chen

(10) Patent No.: US 8,785,505 B2
(45) Date of Patent: Jul. 22, 2014

(54) TOXICOLOGY AND CELLULAR EFFECT OF MANUFACTURED NANOMATERIALS

(75) Inventor: Fanqing Chen, Moraga, CA (US)

(73) Assignee: The Regents of the University of California, Oakland, CA (US)

(*) Notice: Subject to any disclaimer, the term of this patent is extended or adjusted under 35 U.S.C. 154(b) by 875 days.

(21) Appl. No.: 12/111,026

(22) Filed: Apr. 28, 2008

(65) Prior Publication Data

US 2009/0269279 A1  Oct. 29, 2009
US 2012/0315218 A9  Dec. 13, 2012

Related U.S. Application Data

(63) Continuation of application No. PCT/US2006/060369, filed on Oct. 30, 2006.

(60) Provisional application No. 60/731,557, filed on Oct. 28, 2005, provisional application No. 60/792,171, filed on Apr. 12, 2006.

(51) Int. Cl.
*A61K 31/015* (2006.01)

(52) U.S. Cl.
USPC .............................. 514/766; 977/738; 977/773

(58) Field of Classification Search
None
See application file for complete search history.

(56) References Cited

PUBLICATIONS

Jin et al. "Toxicity of Luminescent Silica Nanoparticles to Living Cells" Chemical Research Toxicology 20 (8):1126-1133 (2007).
Ding et al. "Molecular Characterization of the Cytotoxic Mechanism of Multiwall Carbon Nanotubes and Nano-Onions on Human Skin Fibroblast" Nano Letters 5(12):2448-2646 (2005).
Silva et al. "The Rat Ear Vein Model for Investigating In Vivo Thrombogenicity of Ultrafine Particles (UFP)" Toxicological Sciences 85: 983-989 (2005).
Sayes et al. "The Differential Cytotoxicity of Water-Soluble Fullerenes" Nano Letters 4:1881-1887 (2004).
Yinghuai et al. "Substituted Carborane-Appended Water-Soluble Single-Wall Carbon Nanotubes: New Approach to Boron Neutron Capture Therapy Drug Delivery" Journal of the American Chemical Society 127:9875-9880 (2005).
Burlaka et al. "Catalytic System of the Reactive Oxygen Species on the C60 Fullerene Basis" Experimental Oncology 26:326-327 (2004).
Shi Kam et al. "Carbon nanotubes as multifunctional biological transporters and near-infrared agents for selective cancer cell destruction" Proceedings of the National Academy of Sciences of the United States of America 102:11600-11605(2005).
Nelson et al. "Effects of acute and subchronic exposure of topically applied fullerene extracts on the mouse skin" Toxicology and Industrial health 9:623-630(1993).
Jia et al. "Cytotoxicity of Carbon Nanomaterials: Single-Wall Nanotube, Multi-Wall Nanotube, and Fullerene" Environmental Science and Technology 39:1378-1383(2005).
Goodman et al. "Toxicity of Gold Nanoparticles Functionalized with Cationic and Anionic Side Chains" Bioconjugate Chemistry 15:897-900(2004).
Lockman et al. "Nanoparticle surface charges alter blood-brain barrier integrity and permeability" Journal of Drug Targeting 12:635-641(2004).
Kirchner et al. "Cytotoxicity of Colloidal CdSe and CdSe/ZnS Nanoparticles" Nano Letters 5:331-338(2005).
Cunningham et al. "Investigating the toxicity of nanoscale materials by gene expression profiling: A systems biology approach" American Chemical Society Annual Meeting Presentation (2005). (Applicants and The American Chemical Society were unable to locate written reference materials by Cunningham et al. from any of the 2005 meetings so no reference materials have been submitted in this information Disclosure Statement.).
International Search Report for Application No. PCT/US06/60369 "Toxicology and Cellular Effect of Manufactured Nanomaterials" (2008).

*Primary Examiner* — James D Anderson
(74) *Attorney, Agent, or Firm* — Michelle Chew Wong; Lawrence Berkeley; National Laboratory

(57) ABSTRACT

The increasing use of nanotechnology in consumer products and medical applications underlies the importance of understanding its potential toxic effects to people and the environment. Herein are described methods and assays to predict and evaluate the cellular effects of nanomaterial exposure. Exposing cells to nanomaterials at cytotoxic doses induces cell cycle arrest and increases apoptosis/necrosis, activates genes involved in cellular transport, metabolism, cell cycle regulation, and stress response. Certain nanomaterials induce genes indicative of a strong immune and inflammatory response within skin fibroblasts. Furthermore, the described multiwall carbon nanoonions (MWCNOs) can be used as a therapeutic in the treatment of cancer due to its cytotoxicity.

8 Claims, 21 Drawing Sheets

Fig. 2
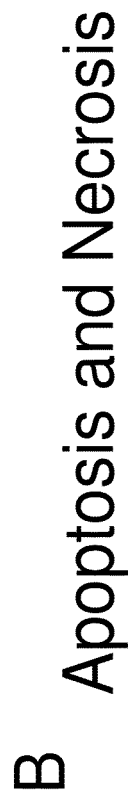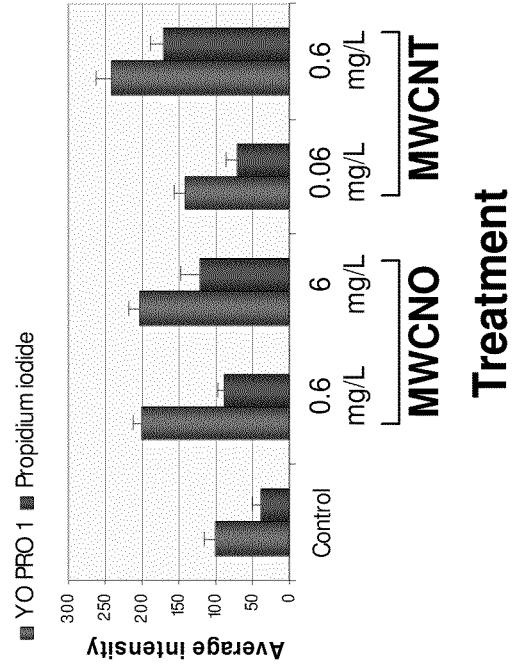
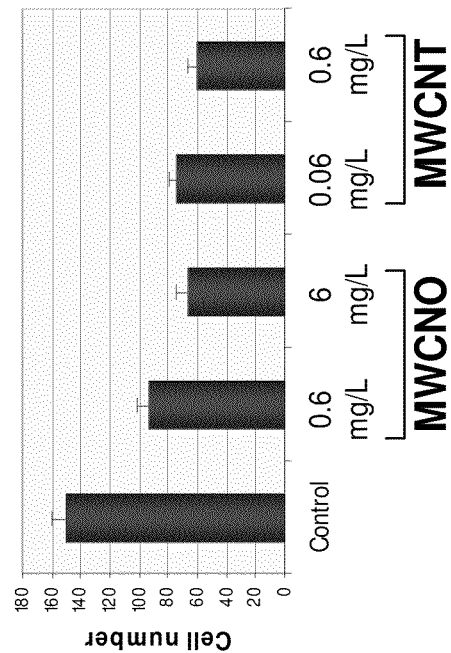

A. Response to carbon tube treatment

B. Response to carbon onion treatment

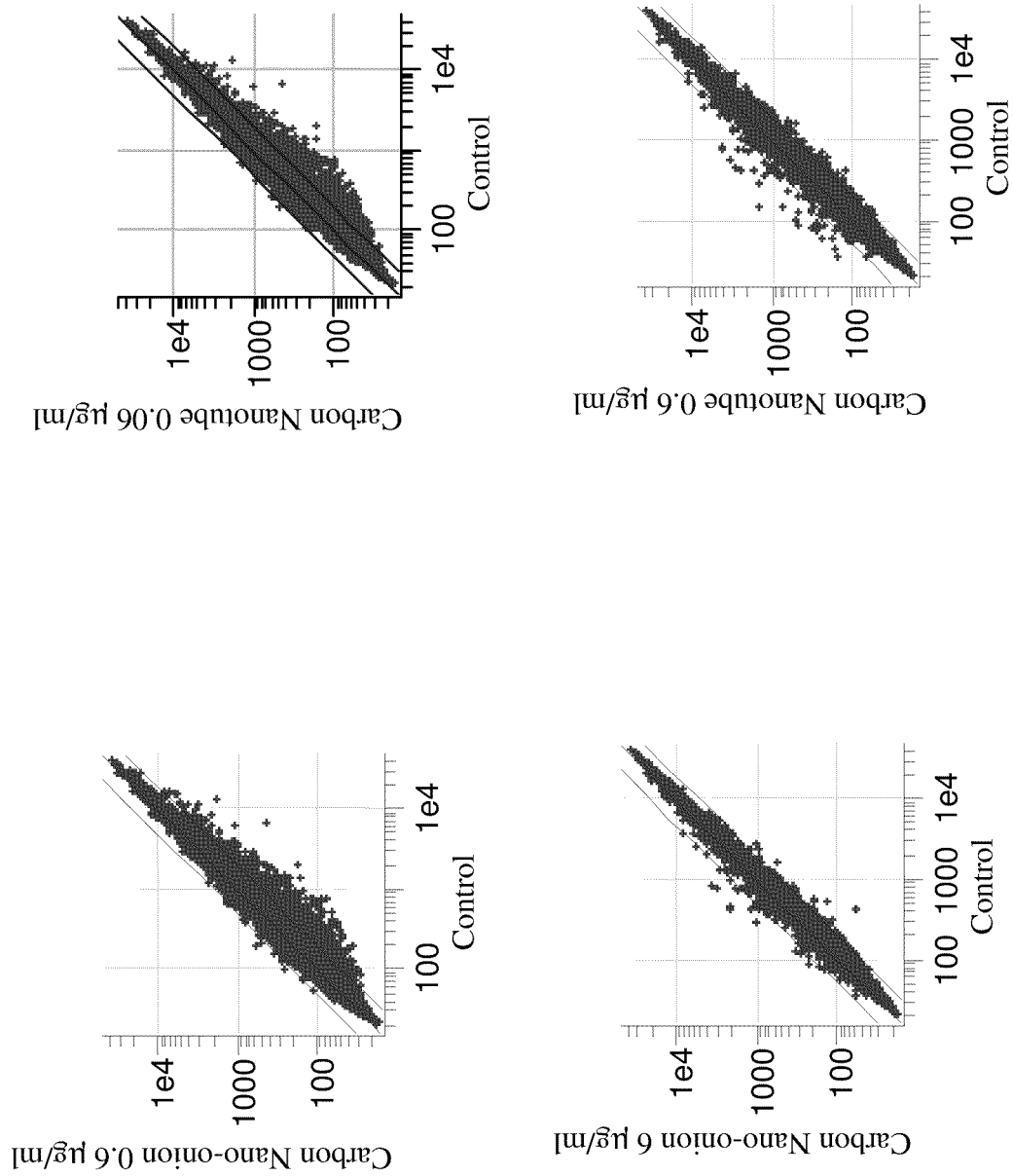

Fig. 10
I
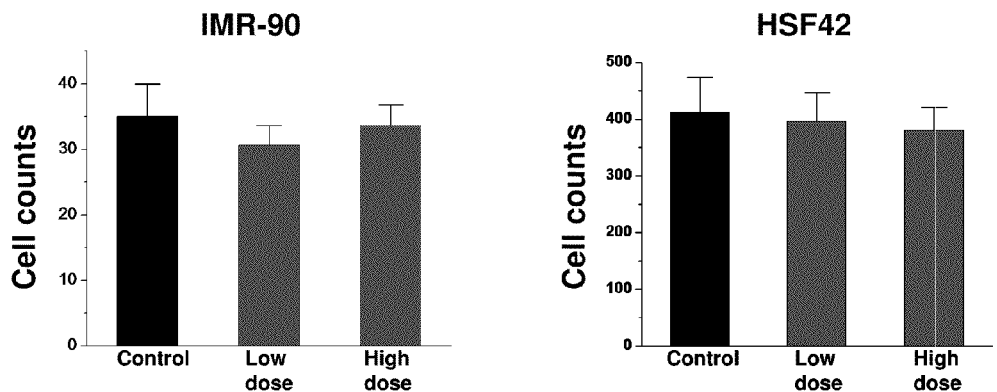
II
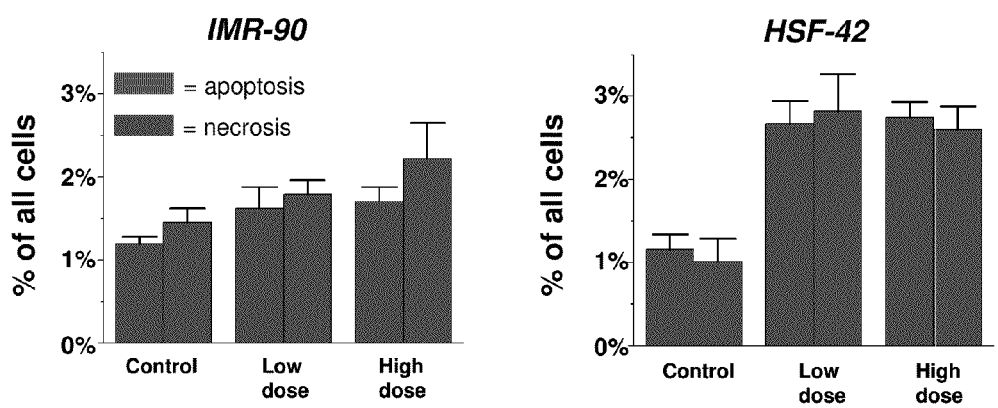
III
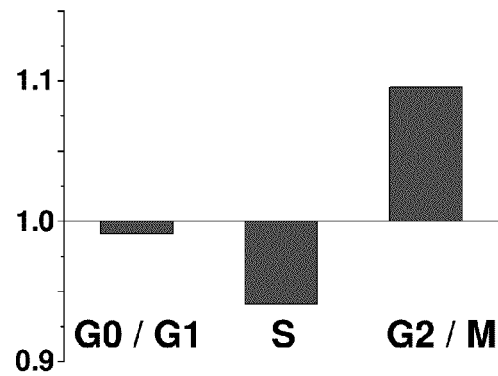

Fig. 12
8nM
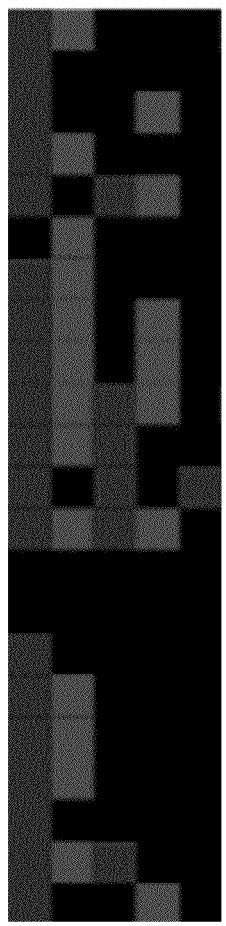
NKX2-5
COMP1
PAX6
DEC
STAT5A
CORIN
KISS1
BHLHB2
SERPINB7
BUB1
SLC4A4
BMO39
PLK1
CCNA2
CDC20
KIF4A
CDCA3
NEK2
KIF2C
HCAP-G
FOCM1
TACC3
ITGA6
POSTN
TK1
DDA3
DDA3
80nM
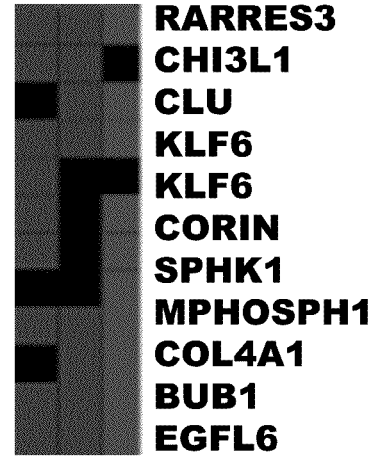
CDC5
FOXO3
FOX
RARRES3
CHI3L1
CLU
KLF6
KLF6
CORIN
SPHK1
MPHOSPH1
COL4A1
BUB1
EGFL6

-different surface charge
"+ "/ "neutral" /" – "

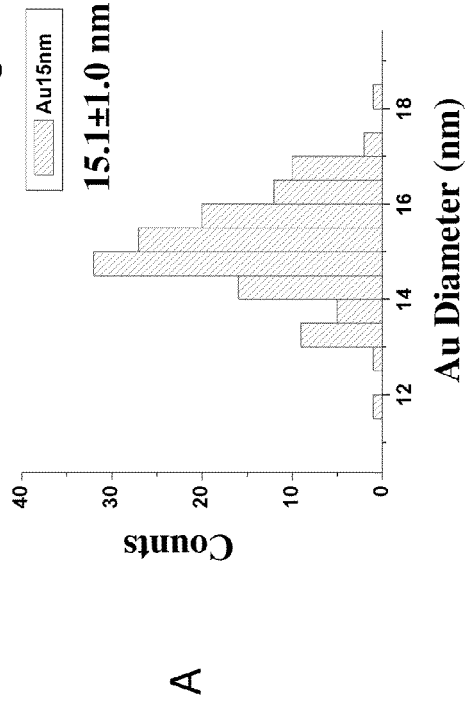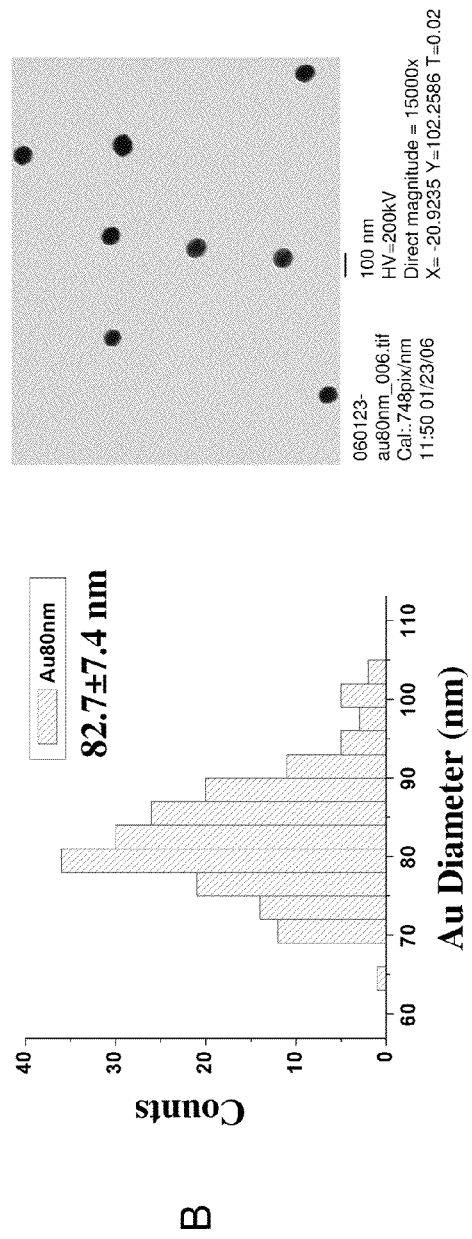
Fig. 18

TOXICOLOGY AND CELLULAR EFFECT OF MANUFACTURED NANOMATERIALS

CROSS-REFERENCE TO RELATED APPLICATION

This application claims priority to and is a continuation application of International Application No. PCT/US06/60369 filed on Oct. 30, 2006, which claims priority to U.S. Provisional Patent Application No. 60/731,557, filed on Oct. 28, 2005, and U.S. Provisional Patent Application No. 60/792,171, filed on Apr. 12, 2006.

STATEMENT OF GOVERNMENTAL SUPPORT

This invention was made during work supported by NIH Grant R1CA95393-01, DOD BCRP BC045345 Grant, DARPA, UCSF Prostate Cancer SPORE award (NIH Grant P50 CA89520), by a DOE LDRD grant, and by NIH P50 Grant CA112970. This work was performed under the auspices of the U.S. Department of Energy, at the University of California/Lawrence Livermore National Laboratory under Contract No. W-7405-Eng-48, and University of California/Lawrence Berkeley National Laboratory, under Contract No. DE-AC03-76SF00098, now Contract No. DE-AC05-CH11231. The government has certain rights in this invention.

REFERENCE TO ATTACHED TABLES

This application hereby incorporates by reference the attached Tables 1-21.

BACKGROUND OF THE INVENTION

1. Field of the Invention

The present invention relates to carbon nanomaterials and their therapeutic and cytotoxic uses thereof. More specifically, the present invention relates to using multiwall carbon nanomaterials for the treatment of cancer and other diseases. The present invention also relates to carbon nanomaterials and methods for measuring their toxicity thereof.

2. Related Art

The emerging field of nanotechnology is part of a new industrial revolution being applied to a diverse array of consumer products and medical applications, ranging from cosmetics to electronics and to drug delivery vehicles. With this revolution, methods to reduce the potential toxic effects of nanoparticles in both the environment and for medical applications should be addressed. Defining any potential toxicity will aid the nanotechnology industry to minimize the environmental impact of nanomaterials, leading to reduced concern from the public and policymakers, and a more successful industry.

The increasing use of nanotechnology in consumer products and medical applications underlies the importance of understanding its potential toxic effects to people and the environment. Although both fullerene and carbon nanotubes have been demonstrated to accumulate to cytotoxic levels within organs of various animal models and cell types, and carbon nanomaterials have been exploited for cancer therapies, the molecular and cellular mechanisms for cytotoxicity of this class of nanomaterial are not yet fully apparent.

Material that does not manifest toxic or carcinogenic characteristics in regular forms may have altered physical/chemical properties due to the quantum effect when their feature sizes fall in the 1-100 nm range that define them as nanomaterials. The transport and persistence of nanomaterials in the environment might be drastically different from the bulk material that we are familiar with, and new biological mechanisms for interaction, uptake and metabolism of nanomaterials have begun to emerge in the last few years. The unique properties of the nanomaterials include the increased surface/mass ratio, different shapes with size scale at the same range as biomolecules, altered mechanical and electromagnetic properties. It is critical to identify potential toxic/carcinogenic features of manufactured nanomaterial early in the process so that proper precautions can be taken before long term damages are done.

Carbon nano-materials, including carbon nanoparticles and nanotubes, have been one of the most extensively used nanoparticles, because of their unique and superior properties, including large surface areas, high electrical conductivity, and excellent strength. Multiwall carbon nanotubes (MWCNTs) and multiwall carbon nano-onions (MWCNOs), which will be the focus of this study, represent a relatively recently discovered allotrope of carbon derived from the more intensively studied fullerene ($C_{60}$). Single-walled, double-walled and multi-walled MWCNTs, with their diverse chemical and physical properties, have led them to be used in applications ranging from nanowires, electronic components, catalyst supports, electronic displays to drug delivery, and may even be used for hydrogen storage. Giant, nested fullerenes, generally called nano-onions (MWCNOs), comprise the least studied class of carbon nanoparticles. MWCNOs are usually produced by an underwater carbon-arc discharge. Although the applications of MWCNOs have lagged behind those of MWCNTs, they have been used as components of nanocomposites for applications including solar cells, light-emitting devices, and in fuel-cell electrodes.

The increase in commercial interest of nanomaterials and their subsequent production en masse, will lead to greater potential for exposure, to individuals. Fortunately, aerosol release of the MWCNOs and MWCNTs during manufacturing is limited. However, because of the increase in use, the risk associated with exposure and the molecular mechanisms of any cytotoxicity need to be well understood. Some of the primary questions that should be addressed include: i) likely routes and location of exposure, ii) molecular mechanisms of toxicity induced by exposure, iii) does observed toxicity correlate most to size, shape, or composition, iv) is there any concentration-dependent toxicity and v) are byproducts of production or decomposition toxic. The scientific community is beginning to address these concerns, but information is scant. To date, most toxicity studies have been performed, on ultrafine particles, which, interestingly, are more toxic than equivalent micron-sized material. See Silva, V. M., Corson, N., Elder, A. & Oberdorster, G. The Rat Ear Vein Model For Investigating In Vivo Thrombogenicity Of Ultrafine Particles (Ufp). *Toxicol Sci* (2005). Other studies, however, have demonstrated that toxicity is more highly correlated with particle composition and surface chemistry rather than size. See Sayes, C. M. et al. The differential cytotoxicity of water-soluble fullerenes. *Nano Letters* 4, 1881-1887 (2004).

Recently, single-walled carbon nanotubes (SWCNT) have been demonstrated to be an effective infrared photosensitizer for cancer cells (Shi Kam, N. W., O'Connell, M., Wisdom, J. A. & Dai, H. Carbon nanotubes as multifunctional biological transporters and near-infrared agents for selective cancer cell destruction. *Proc Natl Acad Sci USA* 102, 11600-11605 (2005)), and $C_2B_{10}$ carborane cage-coated SWCNT has been constructed as the delivery vehicle for boron neutron capture therapy for cancer (Yinghuai, Z. et al. Substituted carborane-appended water-soluble single-wall carbon nanotubes: new approach to boron neutron capture therapy drug delivery. *J Am Chem Soc* 127, 9875-9880 (2005)). Fullerene has been suggested to be a promising carcinotoxic chemical (Sayes et al., *Nano Letters* 4, 1881-1887 (2004); and Burlaka, A. P. et al. Catalytic system of the reactive oxygen species on the C60 fullerene basis. *Exp Oncol* 26, 326-327 (2004)). Therefore, we speculated that multi-walled carbon nanomaterial such as MWCNO and MWCNT will be more effective cancer killing agent than the SWCNT and single-walled fullerene. It is even more important to decipher the cytotoxicity and molecular mechanism of the multi-walled carbon nanomaterials.

Early studies have indicated that a repeated subchronic topical dose of fullerenes on mouse skin for up to 24 weeks, after initiation with a polycyclic aromatic hydrocarbon, does not result in either benign or malignant skin tumors, in contrast to development of benign skin tumors when a phorbol ester control is used for promotion (Nelson, M. A. et al. Effects of acute and subchronic exposure of topically applied fullerene extracts on the mouse skin. *Toxicol Ind Health* 9, 623-630 (1993)). More recent studies have begun to indicate possible adverse effects from carbon nanomaterial exposure, including oxidative stress, accumulation in nasal cavities, lungs, and brains after inhalation, inflammation, and tissue damage and central nervous disorders.

Evidence thus far suggests that the key factors contributing to nanomaterial-related cytotoxicity are size/mass, shape, surface charge, and surface functionalization. The cytotoxicity with equal mass basis shows an order of: SWNTs>MWNT10>$C_{60}$ (Jia, G. et al. Cytotoxicity of Carbon Nanomaterials Single-Wall Nanotube, Multi-Wall Nanotube, and Fullerene. 39, 1378-1383 (2005)). Investigations with 2 nm gold nanoparticles in different cell types, tested by MTT, hemolysis, and bacterial viability assays, showed that surface charge was a key factor in inducing toxicity. This indicates that cationic nanoparticles are moderately toxic, and have an immediate toxic effect at the Blood Brain Barrier, whereas anionic particles are relatively nontoxic (Goodman, C. M., McCusker, C. D., Yilmaz, T. & Rotello, V. M. Toxicity of gold nanoparticles functionalized with cationic and anionic side chains. *Bioconjug Chem* 15, 897-900 (2004); and Lockman, P. R., Koziara, J. M., Mumper, R. J. & Allen, D. D. Nanoparticle surface charges alter blood-brain barrier integrity and permeability. *J Drug Target* 12, 635-641 (2004)). Different surface coating also has been shown to change the cytotoxicity profiles of quantum dots (CdSe nanocrystals) dramatically, and modifications may attenuate the toxicity (Kirchner, C. et al. Cytotoxicity of colloidal CdSe and CdSe/ ZnS nanoparticles. *Nano Letters* 5, 331-338 (2005)).

As the exact molecular mechanisms for the damages inflicted are still not fully understood, the urgency of a more thorough molecular characterization of nanomaterial toxicity is evident. Expression array analysis and phenotypic measurements of exposed cell populations may provide insight into the mechanisms responsible for adverse events observed in these models. For example, a recent preliminary unpublished investigation demonstrated gene expression changes associated with the toxicity of nanoscale materials (Cunningham, M. J., Magnuson, S. R., Falduto, M. T., Balzano, L. & Resasco, D. E. Investigating the toxicity of nanoscale materials by gene expression profiling: A systems biology approach. *American Chemical Society Annual Meeting Presentation* (2005), and thus the potential benefit for using microarray technology to perform high throughput characterization of nanomaterial toxigenomics.

SUMMARY OF THE INVENTION

It is postulated that there are size-specific, shape-specific, and surface-specific effects and effectors for particles at the quantum range (1-100 nm). These effects are different from the effects observed for micro-sized particulates, and these quantum properties unique to nanomaterial play important role in determine toxicity, with altered genomic, proteomic and cellomic profiles, altered mutagenesis and carcinogenesis potentials, and different cellular level transport mechanisms. The data and methods described herein will show the existence of these nanoscale effects and molecular effectors and instrumental in differentiating nanotoxicology from conventional toxicology.

Herein is provided application of a reliable and valid methodology for measuring toxicological hazards associated with exposure to nanomaterials. The strategy to achieve this employs using reliable in-vitro systems that will enable the determination of which aspects are best predictors of acute/ chronic adverse health effects from Nanoscale materials in vivo. In one aspect, the present invention is directed to biomarkers whose gene expression profiles are changes upon exposure to nanomaterials. The biomarkers are found in the biological pathways of inflammation, apoptosis, immune response, ubiquitination, cell proliferation, cell cycle regulation, cell differentiation, golgi vesicle transport, membrane fusion, secretory pathway, intracellular transport, nucleocytoplasmic transport, apoptosis, response to DNA damage, response to stress and stimuli.

Furthermore, the biomarkers described herein and in the Examples can be used to select and/or develop the suitable instruments and methods for measuring exposure to particles according to the health affects. An ideal instrument would be a biosensor or lab on a chip device that industry could use to batch test materials.

In one aspect, using the biomarkers identified that are associated with particular nanoparticles, it is possible to evaluate the cytotoxicity of various nanomaterials that are carbon-based (such as carbon nanotubes and spherical carbon nanoparticles) or semiconductor-based (such as semiconductor nanocrystals), or metal-based, using the biomarkers and biomarker temporal change patterns as predictors for other nanoparticles. It was found that particular biological pathways are activated or perturbed by nanoparticle, these pathways and the nanoparticle specific biomarkers are listed in tables in the publications, including apoptosis, inflammation, cellular transporter, ubiquitination, etc. The changes in these biomarkers can be used as indicators or predictors for nanotoxicity.

Another aspect of the invention is the sensitivity of the assay system on nanotoxicity, when microarray technology is used here. The invention here provides guidelines for the threshold of cytotoxicity and the correlation with gene expression profile changes. In a preferred embodiment, the threshold is defined as 1% of total genes are changed more than two-fold.

Nanomaterials such as quantum dots are well attenuated by the protective, polyethylene glycol, and the genes changed are less than 0.5% of total genes. This number can be used as a quantitative measurement on whether the protective coating is effective for any other nanoparticles, or nanomaterials. In the field of semiconductor nanocrystals alone, multiple surface chemistries are available for solubilizing the nanoparticle, yet most of them do not prevent the leaking of Cd heavy metal into the solution, killing the cells for biological applications. The microarray gene expression analysis provides are quantitative and comprehensive measurement matrix for determine the effectiveness of the protective coating. This quantitative measurement can be used for any other nanoparticles that might have toxicity against the cells, tissues, or organs.

The gene ontology classification methods used also are very powerful indicators for the primary effect of the nanoparticles/nanomaterials. For instance (Table 1), 2% percentage of genes in the Golgi body transport pathways are changed after treatment, with P value<0.0001. These markers identified can be used as indicators of the nanotoxicological effects of nanomaterials, and more specifically nanocrystals, multiwall carbon nano-onions (MWCNOs) and multiwall carbon nanotubes (MWCNTs).

In another aspect, the genes identified and similar gene profiles identified using similar assay systems can be used as guidelines for attenuating the toxic effects. The biomarker changes should be eliminated or weakened, with the elimination of the nanotoxicity. This can be used as a measurement on the efficiency of toxicity control.

Another related aspect of the present invention is directed to using the cytotoxicity of nanoonions, by attaching proper targeting mechanisms (such as antibodies, small molecules, or peptides) to the nanoonions, for delivery to cancer cells in a tumor to kill the cancer cells. The nanoonions can be coated by liposomes, which can be attached to other targeting mechanisms and allow specific delivery. The nano-onions can also be directly inject into solid tumor by intratumoral injection or catheter-directed injection, accumulate in the tumor and kill the tumor over a 1-2 week period by staying in the interstitial fluid within the tumor and taken up by the tumor.

Alternatively, since the carbon nanoonions absorbs infrared light preferentially, IR laser can be used to further enhance the killing of the cancer cells with nano-onion accumulated, by hyperthermal effects through absorption. Carbon nanoonion can also be doped with Gadolinium and serve as a MRI contrasting reagent. It can also be doped with radionuclides for use in PET imaging. In the imaging-enhance version of the nano-onions, it can be used as a tool for image-guided intervention of tumor.

The nanoonions can be used for intratumoral injection to kill cancer when conjugated to tumor-targeting molecules, such as monoclonal antibodies, peptides, folate, etc. The targeted nanoonion can be carried to tumor and kill the tumor cells.

In another aspect, the nanoonions can be used bound to or encapsulated in immunoliposomes.

Thus, the present invention provides for a composition for the treatment of cancer, comprising: a multiwall carbon nanomaterial conjugated to a tumor-targeting molecule and an imaging reagent. In a preferred embodiment, the multiwall carbon nanomaterial is a nanoonion having a diameter of 10 to 50 nm. The tumor-targeting molecule can be selected from the group consisting of monoclonal antibodies, oligonucleotides, peptides, and small molecules. In one embodiment, the tumor-targeting molecule is a monoclonal antibody that is specific for Erbβ2. In another embodiment, the tumor-targeting molecule is a small molecule selected from the group consisting of folate, a vitamin, and a drug. The imaging reagent can be selected from the group consisting of a radio-label, radionuclide, fluorescent probe and chemiluminescent probe.

In another embodiment, the composition further comprises an immunoliposome bound to or encapsulating the multiwall carbon nanomaterial.

The present invention also provides a method of treating cancer comprising delivering the multiwall carbon nanomaterial conjugated to a tumor-targeting molecule and an imaging reagent to a subject in an effective therapeutic amount. In a preferred embodiment, the effective therapeutic amount does not induce greater than 25% overexpression or underexpression of a gene following treatment.

BRIEF DESCRIPTION OF THE FIGURES

FIG. 8. Scatter plot of normalized GeneChip data. The average signal intensities of GeneChip probe sets from 3 replicate experiments were plotted. X-axis represents the signal intensity of ethanol control sample, Y-axis represents samples treated with Carbon nanoparticles at different doses. The line through the center of gene populations indicates exactly same intensities between Carbon and control samples, two lines flanking the center line indicates 2 folds differences between the two conditions. Genes that fall in the area outside the 2-fold difference lines have more than 2-fold gene expression changes.

FIG. 10. I. Cell counts for IMR-90 and HSF-42 cells after treatment with silanized semiconductor nanocrystals in various doses. When treated with PEG-silane-semiconductor nanocrystals, the survival rate of both cell lines is mostly unaffected. The statistically insignificant reduction in the cell number may be explained by a mild block of the G2/M phase (see FIG. 2.III). This contrasts with the marked effect that organic nanostructures (carbon nanotube and nano-onions) have on IMR-90 and HSF42 cells. II.a. There's no statistically significant change in apoptotic/necrotic profile for PEG-silane-Qdot-treated IMR-90 cells, with either high or low dosage of semiconductor nanocrystals. PEG-silanized semiconductor nanocrystals appears much less detrimental than organic nanostructures. II.b. Treating HSF42 cells with semiconductor nanocrystals cause a slight increase in apoptotic/necrotic cells for both dosages. III. The distribution of PEG-silane-Qdot treated HSF42 cells in different phase of cell cycle. The baseline of 1 is equivalent to the control distribution. There are slightly less PEG-silane-Qdot treated cells in S-phase and slightly more (~10% more) in M-phase than control cells.

FIG. 12. Analysis of Transcription Regulatory Elements (TREs) in the promoters of the altered genes. The TREs for different transcription factors on the promoter regions of the altered genes are analyzed for over/under-representation relative to all promoters in PAINT database. The relationship of TREs and input genes are represented as an image of the interaction matrix: the columns of the interaction matrix correspond to the enriched TREs and each row corresponds to a gene from the input list. Individual elements of the matrix are colored by the significance p-values: over-representation in the matrix is indicated in spot brightness. There is an enrichment of FOX transcription binding elements on the high dose responsive genes. In low dose responsive genes that are down regulated, there's enrichment of DEC/BHLHB2, and COMP1 (cooperates with myogenic protein 1).

FIG. 18 shows photographs of Au nanoparticles of different sizes. A. Top, 15 nm Au, scalebar=20 nm. B. Bottom, 80 nm Au, scalebar=100 nm. The left panel are graphs showing the size distribution of the Au nanoparticles.

BRIEF DESCRIPTION OF THE TABLES

Figure 1:
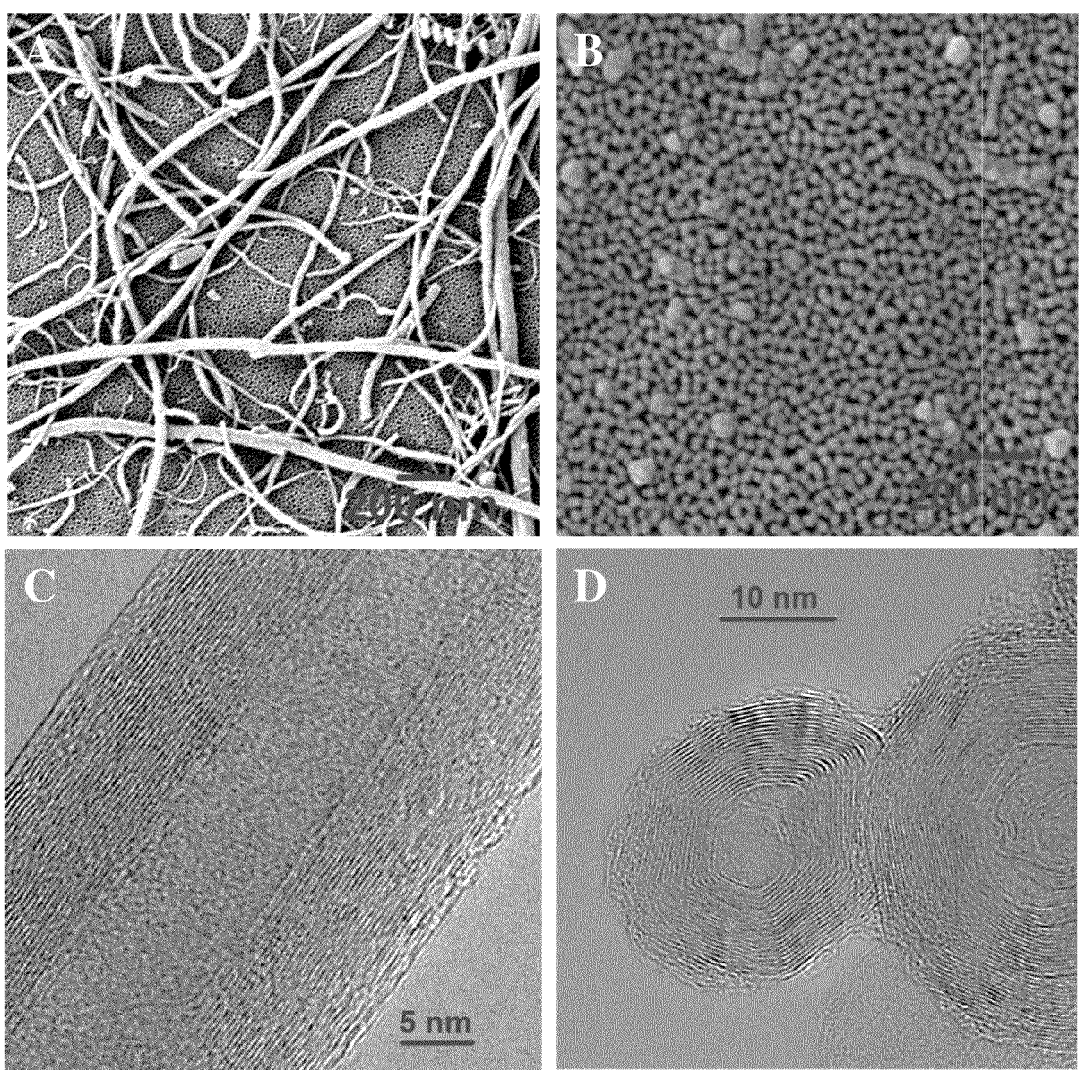
FIG. 1. Scanning electron microscopy (SEM) images and high resolution transmission electron microscopy (HRTEM) images of carbon nanomaterials used in this study. A. SEM image of multi-walled carbon nanotubes (scale bar=200 nm). B. SEM image of carbon nano-onions (scale bar=200 nm). C. HRTEM images of multi-walled carbon nanotubes (MWCNTs) (scale bar=5 nm). D. HRTEM images of multi-walled carbon nano-onions (MWCNO) (scale bar=10 nm).

Table 1.

Most significantly changed gene categories after treating HSF42 cells with carbon nanomaterials at cytotoxic doses. The categories are generated by GoMiner program (Materials and Methods, Supporting Information), using p-value as the evaluation criteria of statistically significant changes. For each category, p-value was calculated by conducting two-sided Fisher's exact test, which reflects the statistical significance for that category being enriched in changed genes. The p-values were used to sort categories to identify those gene functional groups that have responded the most after treatments.

Table 2.

Immune-response and inflammatory genes that over- or under-expressed after treating HSF42 cells with cytotoxic dose (0.6 μg/ml) of carbon MWCNTs. Fold changes represent the ratio of mRNA amount of treated samples divided by those of control samples.

Table 3.

Genes changed by nano-onion and nanotube but fall in the category of "transport" (Golgi vesicle transport, membrane fusion, secretory pathway, intracellular transport). Fold change of gene expression is given for the low dose (0.6 μg/mL for MWCNO and 0.06 μg/mL for MWCNT). Fold changes represent the ratio of mRNA amount of treated samples divided by those of control samples.

Table 4.

Genes changed by nano-onion and carbon nanotubes but fall in the category of cell cycle regulatory genes (G1/S transition of mitotic cell cycle, mitotic cell cycle, and cell growth of maintenance). Fold change of gene expression is given for the low dose (0.6 μg/mL for MWCNO and 0.06 μg/mL for MWCNT). Fold changes represent the ratio of mRNA amount of treated samples divided by those of control samples.

Table 5.

Genes changed by nano-onion and carbon nanotubes but fall in the category of apoptosis. Fold change of gene expression is given for the low dose (0.6 μg/mL for MWCNO and 0.06 μg/mL for MWCNT). Fold changes represent the ratio of mRNA amount of treated samples divided by those of control samples.

Table 6.

Genes changed by nano-onion and carbon nanotubes but fall in the category of external stimuli response genes. Fold change of gene expression is given for the low dose (0.6 μg/mL for MWCNO and 0.06 μg/mL for MWCNT). Fold changes represent the ratio of mRNA amount of treated samples divided by those of control samples.

Table 7.

The functional categories of the genes affected by low and high doses of PEG-silane-Semiconductor nanocrystals. All functional categories affected by high doses are also affected by a low dose treatment. A significant portion of the down-regulated genes are related to M-phase of mitotic cell cycle, especially the spindle assembly and cytokinesis. The up-regulated genes include those for carbohydrate binding proteins (possibly in recognition of the PEG coating of Semiconductor nanocrystals), intracellular organelle (especially vacuole and intracelluar vesicle) related proteins (possibly involved in intracellular transport of semiconductor nanocrystals), and stress-response genes (possibly due to the slight stress induced by treatment).

Table 8.

Significantly changed genes after treatment with PEG-silane-semiconductor nanocrystals. The genes presented in the table are the ones with fold change more than 2, and P value less than 0.05.

Table 9.

Top 20 genes in FIG. 4B Area I.

Table 10.

Genes in Area II of FIG. 4B. Common genes changed in both the high and low dose treatment with carbon nano-onions.

Table 11.

Top 20 genes in FIG. 4B Area III.

Table 12.

Top 20 genes in FIG. 4C Area I.

Table 13.

Genes in FIG. 4C, Area II.

Table 14.

Top 20 genes in FIG. 4C Area III.

Table 15.

Top 20 genes in FIG. 4D Area I.

Table 16.

Top 20 genes in FIG. 4D, Area II.

Table 17.

Top 20 genes in FIG. 4D Area III.

Table 18.

Top 20 genes in FIG. 4E Area I.

Table 19.

Top 20 genes in FIG. 4E Area II.

Table 20.

Top 20 genes in FIG. 4E Area III

Table 21.

Genes changed by the MWCNO but fall in the category of protein ubiquitination and ubiquitin cycle.

DETAILED DESCRIPTION OF THE PREFERRED EMBODIMENT

Carbon nano-materials, including carbon nanoparticles and nanotubes, have been one of the most extensively used nanoparticles, because of their unique and superior properties, including large surface areas, high electrical conductivity, and excellent strength. It is postulated that there are size-specific, shape-specific, and surface-specific effects and effectors for particles at the quantum range (1-100 nm). These effects are different from the effects observed for micro-sized particulates, and these quantum properties unique to nanomaterial play important role in determine toxicity, with altered genomic, proteomic and cellomic profiles, altered mutagenesis and carcinogenesis potentials, and different cellular level transport mechanisms.

Methods for Determining Toxicology of Carbon Nanomaterials

Toxicity of nanomaterials is a major healthcare concern that may impact the nanotechnology industry. Concern has been rising following studies on the toxicity of carbon nanophase materials, some of which are found in flames, welding fumes, diesel exhausts and other petrol byproducts (See Maynard, A. D., et al., *J Toxicol Environ Health A* 2004, 67, 87-107; Silva, V. M, et al., *Toxicol Sci* 2005; Frampton, M. W., et al., *Res Rep Health EffInst* 2004, 1-47; discussion 49-63; Block, M. L., et al., *Faseb J* 2004, 18, 1618-1620). There is evidence for the contribution of many factors to the toxicity of these organic nanostructures including their size, shape, and surface functionalization. Assuming an equivalent mass of carbon, cytotoxicity grows in the following order: fullerene ($C_{60}$)<multi-wall carbon nanotube (MWCNT) <single-wall carbon nanotube (SWCNT). (Jia, G., et al., 2005, 39, 1378-1383). For example, $C_{60}$, with a well-defined surface and no available dangling bonds, is harmful to cells even at low doses. (See Ali, S. S., et al., *Free Radic Biol Med* 2004, 37, 1191-1202; Oberdorster, E. *Environ Health Perspect* 2004, 112, 1058-1062). $C_{60}$ is an excellent electron acceptor that can readily react with available oxygen and water to generate free radicals leading to oxidative damage of the cellular membrane. Derivatized fullerenes are less efficient in producing oxygen radicals, therefore $C_{60}$ derivatized with hydroxyl groups is much less toxic. Less is known about the toxicity of fluorescent semiconductor nanocrystals (commercially sold as QUANTUM DOTS by Invitrogen). Semiconductor nanocrystals are CdSe/ZnS core/shell nanocrystals and the heavy elements that make up the core may induce a more pronounced and acute cytotoxic response than carbon nanostructures. It has been reported that $Cd^{2+}$ is released from CdSe through oxidative attack. (Tang, Z., et al., *Nano Letters* 2005, 17, 358-363; Zaitseva, N., et al., *Advanced Materials*

2005, 17, 1321-1324). This released cadmium can bind to the sulfhydryl groups of critical mitochondria proteins leading to mitochondria dysfunction and ultimately cell poisoning. (Rikans, L. E.; Yamano, T. *Journal of Biochemical and Molecular Toxicology* 2000, 14, 110-117).

Herein is provided an application of a reliable and valid methodology for measuring toxicological hazards associated with exposure to nanomaterials. The strategy to achieve this employs using reliable in-vitro systems that will enable the determination of which aspects are best predictors of acute/chronic adverse health effects from nanoscale materials in vivo. Furthermore, the present methods have established biomarkers whose gene expression profiles are changed in response to exposure to nanomaterials. The genes are found in the biological pathways of inflammation, apoptosis, immune response, ubiquitination, cell proliferation, cell cycle regulation, cell differentiation, golgi vesicle transport, membrane fusion, secretory pathway, intracellular transport, nucleocytoplasmic transport, apoptosis, response to DNA damage, response to stress and stimuli.

In a preferred embodiment, assays detecting toxicity, stress response and DNA damage as a result of nanomaterial exposure are examined in any cell type, preferably in human epithelial cells, normal human keratinocytes (NHK) and human fibroblasts (HSF). In a preferred embodiment, each assay is first calibrated against nanomaterial known to elicit toxic, stress and/or DNA damage responses. For instance, the examples show that MWCNT induces inflammatory response, and titanium dioxide induces DNA damage. The dose range for each of the nanomaterials tested by the assay is decided using cell proliferation, apoptosis/necrosis, cell cycle assays using the cytometry and Cellomics.

Nanomaterial Assessment.

In the present method, nanomaterials are assessed for toxicity and ability to elicit stress and/or DNA damage using calibrated materials as described herein. All analyses should be performed in triplicate for the three test cell types. Depending on composition, nanomaterials will be resuspended in water, ethanol or DMSO or any other appropriate solvent and sonicated for one hour prior to biological assessment. The exact assessment strategies will depend on the results of the calibration studies. However, the assays will be optimized to achieve maximum sensitivity to induced toxicity, stress and DNA damage. Surface chemistry will be an important parameter to be explored since published reports suggest this is one of the critical determinants in physiological impact (See Sayes, C. et al. The differential cytotoxicity of water-soluble fullerenes. *Nanoletters* 4, 1881-1997 (2004); Akiyoshi Hoshino, A. et al. Physicochemical Properties and Cellular Toxicity of Nanocrystal Quantum Dots Depend on Their Surface Modification. *Biochem Biophys Res Commun* 4, 2163-2169 (2004)).

Toxicity.

In another embodiment, the reverse phase protein array can be used (FIG. 15) as described by Shingyoji, M., Gerion, D., Pinkel, D., Gray, J. W. & Chen, F. Quantum Dots-based Reverse Phase Protein Microarray. *TALANTA* 67, 472-478 (2005), hereby incorporated by reference, to quantitate proteins in treated cells to determine toxicity. It may be preferred to use antibodies already tested for epithelial cancer cells in the NCI ICBP P50 program, to minimize efforts validating the assay.

In a preferred embodiment, one of the following approaches can be used to evaluate toxicity in nanomaterial exposed cells: (i) the measurement of phenotypic changes in large populations of cells by high content analysis and (ii) gene expression array analysis in exposed cells. For instance, it was found that carbon nanomaterials generated mRNA level changes in exposed skin fibroblasts, including changes in mRNA levels from genes involved in metabolism, apoptosis, cell cycle, stress response, cellular transport, and inflammatory response. Thus, in a preferred embodiment, toxicity is measured by profiling the transcription levels of genes, specifically those found in the Tables as potentially being most affected by exposure to nanomaterials. Genes that demonstrate expression level changes after nanomaterial treatment are placed into Gene Ontology categories using GOMiner, evaluated for statistical significance, and then sorted by significance (See Table 1 in Appendix for example).

Of interest was the observation that many of the genes that increased in expression in nanomaterial-exposed cells are often associated with a type I interferon response, which is known to be activated during viral infection and leads to antiviral and anti-proliferative responses. Promoter analysis, derived from gene expression data, indicates that the primary mechanism for cell effects from toxic carbon nanomaterials is through the p38/ERK MAPK kinase and interferon response pathways. Thus, in another preferred embodiment, at least the gene profile of transcription levels of genes in the MAPK kinase and interferon response pathways are measured to determine cellular effects and levels of toxicity of nanomaterials after cell exposure.

In one embodiment, transcription profiling is carried out using methods and systems known in the art. In a preferred embodiment, transcription profiling is carried out using Affymetrix U133A arrays in the High Throughput Array (HTA) system. The HTA that processes arrays in a standard 96 well microplate format. A Sciclone microfluidics platform (Caliper Life Sciences, Hopkinton, Mass.) integrated into this system performs standardized protocols for cRNA probe preparation, quantification and normalization; hybridization setup, and array washing and staining. A Zymark Twister (Caliper Life Sciences, Hopkinton, Mass.) arm moves plates (and tips) onto and off of the deck and into the thermal cycler for all temperature-dependent steps. An Axon scanner and ImageXpress 5000 (Molecular Devices, Sunnyvale, Calif.) console application, tightly integrated with this system, generates 25 GB of data from one plate of 96 human U133A of Av.2 arrays (Affymetrix, Santa Clara, Calif.) in approximately 8 hours. This new format automates the most labor-intensive steps resulting in much higher throughput (five fold increase) at a much reduced cost.

Using the biomarkers that are associated with particular nanoparticles as identified in the Tables, it is possible to evaluate the cytotoxicity of various nanomaterials that are carbon-based (such as carbon nanotubes and spherical carbon nanoparticles) or semiconductor-based (such as semiconductor nanocrystals), or metal oxide-based, or any nanomaterials made from any combination of these or derivative thereof, having any surface or other modification thereof. The nanomaterials to be evaluated can be in the size range of 1-100 nm. Surface modifications can include charge density alteration by introducing positively or negatively charged groups, encapsulation by polymers, lipids, inorganic thin films, biocompatible materials, and biomolecules including biopids, biominerals, polysaccharides, nucleic acids, dendrimers, aptamers, polypeptides, proteins, and nanocomposites which are a combination of two or more of the above variations.

The biomarkers and biomarker temporal change patterns herein described and further obtained can be used as predictors for other nanoparticles. It was found that particular biological pathways are activated or perturbed by nanoparticles, including apoptosis, inflammation, cellular transporter, ubiquitination, etc. These pathways and the nanoparticle specific biomarkers are listed in Tables 2-7 and 8-21 attached and incorporated by reference. Thus, the changes in these biomarkers can be used as indicators or predictors for nanotoxicity.

The invention provides for a method for identifying nanotoxicity of a nanomaterial, comprising: (a) measuring in a sample the expression level of at least one gene selected from Tables 2-7 and 8-21, wherein said sample contains cells exposed to said nanomaterial; and (b) comparing the expression level of said gene from the patient with the expression level of the gene in a normal tissue sample or a reference expression level (such as the average expression level of the gene in a cell line panel or a cancer cell or tumor panel, or the like), wherein a two-fold increase in the expression level or a decrease of expression of at least one gene selected from Tables 2-7 and 8-21 indicates toxicity of the nanomaterial.

In some embodiments of the invention, step (a) comprises measuring in a sample the expression level of at least two genes selected from the Tables 2-7 and 8-21. In further embodiments, the expression level of at least 3, 4, 5, 10, 15, 20, 30, 40, 50, 60, 75, 80, 90, or 100 genes selected from the Tables 2-7 and 8-21 are measured in a sample to determine the toxicity of a nanomaterial.

In one embodiment, the Tables and results herein described are used as guidelines for the threshold of cytotoxicity and the correlation with gene expression profile changes. For example, comparison between gene expression profiles of cell exposed to the nanomaterial being tested and the gene expression profile of semiconductor nanocrystals (Table 7-8) and multi-wall carbon nanotubes and multi-wall carbon nanoonions (Tables 1-6) can be used aid in the prediction of toxicity of a nanomaterial. In a preferred embodiment, the threshold is defined as 1% of total genes are changed more than two-fold. In other embodiments, the threshold may be defined by observing a percent change (e.g., 20% to 50% or more change) in gene expression in a predetermined set of genes.

Nanomaterials such as semiconductor nanocrystals are well attenuated by the protective, polyethylene glycol, and the genes changed are less than 0.5% of total genes. In one embodiment, this number can be used as a quantitative measurement on whether a protective coating is effective for any other nanoparticles, or nanomaterials.

Figure 15:
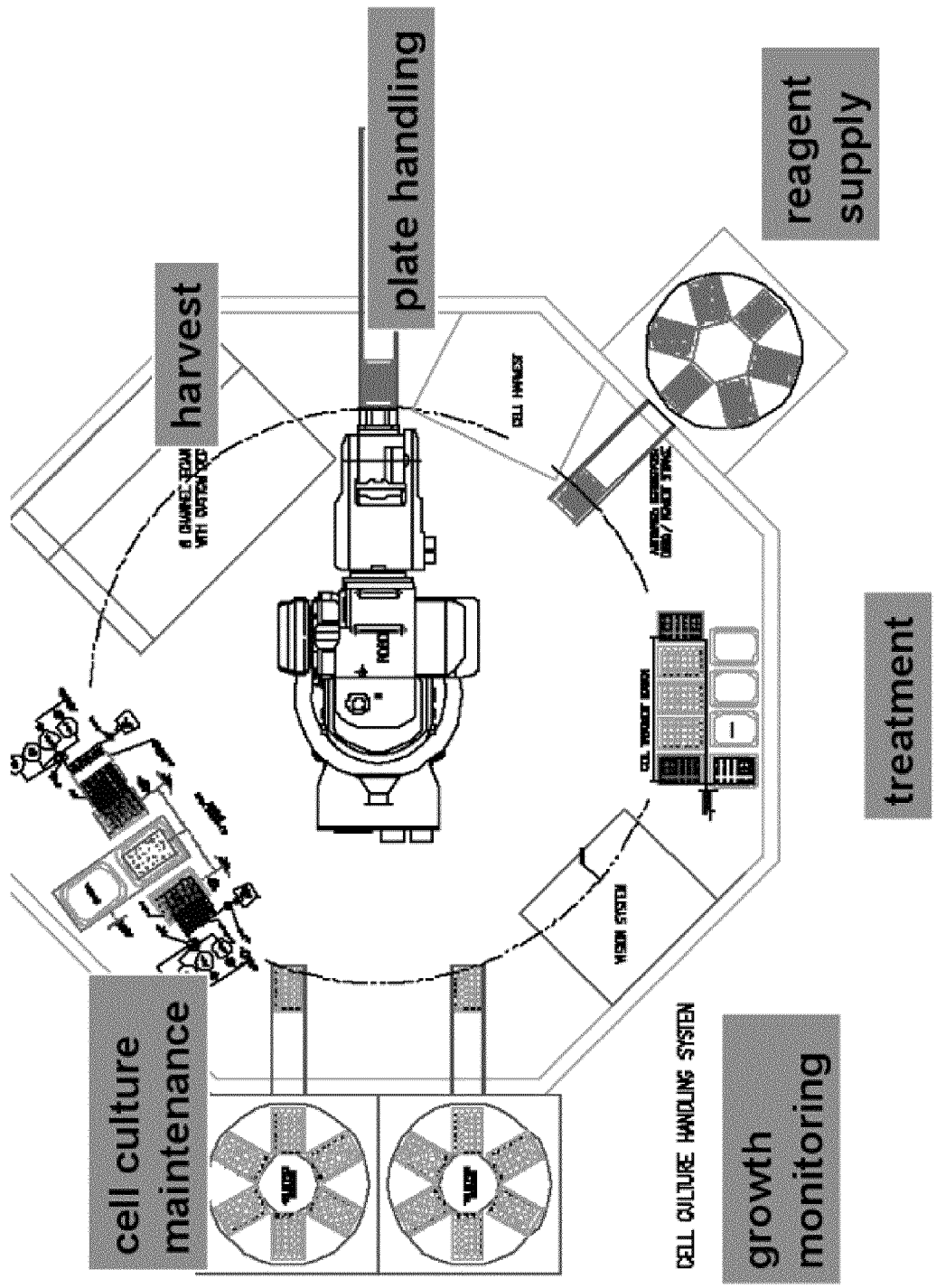
FIG. 15. Automated cell culture and manipulation system that can be used to assess responses of fibroblasts, keratinocytes and epithelial cells to nanomaterials.

In another embodiment, chemically induced toxicity ($IC_{50}$) is measured in cell lines for the nanomaterials being tested plus other compounds selected to induce stress or DNA damage, such as MNNG etc., which was used in previous studies (Yu, Y. et al. A comparative study of using comet assay and γH2AX foci formation in the detection of N-methyl-N'-nitro-N-nitrosoguanidine-induced DNA damage. *Toxicology In Vitro* In press (2006); Zhou, C. et al. DNA damage evaluated by γH2AS foci formation by a selective group of chemical/physical stressors. Mutation Res. In press (2006)). In one embodiment, epithelial cells, keratinocytes and fibroblasts will be grown in 24 well format and $IC_{50}$ values will be determined by measuring changes in cell number induced by each nanomaterial and reference compound. In all cases, cells will be analyzed in 24 well cultures established and maintained using the automated cell culture and manipulation instrumentation (FIG. 15). Cell number will be determined by staining cultures with 4',6-diamidino-2-phenylindole (DAPI), a fluorescent stain that binds strongly to DNA, automatically acquiring images of cells in each well and counting the number of DAPI stained cells in each well using the Cellomics Arrayscan V$^{TI}$ (Cellomics, Inc., Pittsburgh, Pa.) and associated software.

An evaluation matrix can be used that focuses on one variable at a time for each set of nanomaterials tested, and using PEG-passivated semiconductor nanocrystals as a control because the PEG passivated semiconductor nanocrystal induces minimal changes in gene expression, and can be a very good negative control (Data shown in Examples).

Stress Response.

In a preferred embodiment, the stress response of cells in response to nanoparticle treatment is evaluated. Responses to toxic chemicals typically include repression of protein synthesis and cell-cycle-regulated genes and induction of DNA damage and oxidative stress-responsive genes. These responses manifest at several levels. Others have shown, for example, that these responses can be revealed using microarray based analysis of gene expression and suggest the utility of assessing changes in gene expression as a sensitive way of identifying nanomaterial-induced stress. Transcript profiling technology or high-throughput 2D gel—mass spectrometry enable quantitative measurement of the transcriptional activity of thousands of genes and many proteins in biological samples. The application of such technology to toxicology, toxicogenomics and toxicoproteomics, promise substantial advances in mechanistic toxicity research and also the ability to predict adverse toxicity for novel or untested nanoparticles, if an evaluation matrix can be established by shape, surface charge and composition.

It is recognized that inflammation plays a central role in development of cancer. Inflammatory cells in "inflamed" tissues produce a variety of free radicals and Reactive Oxygen Species (ROS); free radicals and ROS exert effects on cells. The Examples demonstrate that stress response genes are perturbed by treatment with carbon nanomaterials. See Table 6, for example. For instance, of interest is the observation that MWCNTs appear to induce a greater amount of stress upon the cells than MWCNOs, even though the dosage is $1/10^{th}$ by weight/volume concentration.

Consistent with other assays, the present toxigenomic approach also find genes involved in inflammatory and innate immune response affected by nanoparticles. Mammals respond to wounding, pathogens, foreign particles and non-self proteins by activation of innate and adaptive immune systems. Chronic presence of a proinflammatory pathogen/particle leading to chronic activation of granulocytes is accompanied by production of $H_2O_2$ that can result in suppression of adaptive immune functions, specifically release of ROS. It will be important to investigate whether nanomaterials initiate "inflammatory-type" responses. Most importantly, with bioinformatics tools, the spatial-temporal activation of the immune response can be categorized by data clustering software, and expression patterns can be associated with specific size, shape and surface chemistry, and used as biomarkers.

In one embodiment, the stress responses of any cell type that can be cultured are measured. In a preferred embodiment, epithelial cells, keratinocytes and fibroblasts to agents known to induce stress responses (e.g., doxorubicin, 5-fluorouracil, mitomycin C and radiation) are measured. Changes in global gene expression patterns, p38 phosphorylation and COX-2 expression are assessed using microarray technologies and high content imaging, respectively.

In one embodiment, cells are exposed to the stress-inducing agents, such as doxorubicin, 5-fluorouracil, mitomycin C and radiation, at six different concentrations in 24 well cultures, preferably using automated cell culture and manipulation instrumentation as shown in FIG. 15 so that RNA can be harvested automatically. Global changes in gene transcription can be analyzed using the U133A expression microarray platform via the Affymetrix HTA system. These data are analyzed to identify stress response transcriptional signatures that are common to all agents.

In another embodiment, changes in COX-2 and phospho-p38 levels can be assessed using a high content imaging system after immunocytochemical staining for COX-2 and phospho-p38. In a preferred embodiment, a high-content fluorescence image analysis system, such as Cellomics ArrayScan (Cellomics, Inc., Pittsburgh, Pa.) is used to measure cellular responses to chemical and nanomaterials. The ArrayScan is an automated imaging instrument that scans through the bottom of clear-bottom 24-well plates, focuses on a field of cells, and acquires images at each selected color channel. The Cellomics software identifies and measures individual features and structures within each cell in a field of cells, so that up to hundreds of cell samples can be analyzed in parallel. The software then tabulates and presents the results in user-defined formats. In a preferred embodiment, these data are analyzed to identify COX-2 and phospho-p38 staining characteristics that are common to all chemicals. These signatures are then compared to nanomaterials-induced changes in order to identify nanomaterials that induce stress responses. For microarray experiments, it is preferred that 2 time points, once each at 2 hours and 8 hours is used to capture acute response.

Figure 16A:
FIG. 16. Two-dimensional gel electrophoresis analysis of multi-wall carbon nanoonion. A. untreated cell; B. treated cell; C and D. Mass spectrometry for two of the genes identified FIG. 17. Nanocrystals with different surface charges.
Figure 16B:
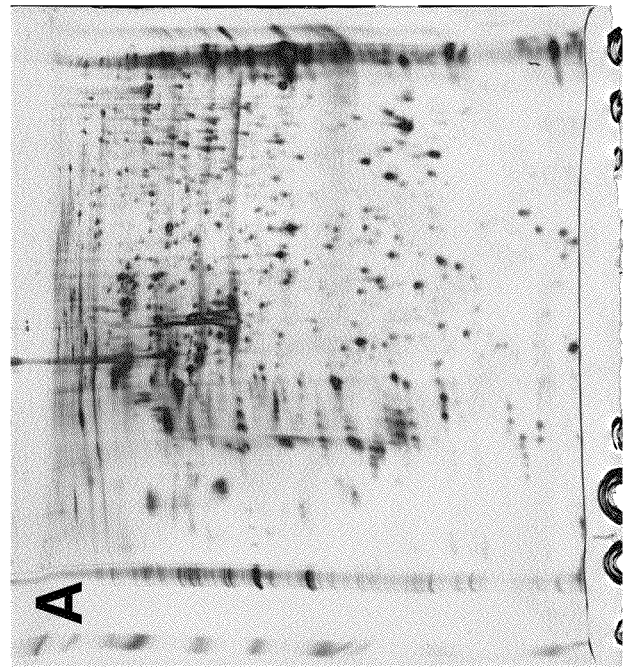
Figures 16C, 16D:
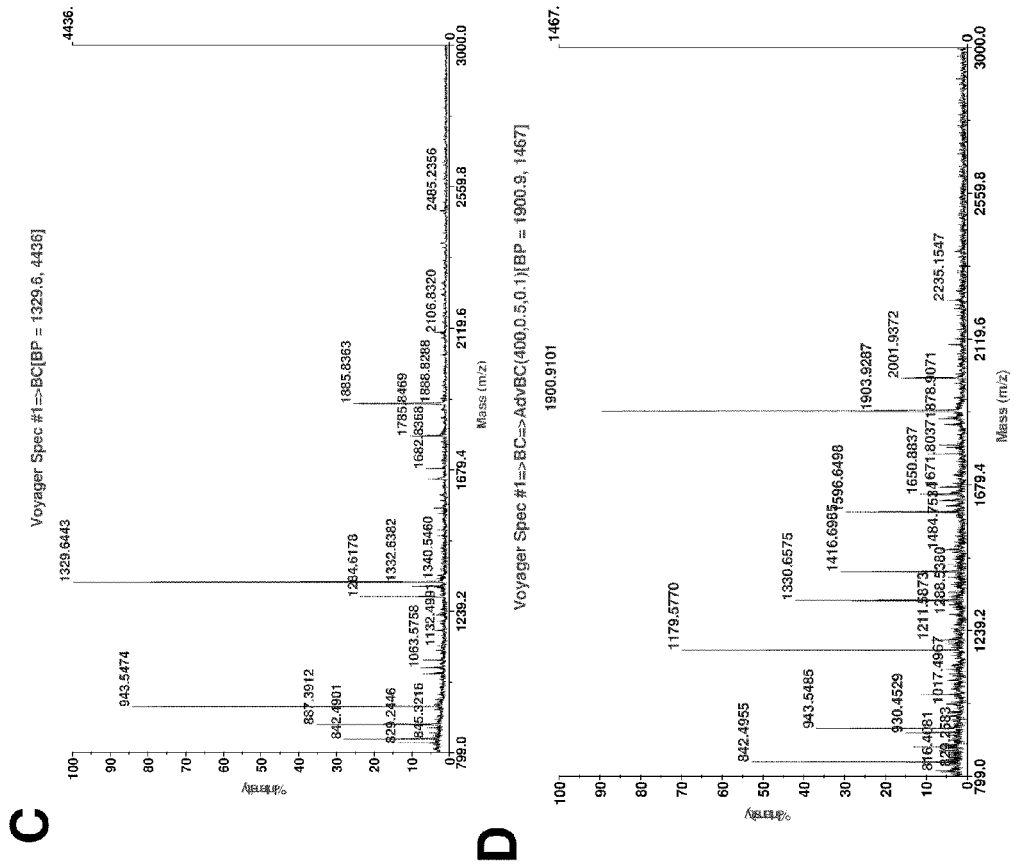
Figure 17:
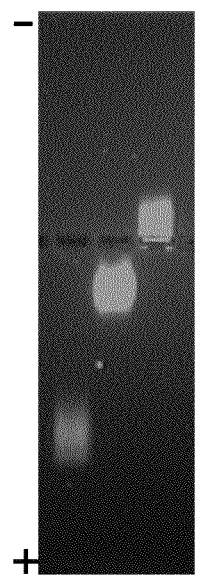
Figure 19:
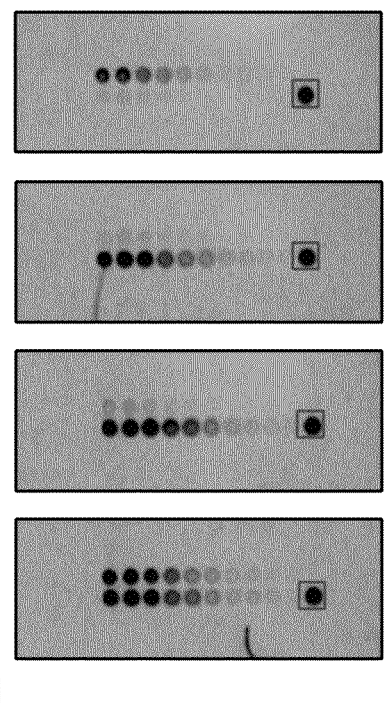
FIG. 19. Reverse phase protein array, probed with anti-pAkt.

In another embodiment, the nanomaterials are assessed using 2D-gels and/or mass spectrometry. For example, treated HSF cells are lysed and electrophoresed on the 2D gel as described below for FIG. 16. The first-dimension IEF was performed by using an Ettan IPGphor unit (Amersham Biosciences) with a power supply EPS 3501XL. The second-dimension SDS-PAGE is carried out in an Ettan DALTsix system (Amersham Biosciences). IPG strips were equilibrated and sealed on the top of 10% SDS gels with 0.5% SeaKem LE-agarose (Cambrex Corp.). SDS-PAGE was performed and the 2D gel silver stained (FIG. 12A). Gel was imaged with an Umax PowerLook 1100 scanner, and the spots are detected and automatched between the treated and untreated samples.

In the Examples, to identify differentially expressed proteins, the spots were excised from the gels with autopicker and digested with trypsin. Peptides were further extracted and concentrated and the resultant samples were then subjected to Q-TOF mass spectrometry. Mass spectra were processed by using MassLynx 4.0 software (Waters, Corporation, Milford, Mass.), and proteins were identified by using Protein Global Server 1.0/2.0 software, two of the proteins differentially expressed in MWCNO samples are presented in FIGS. 16C and D. For assays using 2D-mass spectrometry, it is preferred to use time points at 12 hours and 24 hours. Each time point should be done in triplicate.

The kinetic study will allow us to perform limited data clustering, and principal component analysis. In another embodiment, assays to perform G0 classification, promoter analysis, and pathway analysis can be performed to assist in measuring stress response.

Apoptosis.

Apoptotic cells can be detected based on nuclear morphology, mitochondrial mass and/or membrane potential and f-actin content after staining with the Cellomics Multiparameter Apoptosis 1 HitKit™ (Cellomics, Inc., Pittsburgh, Pa.). Nuclear morphology (condensation or fragmentation) is measured after staining with a stain such as Hoechst 33342. Mitochondrial membrane potential and mitochondrial mass is measured after staining with, for example, MitoTracker® Red (Molecular Probes, Invitrogen, Carlsbad, Calif.). F-actin can be measured after staining with an Alexa Fluor® 488 conjugate of phalloidin (Ax488-ph) (Molecular Probes, Invitrogen, Carlsbad, Calif.). An additional measure of apoptosis will include staining with Alexa Fluor® 488 conjugate of annexin V (Molecular Probes) and staining with propidium iodide (PI). PI cannot permeate apoptotic cells and live cells but can enter and bind nucleic acids in necrotic cells. When Hoechst 33342 is used as a counterstain, apoptotic cells fluoresce green, necrotic cells both green and red, and live cells only blue from the Hoechst stain.

Phenotypically, cells exposed to high concentrations of nanomaterials were observed to undergo apoptosis/necrosis with a concomitant reduction in proliferation indicative of an inflammation response. Thus assays to observe cell apoptosis/necrosis after exposure to nanomaterials can be performed as in Examples 3 and 7.

DNA Damage.

Figure 14:
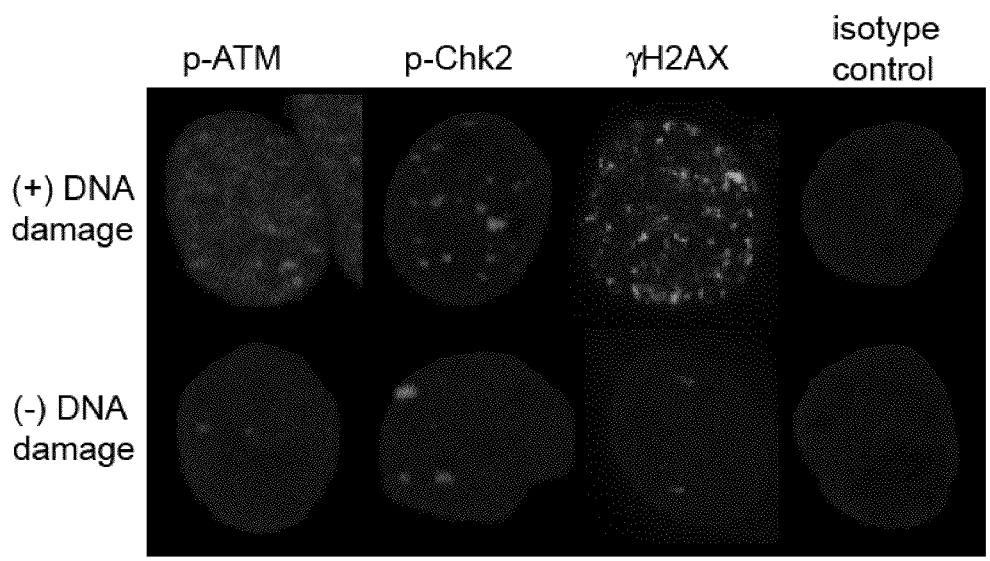
FIG. 14. Human epithelial cells with foci of activated DNA damage response proteins. Cells were exposed to 10 gray of radiation, processed and visualized as described in Methods. Aggregation of damage response proteins occurs within 6-hr.

In a preferred embodiment, mutagenic potential will be indexed by measuring induction of DNA damage, mutagenesis, and performing gammaH2AX foci formation and comet assays. DNA damage elicits several responses that can be quantified as an indication of the extent of damage. These include recruitment of p-ATM, p-Chk2 and gammaH2AX (FIG. 14) to sites of DNA damage, apoptosis and cell cycle inhibition.

Cells can be exposed to 6 doses/concentrations of radiation and mitomycin C in 24 well cultures using automated cell culture and manipulation instrumentation (FIG. 15). In a preferred embodiment, DNA damage induced by radiation, known mutagens, carcinogens or other materials is measured in order to calibrate DNA damage assays that will be used to assess DNA damage induced by nanomaterials. For example, one can stain p-ATM, p-Chk2 and gammaH2AX in interphase cells immunocytochemistry and determine number of fluorescently stained foci/nucleus using the Cellomics Arrayscan., whereby the number of foci will be used as an indication of extent of DNA damage (see Yu, Y. et al, *Toxicology In Vitro* In press (2006); Zhou C et al., *Mutation Res.* In press (2006)). In another embodiment, one can measure apoptosis indices (F-actin and Annexin V content) as an indication of extent of DNA damage-induced cell death. And in another embodiment, one can measure BrdUrd/DNA distributions as an indication of DNA damage-induced cell cycle inhibition. These endpoints should be measured for MCF10A, NHK and HSF42 cells at 2-, 8-, 24- and 48-hr after exposure to ascertain correct assay times for each endpoint. The low cost of Cellomics will allow these assays to be performed in high throughput fashion.

In a preferred embodiment, DNA damage and chromosomal aberration is measured by using comparative genomic hybridization (CGH). ArrayCGH is performed to allow global profiling of gene amplification/deletion to generate genome instability data after chronic treatment by the nanomaterial.

Another aspect associated with oxidative damage is mutagenesis and carcinogenesis. It is still unknown whether chronic exposure to nanomaterials will induce meaningful genome instability to be mutagenic and carcinogenic. Mutagen sensitivity, measured as mutagen-induced chromatid breaks per cell has been used to study susceptibility to various epithelial cancers. One of the whole genome scanning techniques is comparative genomic hybridization (CGH), which provides global assessment of genome instability and carcinogenesis. CGH is a powerful genome-wide method for molecular cytogenetic analysis of cancer as described in Kallioniemi, A. et al. Comparative genomic hybridization for molecular cytogenetic analysis of solid tumors. *Science* 258, 818-821 (1992), and incorporated by reference. It has been used successfully in molecular classification and diagnosis of carcinomas, such as melanoma, breast cancer, ovarian cancer, lung cancer, etc. CGH allows detection and mapping of allelic imbalance by simultaneous in situ hybridization of differentially labeled tumor genomic DNA (green fluorescing) and normal reference DNA (red fluorescing) to a normal human metaphase spread. Regions of increased or decreased copy number in the tumor are mapped onto the normal metaphase chromosomes as increases or decreases in the green to red fluorescence ratio for each locus. Fluorescence ratios along the length of the chromosomes provide a cytogenetic representation of DNA copy-number variation.

Specific methods for carrying out each of these assays are described below and in Example 1 and 7. In a preferred embodiment, the treatment experiments are carried out using an automated cell culture system as shown in FIG. 15. Genome instability index will serve as an additional indicator for carcinogenesis/mutagenesis potential.

In another embodiment, the cytotoxicity of nanomaterials can be determined using three-dimensional tissue culture models. The stromal microenvironment contributes significantly to establishment of cancer and can modulate metastatic dissemination; thus, it is speculated that nanomaterial disruption of this microenvironment may be carcinogenic. The extent to which nanomaterials modulate signaling from the microenvironment to epithelial cells can be explored by investigating the extent to which nanomaterials influence proteins and phosphoproteins involved in signaling from the microenvironment in breast epithelial cells.

In another embodiment, 3DBM cultures can be used to assess impact of nanomaterials with emphasis on those that are found to be toxic, induce stress or DNA damage OR that are intended for interrogation of living systems. Endpoints that can be assessed include (a) transcript profiles as measured on the Affymetrix HTA system using U133A arrays, (b) proteins involved in signaling from the ECM including β1 integrin, EGFR, αvβ6 integrin, MAPK, PI3K, ErbB2, CAR, PDGF, Src, Fn14 and LTβ(c) Cell morphology will be imaged daily for 6 days. Cellular response to treatment will be assessed by morphological criteria, e.g. size of cell clusters or smooth or roughness of edges. Day 6 controls and wells which are deemed of interest (cells which have been visibly altered by treatment compared to control) will be treated with Matrisperse so that cell structures can be dispersed onto glass slides, fixed and assessed for cell proliferation, polarity and apoptosis. For microarray expression analysis, four 35 mm plates of cells will be cultured in 3D as described above. Again, representative cultures will be viewed daily and on day 6 plates treated with PBS w/o Ca & Mg+EDTA to release cellular structures. Disaggregation to single cells will be accomplished enzymatically so that epithelial and stromal cells can be purified by magnetic beads using cell surface antibodies as described above. Purified cells will be used to isolate RNA using Qiagen RNAeasy kit or to make protein lysates.

Experience indicates that in vitro basal cytotoxicity data determined in primary and/or transformed cell lines, generally exhibit comparable cytotoxic concentrations of xenobiotics, regardless of type of toxic endpoints investigated. However, while strong correlations between cytotoxicity in vitro and animal lethality do exist, in vitro analyses alone cannot completely predict pathophysiologic consequences of a potentially hazardous chemical/particle in vivo. Importantly, these parameters of safety cannot be efficiently modeled in cell culture, however the 3D culture model is closer than the 2D culture model to in vivo reality.

With the growing awareness that tumors consists of not only developing cancer cells, but also a diverse assortment of "host" cells that coexist in a dynamic microenvironment, 3D tissue culture models allow the microenvironment to be partially duplicated and allow these interactions to be defined and functionally accessed; significantly, such parameters may not be readily modeled in 2D cell culture, yet would be too expensive and time-consuming to test in animal models. In a preferred embodiment, utilizing the above mentioned and highly characterized assays, comparison of the genomic and proteomic profile of the nanomaterial in 2D vs. 3D, and assessment of inherent carcinogenic risks of manufactured nanomaterials as well as determining if they possess tumor promotion or progressor properties is carried out.

In a preferred embodiment, a study is performed on whole organisms. A living system may have several lines of defense to prevent or minimize some of the toxic effects of exposure to small particles, thus in a preferred embodiment, animal and human studies should be carried out.

While much has been learned regarding synthesis of nanomaterials, little is known about cellular details or organ responses upon contact with nanomaterials. A defining feature of nanomaterials is their large specific surface area; thus, it is possible that current concepts of dose expressed as mass concentration, which are low for nanomaterials, may not be sufficient in predicting exposure outcomes. One prediction based on their small size is that nanomaterials may evade normal particle clearance mechanisms in tissues/organs in vivo. If nanomaterials fail to be efficiently cleared, their risk of cellular contact will be enhanced. Inappropriate cellular contacts may stimulate inflammatory and/or oxidative stress responses that could then be potentiated by large surface areas (relatively) of nanomaterials and result in specific or systemic dysfunction.

Thus, the present approach will be to use well-characterized models of cell physiology of increasing relevance and complexity to investigate nanoparticle-induced changes that may indicate toxic or carcinogenic effects. First, high throughput genomic and proteomic analysis strategies to identify physiologic effects of nanoparticles in epithelial cells, keratinocytes and fibroblasts in two-dimensional (2D) cell cultures are carried out. Based on our molecular profiling findings, changes can be assessed in expression of genes involved in intracellular transport, metabolism, inflammation, apoptosis/necrosis, oxidation and reduction and in activation of signaling pathways implicated in carcinogenesis (e.g. PI3-kinase, MAP-kinase, cytochrome P450, glutathione transferase, etc) using a variety of assays, including, but not limited to, expression arrays and reverse phase protein lysate arrays, and two dimensional gel electrophoresis-mass spectrometry (2D-MS) technologies. Cellular changes in proliferation, survival, apoptosis and motility are then assessed using such assays as high throughput flow cytometry and multi-well Cellomics image analysis. Nanomaterials that regulate gene expression associated with toxicity or carcinogenesis will be tested as well. Lastly, the nanomaterials should be tested using three dimensional (3D) cultures that mimic microenvironments in vivo (i.e. cell-ECM, cell-cell-myoepithelial and stromal-interactions. In combination, these assays will examine nanoparticle effects on cutaneous cellular systems. Furthermore, in comparison with data and Tables described herein for semiconductor nanocrystals, multi-wall carbon nanotubes and multi-wall carbon nanoonions, the cytotoxicity of a nanomaterial and the acceptable exposure dosage can be predicted.

The present invention further provides kits for diagnosing the cytotoxicity of a nanomaterial. Furthermore, the biomarkers described herein and in the Examples can be used to select and/or develop the suitable instruments and methods for measuring exposure to particles according to the health affects. An ideal instrument would be a biosensor or lab on an array chip device that industry could use to batch test materials.

Cytotoxicity of Carbon Nanomaterials

The data and results acquired using the methods described supra show the existence of these nanoscale effects and molecular effectors are instrumental in differentiating nanotoxicology from conventional toxicology. Furthermore, the biomarkers described herein and in the Examples can be used to select and/or develop the suitable instruments and methods for measuring exposure to particles according to the health affects. An ideal instrument would be a biosensor or lab on a chip device that industry could use to batch test materials.

To address this question of cytotoxicity of nanomaterials, whole genome expression array analysis and high content image analysis-based phenotypic measurements were performed on human skin fibroblast cell populations exposed to multiwall carbon nano-onions (MWCNOs) and multiwall carbon nanotubes (MWCNTs). Herein it is demonstrated that exposing cells to MWCNOs and MWCNTs at cytotoxic doses induces cell cycle arrest and increases apoptosis/necrosis. Expression array analysis indicates that multiple cellular pathways are perturbed after exposure to these nanomaterials at these doses, with material-specific toxigenomic profiles observed. Moreover, there are also distinct qualitative and quantitative differences in gene expression profiles, with each material at different dosage levels. MWCNO and MWCNT exposure activates genes involved in cellular transport, metabolism, cell cycle regulation, and stress response. MWCNTs induce genes indicative of a strong immune and inflammatory response within skin fibroblasts, while MWCNO changes are concentrated in genes induced in response to external stimuli. Promoter analysis of the microarray results demonstrate that interferon and p38/ERK-MAPK cascades are critical pathway components in the induced signal transduction contributing to the more adverse effects observed upon exposure to MWCNTs as compared to MWCNOs.

Figure 4:
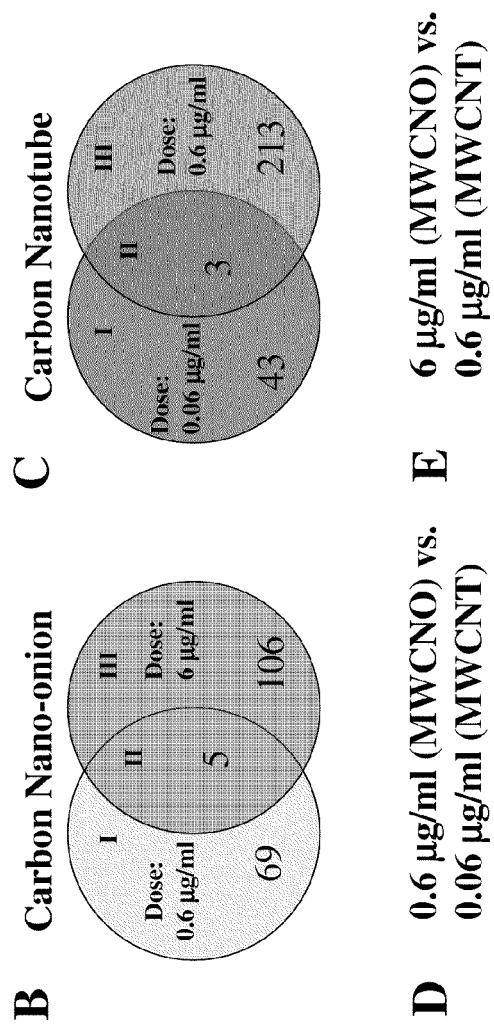
FIG. 4. A. Numbers of genes whose expression levels changed after treatment with carbon nanomaterials at cytotoxic doses. B-E. Venn diagrams comparing numbers of genes that showed expression changes. Each Venn diagram is divided into 3 areas and labeled as I, II and III. Area II is the overlapping area of two circles, represent commonly changed genes in both conditions. Area I and III represent genes that changed only in the condition specified in the circle. Bioconductor software was used to perform significance analysis to determine the difference between expression levels in treated sample and control sample possesses statistical significance. The empirical Bayesian model was used with Bonferroni's multi-test correction. The cutoff of p-values produced through the analysis was determined by at least 10 times less than the p-values of the smallest p-value of control probe sets on the chip. B, comparing different doses for the nano-onions. C, comparing different doses for the nanotubes. D, comparing different particles at low doses (0.6 µg/mL for MWCNO and 0.06 μg/mL for MWCNT). E, comparing different particles at high doses (6 μg/mL for MWCNO and 0.6 μg/mL for MWCNT).

By applying significance analysis with very conservative Bonferroni multi-testing correction, a number of genes are found with statistically significant expression level changes (FIG. 4, Table 9-21). Treating cells at the high dose of carbon particles caused more gene expression changes than the low dose treatment (FIG. 4). As shown in FIGS. 4B and 4C, only a small portion of genes with altered transcription were found in common between the low and high dose profiles, when treating with same type of particle. This indicates that distinct gene expression profiles were induced at low and high dose treatment. In contrast, if we compare two types of particles, they induced similar transcriptional changes in cells at the same doses (FIGS. 4D and 4E). The unique genes flanking the overlapping area in FIGS. 4D and 4E may indicate cellular responses unique to exposure with MWCNOs or MWCNTs (Supplement Tables 15, 17, 18, and 20).

Figure 7:
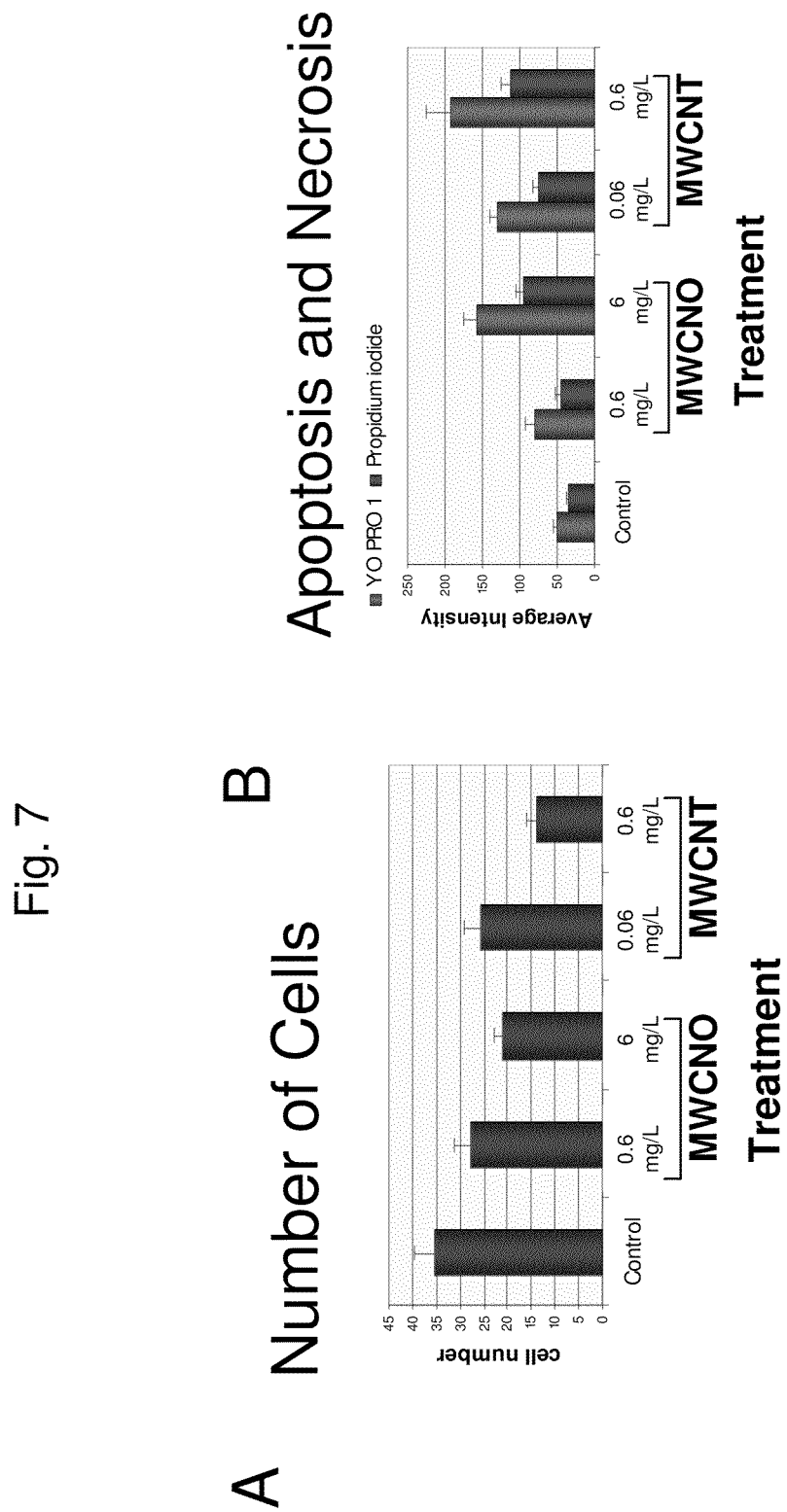
FIG. 7. A. Same as in FIG. 2, except lung fibroblasts were treated. B. Average intensity of YO-PRO1 intensity and PI intensity of mock treated and treated lung fibroblasts at 48 hours. Bars represent the mean of cell numbers from eight treated wells and the error bars represent a 95% confidence interval.

The results presented here show for the first time both a phenotypic response of cells to carbon nanomaterials (apoptosis, necrosis, cell cycle perturbation, and anti-proliferation) and a global gene expression response at a cellular level. Phenotypic effects were confirmed two different fibroblast cell types, human skin fibroblast (HSF, see Figures and Tables in text) and IMR-90 (FIG. 7). This information will be important for elucidating possible mechanisms responsible for the toxicity observed after exposure to these particles. Important to the validation of this experimental approach was to determine if the microarray results were consistent with our phenotypic observations of exposed cells by high content analysis (HCA). The phenotypic responses of apoptosis, cell death, and proliferation changes were predicted by changes in expression levels of many of the genes we observed.

HCA of cells treated with MWCNOs, MWCNTs and semiconductor nanocrystals showed significant changes in cell number that, upon further investigation, was shown to be due to apoptosis, cell death and proliferation changes. Therefore it can be concluded that nanomaterials in general do demonstrate toxicity, especially at higher concentrations. Size and shape of the nanomaterials also appears to affect toxicity levels. Thus, the present invention establishes sets of biomarkers whose gene expression levels are changed in response to exposure to carbon nanomaterials. It was found that particular biological pathways are activated or perturbed by nanoparticle. The biological pathways activated or perturbed include the pathways of inflammation, apoptosis, immune response, ubiquitination, cell proliferation, cell cycle regulation, cell differentiation, golgi vesicle transport, membrane fusion, secretory pathway, intracellular transport, nucleocytoplasmic transport, apoptosis, response to DNA damage, response to stress and stimuli. These pathways and the nanoparticle specific biomarkers are listed in Tables 2-7 and 8-21.

Thus, in one aspect, using the biomarkers identified that are associated with particular nanoparticles, it is possible to evaluate the cytotoxicity of various nanomaterials using the biomarkers and biomarker temporal change patterns as predictors for other nanoparticles. Any nanomaterial can be evaluated including, but not limited to, nanomaterals that are carbon-based (such as carbon nanotubes and spherical carbon nanoparticles) or semiconductor-based (such as semiconductor nanocrystals), or metal-oxide based, any nanomaterial comprised of combinations, and derivates thereof, having any contemplated modification thereof. The biomarkers identified in the Tables will prove useful as a baseline for future studies or assessment of nanomaterials.

In a preferred embodiment, gene expression changes in human skin fibroblasts serve as a readout for cellular responses to the stimulus of carbon nanomaterials. As used herein the term, "gene expression" is used in a broad sense. It comprises an increase or decrease of gene copy number; it can also comprise assessment of amplification or decrease in levels of the gene, and/or gene products. Thus levels of gene expression, as well as corresponding protein expression can be evaluated. In the embodiments that follow, it is understood that assessment of gene expression can be used to assess level of gene product such as RNA or protein.

Another aspect of the invention is the sensitivity of the assay system on nanotoxicity, when microarray technology is used here. The invention here provides guidelines for the threshold of cytotoxicity and the correlation with gene expression profile changes. In a preferred embodiment, the threshold is defined as 1% of total genes are changed more than two-fold. In another embodiment, measuring a two-fold or more change in the gene expression of a specific gene or set of genes listed in Tables 2-7 or Table 8-21 in response to exposure to a nanomaterial, is an indicator of nanotoxicity of the nanomaterial.

Notwithstanding the above the discussion, nanomaterials such as quantum dots that are well-attenuated by protective outer coatings, such as polyethylene glycol, may exhibit gene changes of less than 0.5% of total genes. As described in Example 6, the data uncovers a surprising observation, that low or high dosages of semiconductor nanocrystals ("Qdots") during the incubation step does not induce a marked difference in the phenotypic response of cells. The higher dosage of semiconductor nanocrystals during incubation does however result in a higher degree of particle uptake as measured by a stronger fluorescent signal. It is unclear, however, if the 10-fold increase of PEG-silane-semiconductor nanocrystals used for the incubation period results in a 10-fold increase of particle uptake. Of importance, the high concentration of Semiconductor nanocrystals used in this study corresponds to an approximately 5-fold greater concentration than reported previously in toxicity studies using non-PEGylated semiconductor nanocrystals. (Maynard, A. D. et al. Exposure to carbon nanotube material: aerosol release during the handling of unrefined single-walled carbon nanotube material. *J Toxicol Environ Health A* 67, 87-107 (2004)). Despite this high concentration, skin HSF-42 and lung IMR-90 cells only show a mild phenotypic response to PEG-silane-semiconductor nanocrystals, as measured by changes in cell proliferation, cell cycle regulation and cell death and shown in Tables 7-8.

Thus, in a preferred embodiment, the gene expression change level of less than 0.5% of total genes can be used as a quantitative measurement on whether the protective coating is effective for any other nanoparticles, or nanomaterials. In the field of semiconductor nanocrystals alone, multiple surface chemistries are available for solubilizing the nanoparticle, yet most of them do not prevent the leaking of Cd heavy metal into the solution, killing the cells for biological applications. The microarray gene expression analysis provides quantitative and comprehensive measurement matrix for determine the effectiveness of the protective coating. This quantitative measurement can be used for any other nanoparticles that might have toxicity against the cells, tissues, or organs. Surface modifications can include charge density alteration by introducing positively or negatively charge groups, encapsulation by polymers, lipids, inorganic thin films, biocompatible materials, and biomolecules including biopids, biominerals, polysaccharides, nucleic acids, dendrimers, aptamers, polypeptides, proteins. And nanocomposites which are a combination of more than two of the above variations.

The gene ontology classification methods used also are very powerful indicators for the primary effect of the nanoparticles/nanomaterials on the particular genes in various biological pathways. For instance (Table 1), 2% percentage of genes in the Golgi body transport pathways are changed after treatment, with P value <0.0001.
The enrichment of certain gene ontology classes above the background percentage levels of the total genome indicates a likelihood that there is an increase in expression of certain impacted groups. The fold change of enrichment will be a useful quantitative index for determining the relative toxicological impact of a particular nanomaterial on an affected gene class relative to the impact on the overall genome. One way of looking at this fold change is by determining the ratio of affected genes to the number of genes in the pathway compared to the ratio of genes in the pathway to the overall genome.

In Example 1, gene ontology analysis gave further evidence supporting the qualitative differences of cell responses to low and high doses of carbon nanomaterials. The percentages of over-expressed and under-expressed genes in the top 10 most affected gene categories were shown in Table 1. The only up-regulated category was protein ubiquitination (Table 1, Table 21). Collectively, this data suggested a reduction of cell growth and metabolism, but an acceleration of protein degradation at the low dosage.

In another aspect, the genes identified and similar gene profiles identified using similar assay systems can be used as guidelines for attenuating the toxic effects. The biomarker changes should be eliminated or weakened, with the elimination of the nanotoxicity. This can be used as a measurement on the efficiency of toxicity control.

Thus, embodiments of the invention include: A method for prognosing the cytotoxic effect of a nanomaterial upon a cell, said method comprising: providing a cell; exposing said cell to a nanomaterial; detecting from the provided cell, the level of gene amplification or gene expression for at least one gene set forth in Tables 2-21 in response to said exposure; identifying at least two-fold change in gene expression of said gene; whereby, when the two-fold change in gene expression is identified, this is an indication that the nanomaterial is cytotoxic to said cell. This method can comprise that the gene or gene product is involved in ERK and p38 MAPK activities and the induction of interferon signaling. The detecting step can comprise use of a methodology selected from the group consisting of transcription profiling, the measurement of phenotypic changes in large populations of cells by high content analysis, gene expression array analysis in exposed cells, measuring mRNA level changes, promoter analysis, chemically induced toxicity, 2D gel electrophoresis, mass spectrometry, reverse phase protein lysate arrays for protein, In another embodiment, specific cellular response to nanomaterial exposure is measured by determining, (a) toxicity of the nanomaterials by (i) the measurement of phenotypic changes in large populations of cells by high content analysis and (ii) gene expression array analysis in exposed cells; (b) DNA damage and chromosomal aberration caused by the nanomaterials and measured by using comparative genomic hybridization (CGH), and performing gammaH2AX foci formation and comet assays, (c) stress response due to nanomaterial exposure by measuring changes in global gene expression patterns, p38 phosphorylation and COX-2 expression using microarray technologies and high content imaging, and (d) apoptosis levels by detecting apoptotic cells based on nuclear morphology, mitochondrial mass and/or membrane potential and f-actin content after staining. In preferred embodiments, these assays are carried out in 3D culture environments, such as MATRIGEL. In another preferred embodiment, these assays are carried out in a mammalian organism, such as a mouse, pig, or human.

Therapeutic Uses for Carbon Nanomaterials

The present invention further provides multi-walled carbon nanomaterials and therapeutic uses thereof. In a preferred embodiment, the multi-walled carbon nanomaterials used herein are carbon nanotubes or nanoonions, more preferably nanoonions. The regulation of p38/ERK and the EGFR also provides for the use of carbon nano-onions and potentially other carbon nanomaterials to be exploited as a nanomedicine platform for cancer therapy, especially epithelially derived cancers.

Mutiwall Carbon Nanomaterials.

In one embodiment, multi-walled carbon nanotubes are synthesized by using a chemical vapor deposition (CVD) method as described in Service, R. F. American Chemical Society meeting. Nanomaterials show signs of toxicity. *Science* 300, 243 (2003), and Andrews, R., Jacques, D., Qian, D. & Rantell, T. Multiwall carbon nanotubes: synthesis and application. *Acc Chem Res* 35, 1008-1017 (2002), both of which are hereby incorporated by reference. Example 1 also describes a preferred method for synthesizing multiwall carbon nanotubes.

In another embodiment, multi-walled carbon nanoonions are synthesized by using the direct-current electric-arc discharge method described in Sano, N., Wang, H., Chhowalla, M., Alexandrou, I. & Amaratunga, G. A. J. Nanotechnology: Synthesis of carbon 'onions' in water. *Nature (London)* 414, 506-507 (2001) and hereby incorporated by reference. In another embodiment, a preferred method described in Examples is used for synthesizing the carbon MWCNOs. FIGS. 1B and 1D show the carbon nanoonions produced by the preferred method.

In a preferred embodiment, the multiwall carbon nanonions are approximately 10-50 nm in diameter, more preferably about 30 nm. By the term "about" it is meant, that it is contemplated that the size can be within ±5, 10, 15, 20, or 25 units or 5, 10, 15, 20, or 25% of the stated values.

The multiwall carbon nanomaterials may be "conjugated" (i.e., linked) to a biological molecule or composition, directly or via one or more linking agents. "Linking agent" as used herein refers to any compound that forms a bond between the nanomaterial and the biological molecule and includes e.g., a functional group, an affinity agent, or a stabilizing group. Suitable bonds include ionic interactions, covalent chemical bonds, physical forces such van der Waals or hydrophobic interactions, encapsulation, embedding, binding affinity, attraction or recognition, and various types of primary, secondary, tertiary linkages including but not limited to, peptide, ether, ester, acryl, aldehyde, ketone, acryloyl, thiol, carboxyl, hydroxyl, sulfhydryl and amine linkages or the like.

The biological molecule or composition can be a radioactive label, such as Gd-DPTA, $^{19}$F, $^{1}$H, or $^{125}$I, and serve as a MRI contrasting reagent; radionuclides, such a $^{64}$Cu, F, I, Cl, Br, for use in PET imaging; or imaging reagents such as fluorescent or chemiluminescent probes for use in infrared imaging. In the imaging-enhanced versions of the nano-onions, it is contemplated for uses such as, as a tool for image-guided intervention of tumors.

The multiwall carbon nanomaterials can also be conjugated to tumor-targeting molecules, such as monoclonal antibodies, nucleic acids, peptides, small molecules, etc., whereby the targeted nano-onion can be carried in vivo to a tumor to kill the tumor cells. In another embodiment, the nanomaterial is conjugated one or more antibody, composition, small molecule, nucleic acid or peptide that binds to any one of the genes known to be upregulated in cancer cells, such as Erbβ2 and EGFR. In another embodiment, the multiwall carbon nanomaterial is conjugated to a small molecule such as folate, any vitamin specific for a disease, or a drug such as quinazoline derivatives which act as tyrosine kinase inhibitors (e.g., Erlotinib and Gefitinib). In another embodiment, the nucleic acid or peptide is an antisense oligonucleotide, aptamer or siRNA specific for a cancer marker.

In a preferred embodiment, the multiwall carbon nanomaterial is conjugated to a monoclonal antibody anti-Erbβ2, which targets tumor cells or inserted into a delivery vehicle having an anti-Erbβ2 monoclonal antibody. ErbB-targeted therapy has been validated with FDA approval of the ErbB2 binding Mab, trastuzumab (HERCEPTIN) for treatment of advanced breast cancer. Trastuzumab binds to the receptor extracellular domain resulting in tumor growth inhibition via poorly understood mechanisms, although both antibody dependent cellular cytotoxicity and interference with receptor signaling probably play a role in therapeutic efficacy (Albanell, J., Codony, J., Rovira, A., Mellado, B., and Gascon, P. (2003). Mechanism of action of anti-HER2 monoclonal antibodies: scientific update on trastuzumab and 2C4. Adv Exp Med Biol 532, 253-268; Clynes, R. A., Towers, T. L., Presta, L. G., and Ravetch, J. V. (2000). Inhibitory Fc receptors modulate in vivo cytoxicity against tumor targets. Nat Med 6, 443-446). In 2004, an EGFR binding mAb, cetuximab (ERBITUX), was approved for treatment of colorectal carcinoma (Starling, N., and Cunningham, D. (2004). Monoclonal antibodies against vascular endothelial growth factor and epidermal growth factor receptor in advanced colorectal cancers: present and future directions. Curr Opin Oncol 16, 385-390). Additionally, the small molecule kinase inhibitor gefitinib (IRESSA) has been approved for treatment of non-small cell carcinoma of the lung (Cohen, M. H., Williams, G. A., Sridhara, R., Chen, G., McGuinn, W. D., Jr., Morse, D., Abraham, S., Rahman, A., Liang, C., Lostritto, R., Baird, A., and Pazdur, R. (2004). United States Food and Drug Administration Drug Approval summary: Gefitinib (ZD1839; Iressa) tablets. Clin Cancer Res 10, 1212-1218). A host of new ErbB-targeted agents with diverse mechanisms of action are also in pre-clinical and clinical development. These include: other naked MAbs directed against EGFR or ErbB2, mAbs that block ErbB2-ErbB3 heterodimerization, anti-ErbB2 bispecific MAbs, anti-EGFR and anti-ErbB2 immunotoxins, anti-ErbB2 immunoliposomes (ILs), anti-ErbB2 vaccine constructs, small molecule inhibitors of ErbB kinase activity, and downmodulators of ErbB expression (reviewed in El-Rayes, B. F., and LoRusso, P. M. (2004). Targeting the epidermal growth factor receptor. Br J Cancer 91, 418-424; Gross, M. E., Shazer, R. L., and Agus, D. B. (2004). Targeting the HER-kinase axis in cancer. Semin Oncol 31, 9-20; Noonberg, S. B., and Benz, C. C. (2000). Tyrosine kinase inhibitors targeted to the epidermal growth factor receptor subfamily: role as anti-cancer agents. Drugs 59, 753-767; Park, J. W., Benz, C. C., and Martin, F. J. (2004). Future directions of liposome- and immunoliposome based cancer therapeutics. Semin Oncol 31, 196-205).

It is further contemplated that the carbon nanomaterials are multi-modality and are conjugated to both an imaging reagent and a tumor-targeting molecule. It is further contemplated that these multi-modality carbon nanomaterials are also crosslinked, bound or encapsulated with an immunoliposome as described in Example 6, whereby the immunoliposome is conjugated to tumor-targeting molecules, such as monoclonal antibodies, peptides, small molecules, etc., whereby the targeted nanomaterial can be carried in vivo to a tumor to kill the tumor cells. In another embodiment, the nanomaterial immunoliposome is conjugated to one or more antibody, composition, small molecule, nucleic acid or peptide that binds to any one of the genes known to be upregulated in cancer cells, such as Erbβ2 and EGFR. In another embodiment, the nanomaterial immunoliposome is conjugated to a small molecule such as folate, any vitamin specific for a disease, or a drug such as quinazoline derivatives which act as tyrosine kinase inhibitors (e.g., Erlotinib and Gefitinib). In another embodiment, the nucleic acid or peptide is an antisense oligonucleotide, aptamer or siRNA specific for a cancer marker.

Therapeutic Delivery.

In certain embodiments, the inventors contemplate the use of liposomes, nanocapsules, microparticles, microspheres, lipid particles, vesicles, and the like, for the administration of the multi-wall carbon nanomaterials of the present invention. In particular, the compositions of the present invention may be formulated for delivery either encapsulated in or bound to a lipid particle, a liposome, a vesicle, a nanosphere, or a nanoparticle or the like.

The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon & Papahadjopoulos, 1988; Allen and Choun, 1987; U.S. Pat. No. 5,741,516). Further, various methods of liposome and liposome like preparations as potential drug carriers may be used (Takakura, 1998; Chandran et al, 1997; Margalit, 1995; U.S. Pat. No. 5,567, 434; U.S. Pat. No. 5,552,157; U.S. Pat. No. 5,565,213; U.S. Pat. No. 5,738,868 and U.S. Pat. No. 5,795,587).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 m. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the nanomaterial compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

Targeting is generally not a limitation in terms of the present invention. However, should specific targeting be desired, methods are available for this to be accomplished. For example, antibodies may be used to bind to the liposome surface and to direct the liposomes and its contents to particular cell types. Carbohydrate determinants (glycoprotein or glycolipid cell-surface components that play a role in cell-cell recognition, interaction and adhesion) may also be used as recognition sites as they have potential in directing liposomes to particular cell types. For example, in one embodiment, the multiwall carbon nanomaterials are crosslinked to an immunoliposome. In a preferred embodiment, the immunoliposome and methods of use as described in U.S. Pat. Nos. 6,071,533; 6,410,049; 5,980,935; 6,110,491; 6,210,707 and 6,214,388, which are hereby incorporated by reference in their entirety, are used to make multi-wall carbon nanomaterials immunoliposomes for targeted delivery.

Alternatively, the invention provides for pharmaceutically-acceptable nanocapsule formulations of the compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 m) should be designed using polymers able to be degraded in vivo. Biodegradable polyalkyl-cyanoacrylate nanoparticles that meet these requirements are contemplated for use in the present invention. Such particles may be easily made, as described (Couvreur et al., 1980; 1988; zur Muhlen et al., 1998; Zambaux et al 1998; Pinto-Alphandry et al., 1995 and U.S. Pat. No. 5,145,684). Others have described nanoparticles in U.S. Pat. Nos. 6,602,932; 6,071,533.

It is further contemplated that the multi-wall carbon nanomaterials of the present invention is delivered to cancerous cells in a subject using other microparticles, nanostructures and nanodevices. For example, microspheres may be used such as those available from PolyMicrospheres, Inc. (Indianapolis, Ind.). For descriptions of drug delivery, see generally Alivisatos A P, Less is more in medicine, *Understanding Nanotechnology*, Warner Books, New York, 2002; Max Sherman, The World of Nanotechnology, *US Pharm.* 2004; 12:HS-3-HS-4; Brannon-Peppas and Blanchette, Nanoparticle and targeted systems for cancer therapy, *Advanced Drug Delivery Reviews*, Intelligent Therapeutics: Biomimetic Systems and Nanotechnology in Drug Delivery, Volume 56, Issue 11, 22 Sep. 2004, Pages 1649-1659; and D. M. Brown, ed., *Drug Delivery Systems in Cancer Therapy*, Humana Press, Inc., Totowa, N.J. 2004, including Chapter 6: Microparticle Drug Delivery Systems by Birnbaum and Brannon-Peppas, pp. 117-136, all of which are hereby incorporated by reference.

Methods of Treatment.

The nanomaterials of the present invention can be used to treat or prevent a variety of disorders associated with cancer. The nanoonions are administered to a patient in an amount sufficient to elicit a therapeutic response in the patient (e.g., inhibiting the development, growth or metastasis of cancerous cells; reduction of tumor size and growth rate, prolonged survival rate, reduction in concurrent cancer therapeutics administered to patient). An amount adequate to accomplish this is defined as "therapeutically effective dose or amount."

The nanomaterials of the invention can be administered directly to a mammalian subject using any route known in the art, including e.g., by injection (e.g., intravenous, intraperitoneal, subcutaneous, intramuscular, intratumoral or intradermal), inhalation, transdermal application, rectal administration, or oral administration.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, 17th ed., 1989).

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified. In some cases, the nanoonions are formulated with a pharmaceutically acceptable carrier prior to administration. Pharmaceutically acceptable carriers are determined in part by the particular composition being administered (e.g., nucleic acid or polypeptide), as well as by the particular method used to administer the composition. Accordingly, there are a wide variety of suitable formulations of pharmaceutical compositions of the present invention (see, e.g., *Remington's Pharmaceutical Sciences*, $17^{th}$ ed., 1989).

The dose administered to a patient, in the context of the present invention should be sufficient to effect a beneficial therapeutic response in the patient over time. The dose will be determined by the efficacy of the particular multi-wall carbon nanomaterial (e.g. nanotube or nanoonion) employed and the condition of the patient, as well as the body weight or surface area of the patient to be treated. The size of the dose also will be determined by the existence, nature, and extent of any adverse side-effects that accompany the administration of a particular peptide or nucleic acid in a particular patient, such as the increase in gene expression of proteins involved in inflammatory responses as shown in the Tables.

In determining the effective amount of the multi-wall carbon nanomaterial to be administered in the treatment or prophylaxis of diseases or disorder associated with the disease, the physician evaluates circulating plasma levels of the multi-wall carbon nanomaterial, multi-wall carbon nanomaterial toxicities, progression of the disease (e.g., ovarian cancer), and the production of antibodies that specifically bind to the multi-wall carbon nanomaterial. Typically, the dose equivalent of a polypeptide is from about 0.1 to about 50 mg per kg, preferably from about 1 to about 25 mg per kg, most preferably from about 1 to about 20 mg per kg body weight. In general, the dose equivalent of a naked c acid is from about 1 μg to about 100 μg for a typical 70 kilogram patient, and doses of vectors which include a viral particle are calculated to yield an equivalent amount of therapeutic nucleic acid. Dosages of multi-wall carbon nanomaterials administered to a patient can be based upon these dose equivalents for other therapeutics.

Doses of 0.6 mg/L and 6 mg/L for MWCNO, and doses of 0.06 mg/ml and 0.6 mg/L for MWCNT, were provided to cells in vitro such that the cells showed approximately 2 fold increase in apoptosis/necrosis from the untreated baseline cells, and a ~50% reduction in proliferation (measured by end point cell numbers) after a treatment of 48 hours at the low dose. The 2 fold increase of apoptosis/necrosis from the baseline was an artificially defined point. However, based on the size and toxicity measurements made in the in vitro studies described in the Examples, it is contemplated that a different scheme of dosing may be required. For example, it may be that doses of 0.01 mg/ml to 10 mg/ml to 100 mg/ml per kg body weight may be required. Appropriate animal and clinical studies to test the correct dosages and efficacy of the multi-wall carbon nanomaterials should be performed. Furthermore, multi-wall nanomaterials that are coated or contain surface modifications as contemplated, should have attenuated cellular responses to toxicity, stress and damage. Using the Tables showing Determination of a therapeutically effective amount is also affected by the number and percentage of genes showing statistically significant changes in overexpression and underexpression after cytotoxic dose and exposure to the multiwall carbon nanomaterials. In a preferred embodiment, the dosage of the multiwall carbon nanomaterials delivered should not effect more than a 2%, 5%, 7%, 10%, 15%, 20%, 25%, 40%, or 50% change in overexpression or underexpression of a specific gene, or overall in a gene functional family after cytotoxic dose and exposure. See Tables 1-7 and Tables 8-21.

For administration, multi-wall carbon nanomaterial of the present invention can be administered at a rate determined by the LD-50 of the multi-wall carbon nanomaterial, and the side-effects of the multi-wall carbon nanomaterial at various concentrations, as applied to the mass and overall health of the patient. Administration can be accomplished via single or divided doses, e.g., doses administered on a regular basis (e.g., daily or weekly) for a period of time (e.g., 2, 3, 4, 5, 6, days or 1-3 weeks or more). The multi-wall carbon nanomaterials of the invention are cytotoxic and slowly release each layer of the carbon nanomaterial, therefore, doses may be spaced out according to the release time determined for each dosage delivered.

In certain circumstances it will be desirable to deliver the pharmaceutical compositions comprising the multi-wall carbon nanomaterial of the present invention parenterally, intravenously, intramuscularly, or even intraperitoneally. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

Combination Therapy.

In some embodiments, the multi-wall carbon nanomaterials are administered in combination with a second therapeutic agent for treating or preventing cancer. In one embodiment, multi-wall carbon nanomaterials may be administered in conjunction with a second therapeutic agent, such as radiation or chemotherapy, for treating or preventing any cancer. For example, multi-wall carbon nanomaterials may be administered in conjunction with any of the standard treatments for ovarian cancer including, but not limited to, paclitaxel, cisplatin, carboplatin, chemotherapy, and radiation treatment.

The multi-wall carbon nanomaterials and the second therapeutic agent may be administered simultaneously or sequentially. For example, the multi-wall carbon nanomaterials may be administered first, followed by the second therapeutic agent. Alternatively, the second therapeutic agent may be administered first, followed by the multi-wall carbon nanomaterials. In some cases, the multi-wall carbon nanomaterials and the second therapeutic agent are administered in the same formulation. In other cases the multi-wall carbon nanomaterials and the second therapeutic agent are administered in different formulations. When the multi-wall carbon nanomaterials and the second therapeutic agent are administered in different formulations, their administration may be simultaneous or sequential.

In some cases, the multi-wall carbon nanomaterials can be used to target therapeutic agents to cells and tissues expressing any candidate genes that are related to reduced survival rate.

Therapeutic Kits.

The present invention further provides kits for therapeutic uses. Thus, the subject composition of the present invention may be provided, usually in a lyophilized form, in a container. The multi-wall carbon nanomaterials described herein are included in the kits with instructions for use, and optionally with buffers, stabilizers, biocides, and inert proteins. Generally, these optional materials will be present at less than about 5% by weight, based on the amount of multi-wall carbon nanomaterials, and will usually be present in a total amount of at least about 0.001% by weight, based on the multi-wall carbon nanomaterials concentration. It may be desirable to include an inert extender or excipient to dilute the active ingredients, where the excipient may be present in from about 1 to 99% weight of the total composition. The kits may further comprise a second therapeutic agent, e.g., paclitaxel, carboplatin, a chemotherapeutic agent.

Example 1

Materials and Methods of Measuring Toxicology of MWCNOs and MWCNTs

The carbon MWCNOs used in this study were produced by using a modified direct-current electric-arc discharge method based on the methods described by Sano, N., Wang, H., Chhowalla, M., Alexandrou, I. & Amaratunga, G. A. J. Nanotechnology: Synthesis of carbon 'onions' in water. Nature (London) 414, 506-507 (2001), hereby incorporated by reference. (See FIG. 1 and infra). The multi-walled carbon nanotubes (MWCNTs) were synthesized by using a chemical vapor deposition (CVD) method as described in Andrews, R., Jacques, D., Qian, D. & Rantell, T. Multiwall carbon nanotubes: synthesis and application. Acc Chem Res 35, 1008-1017 (2002), hereby incorporated by reference. See FIG. 1. Cellomics-based High Content Image Analysis (HCA) has been used for phenotypical measurement of cell apoptosis, necrosis, cell numbers, proliferation, and cell cycle distribution. Apoptotic cells and necrotic cells were detected using DNA dyes that only traverse membranes of necrotic or apoptotic cells (Wronski, R., Golob, N., Grygar, E. & Windisch, M. Two-color, fluorescence-based microplate assay for apoptosis detection. Biotechniques 32, 666-668 (2002)). The DNA stain, YO-PRO-1 can transverse the slightly permeable membranes of apoptotic cells while propidium iodide requires the greater membrane permeability of necrotic cells. An Affymetrix High-Throughput Analysis (HTA) automated GeneChip system was used for acquisition of the microarray data for the gene expression profiling. Target preparation, washing, and staining have been carried on an Affymetrix/Caliper robotic system, and scanning was performed on a CCD-based Affymetrix High Throughput (HT) scanner, which is a fully automated epiflourescent imaging system. More details can for the HTA protocols can be found in the Supplement. Data analysis has been performed using GeneSpring, Bioconductor, GeneTraffic, Cluster 3.0, PAINT, GoMiner, and PathwayAssist, with more details below.

Synthesis of MWCNOs.

The carbon MWCNOs used in this study were produced by using a modified direct-current electric-arc discharge method. Three liters of deionized Milli-Q (Millipore) water were degassed by vigorous magnetic stirring under vacuum for at least 1 hour. Then the water was cooled in an ice bath. Two graphite rods with a purity of 99.99% were used as electrodes. A 5-mm diameter rod was connected to the positive output of a power supply (DUAL MIG 151 T/2, Chicago, USA), and a section of a 12-mm rod was connected to the negative output and placed in a fixed position at the bottom of the water container. The two electrodes were submerged in the deionized water, and placed in fixed positions near the bottom of the water container. Helium gas was bubbled through the water at a rate of about 0.3 $Lmin^{-1}$ to obtain an inert atmosphere. A plastic film was used to seal the mouth of the water container. The anode was gradually moved towards the cathode until the arc initiated, and the arc was maintained by continuously adjusting the anode-cathode distance. During the discharge period, the voltage and current were maintained at about 10 V and 20 A respectively, and the temperature of the water was kept below 50° C. After the completion of discharge, the mixture of water and products was allowed to stand for about 15 minutes, and the suspended materials were collected on a cellulose membrane filter with a pore size of 100 nm, and air-dried at room temperature for use.

Synthesis of Multi-Walled Carbon Nanotubes (MWCNTs).

The multi-walled carbon nanotubes (MWCNTs) were synthesized by using a chemical vapor deposition (CVD) method. Ferrocene (sublimation temperature, ~140° C.) was chosen to produce Fe catalyst particles to seed nanotube growth. Xylene was selected as a hydrocarbon source because it has a boiling point of 140° C., well below the decomposition temperature of ferrocene (~190° C.). Approximately 6.5 mol % of ferrocene was dissolved in xylene to obtain a feed solution with ~0.75% Fe/C ratio, and the liquid was fed continuously into a two-stage tubular quartz reactor (diameter, ~34 mm) using a syringe pump. The liquid feed is passed through a capillary tube and preheated to ~175° C. prior to entering into the furnace. At this temperature, the liquid exiting the capillary is immediately volatilized and swept into the reaction zone of the furnace by a flow of argon with 10% hydrogen. After the reaction, the preheater and the furnace were allowed to cool to room temperature in flowing argon. MWCNOs formed on the walls of the quartz furnace tube and on plain quartz substrates were collected. At all times, the reactor was operated at 1" of $H_2O$ pressure above atmospheric pressure to prevent any influx of oxygen.

Cellomics.

Normal skin fibroblasts (HSF42) cells, cultured in alpha-MEM (Life Technologies, Inc., Grand Island, N.Y.) plus 10% fetal bovine serum, were plated at 5,000 cells/well in 96-well tissue culture plates (BD Biosciences) and treated with MWCNOs and MWCNTs, which were added to cell media at 0.6 µg/ml and 6 µg/ml (MWCNO), and 0.06 µg/ml and 0.6 µg/ml (MWCNT), with cells were exposed for 48 hours. Ethanol alone was used as a control at the same volume. Cell cycle measurements were performed as previously reported with some modifications[3]. Briefly, BrdU was added to the cells in media at a final concentration of 10 µM for 1 hour, cells were then fixed with 70% ethanol and put at 4° C. overnight. Staining was performed using anti-BrdU (cat. 555627 BD Bioscience) at a 1:100 dilution and a secondary rabbit anti-mouse AlexaFluor 488 (cat. A-11059 Molecular Probes) diluted 1:500, both in PBS/0.5% tween-20. Propidium iodide, 0.5 µg/ml, was used as a second stain to obtain DNA content information. Stained culture plates were scanned/analyzed on a Cellomics High Content Imaging system (Cellomics, KineticScan). The KineticScan is an automated imaging instrument that scans through the bottom of clear-bottom 96-well plates, focuses on a field of cells, and acquires images at each selected fluorescence channel. The Cellomics software (Cell Health Profiling) identifies and measures individual features and structures within each cell in a field of cells, so that up to thousands of individual cells can be analyzed in parallel. Intensity measurements for BrdU antibody staining and DNA staining with propidium iodide were obtained for each identified cell and these measurements were plotted by scatter plot, to obtain percentage of cells in G0/G1, S, and G2/M phases. Approximately 20,000 cells were plotted per treatment. A student t-test was performed to assess the significance of differences between treated and control cells.

The number of apoptotic and necrotic cells were also measured 48 hours after treatment. Apoptotic cells and necrotic cells were detected using DNA dyes that only traverse membranes of necrotic or apoptotic cells. The DNA stain, YO-PRO-1 (Molecular Probes, Y3603) is a dye that can transverse the slightly permeable membranes of apoptotic cells while propidium iodide requires the greater membrane permeability of necrotic cells. Live cells were exposed to these dyes for 30 minutes and then immediately analyzed on the KineticScan where the intensities of these dyes were measured for each cell. Greater intensities are measured with increasing membrane permeability. The Cellomics software (Cell Health Profiling) was used to quantify these intensities and then these were averaged for all the measured cells. Eight wells were done per condition and the results from these analyses were used in a t-test to assess if the treated group showed significantly different staining from the control group.

Cell Culture and RNA Isolation.

Cell cultures of HSF42 cells were incubated at 37° C. in humidified 5% $CO_2$. Plates were harvested 24 hrs after treatment. One T75 flask was used for each treatment, and each treatment was performed in triplicate. Cells were homogenized in TRIZOL reagent (Gibco BRL) for the isolation of total RNA following the manufacturer's instructions. The TRIZOL-isolated RNA were further purified with RNeasy kit (Qiagen) and resuspended in DEPC-treated water (SIGMA-Aldrich).

Microarray Hybridization and Data Acquisition: Target Preparation.

The target preparation protocol of the GeneChip® assay (Affymetrix, Santa Clara, Calif.) were broken down into sections of methods and adapted to the robotic station as follows: For each sample, the RNA target is prepared by putting 2.5 µg of total RNA in 5 µl water and 5 µl of 10 µM T7 (dt)24 primer into a 96-well reaction plate (MJ Research, Waltham, Mass.). The total RNA undergoes an annealing step at 70° C. for 10 minutes followed by a 4° C. cooling step for 5 minutes. The plate is transferred back to the deck position and undergoes first strand cDNA synthesis. 10 µl of First Strand cDNA Synthesis cocktail (4 µl of Affymetrix 5×$1^{st}$ strand buffer (250 mM Tris-HCl, pH 8.3 at room temperature; 375 mM KCl; 15 mM $MgCl_2$), is mixed with 2 µl 0.1M DTT, 1 µl 10 mM dNTP mix, 1 µl Superscript II (200 U/ul), and 2 µl nuclease free water per reaction) is added, and the plate is then transferred to the thermal cycler and incubated at 42° C. for 60 minutes and 4° C. for 5 min. 91 µl of nuclease free water and 39 µl of the Second Strand cDNA Synthesis cocktail (30 µl of Affymetrix 5×$2^{nd}$ strand buffer, 100 mM Tris-HCl (pH 6.9), 23 mM $MgCl_2$, 450 mM KCl, 0.75 mM 13-NAD, 50 mM $(NH4)_2SO4$); 3 µl 10 mM dNTP; 1 µl 10 unit/µl DNA Ligase; 4 µl 10 unit/µl DNA Polymerase and 1 µl 2 units/µl RNase H) is added. The plate is cycled at 16° C. for 120 minutes and 4° C. for 5 minutes. 4 µl of T4 Polymerase cocktail comprised of 2 µl T4 DNA Polymerase plus 2 µl 1×T4 DNA Polymerase Buffer (165 mM Tris-acetate (pH 7.9), 330 mM Sodium-acetate, 50 mM Magnesium-acetate, 5 mM DTT) is added and the plate is taken back to the thermal cycler where it is cycled at 16° C. for 10 minutes, 72° C. for 10 minutes, and cooled to 4° C. for 5 minutes.

The plate is transferred back to the deck and Agencourt Magnetic Beads (Beverly, Mass.) are used for the cDNA clean-up. 162 µl of magnetic beads are mixed with 90 µl of in the cDNA Clean-Up Plate and incubated for 5 minute. Post incubation, the cDNA bound to the beads in the cDNA Clean-Up Plate is moved to the Agencourt magnetic plate. Another 115 µl of magnetic beads is mixed with 64 µl cDNA incubated for 5 minutes, and then moved to the Agencourt magnetic plate. Post incubation, the supernatant is removed and two washes with 75% EtOH are performed using 200 µl solution. The EtOH is then removed and the beads sit for 5 minutes. 40 µl of nuclease free water is added to the beads and mixed well. The solution is then incubated for 1 minute, and then it is taken back to the magnetic plate where it is incubated for 5 minutes to capture the beads on the magnet. 22 µl of eluted cDNA is then transferred to the Purified cDNA Plate (22 µl total volume).

38 µl of IVT cocktail (6 µl 10× IVT Buffer, 18 µl HTA RLR Reagent (labeling NTP), 6 µl HTA Enzyme Mix, 1 µl T7 RNA Polymerase, and 7 µl RNase free water per reaction) is added to the purified cDNA) is added to the 22 µl of purified cDNA (60 µl total volume). The plate is then transferred to the thermal cycler where incubation of 8 hours at 37° C. occurs. Upon completion, the plate is transferred back to the deck where 120 µL Agencourt Magnetic Beads are used to clean up the cRNA product.

The purified cRNA is taken to the spectrophotometer and read concentration in each of well of a 96 well plate is adjusted to a nominal value of 0.625 μg/μl. A second reading is taken to verify the normalization process. 30 μl of cRNA was transferred from the cRNA Normalization Plate and dispensed in the Fragmented cRNA Plate. 7.5 μl of 5× fragmentation buffer per sample is added. The plate is then transferred to the thermal cycler where it is cycled at 94° C. for 35 minutes followed by a cooling step at 40° C. for 5 minutes. The sample is then mixed with 90 μl of hybridization cocktail (3 μl of 20× bioB, bioC, bioD, and creX hybridization controls mixed with 1.6 μl 3 nM oligo-B2, 1 μl 10 mg/ml Herring sperm DNA, 1 μl 50 mg/ml acetylated BSA, and 83.4 μl 1.2× Hybridization Buffer).

Hybridization.

The sample is then ready to be hybridized. The peg array plate is incubated in 60 μl pre-hybridization cocktail (1 μl 10 mg/ml Herring sperm DNA, 1 μl 150 mg/ml Acetylated BSA, 84 μl Hybridization buffer, 15 μl nuclease free $H_2O$ per reaction). The hybridization-ready sample is taken to the thermal cycler and denatured for 95° C. for 5 minutes. Upon completion of this step, the plate is returned to the deck where 70 μl of sample is transferred to a hybridization tray. The peg plate is then lifted off of the pre-hybridization tray and taken to the hybridization plate where it is placed. This "hybridization sandwich" is then manually transferred to a hybridization oven where it incubates at 48° C. for 16-18 hours.

Wash/Stain.

The robot will lift the peg plate off the hybridization tray and take it to the first low stringency wash (LSW) (6×SSPE, 0.01% Tween-20) where it will dip-wash 36 times. The plate will then go to the other three low stringency wash positions where the dipping is repeated. The peg plate is then moved to the high stringency wash (HSW) (100 mM MES, 0.1M NaCl, 0.01% Tween-20) where it will incubate at 41° C. for 25 minutes. After the incubation, the peg plate will be taken to a fifth LSW tray where it will rinse off the HSW.

The plate is then transferred to the first stain (31.5 μl nuclease free $H_2O$, 35 μl 2×MES stain buffer, 2.8 μl 50 mg/ml Acetylated BSA, 0.7 μl R-Phycoerythrin Streptavidin), where it will incubate at room temperature for 10 minutes. At the end of the 10 minute incubation, the peg plate undergoes another 4 cycles of dip washing method. The peg tray is then transferred to stain 2 (2.8 μl 50 mg/ml Acetylated BSA, 0.7 μl reagent grade goat IgG, 0.4 μl biotinylated goat Anti-streptavidin antibody per reaction).

The above method will repeat for stain 3 (31.5 μl nuclease free $H_2O$, 35 μl 2×MES stain buffer, 2.8 μl 50 mg/ml Acetylated BSA, 0.7 μl R-Phycoerythrin Streptavidin). At the end of the incubation of the third stain, the peg plate will be washed 36 times in LSW. The robot will then take 70 μl of MES holding buffer, 68 mM MES, 0.1M NaCl, 0.01% Tween-20, and put into a sterile scan tray. The peg tray is then placed into the scan tray and is ready to be scanned.

Scanning.

The 96 well peg plate is scanned by the Affymetrix High Throughput (HT), which is a fully automated epiflourescent imaging system with an excitation wavelength range of 340 nm to 675 nm and a cooled 1280×1024 CCD camera with 12 bit readout and resolutions of 1.0 μm/pixel with the 10× objective. The images are captured at two different exposure times. Each well will have 49 sub-images/exposure time. The software program then convert these .dat files into mini .cel files and then into composite cel files where the information can be analyzed in the Affymetrix GCOS 1.2 software.

Data Processing.

The .cel files were autoloaded into GeneSpring (Agilent Technologies). Per-chip normalization was performed using robust multi-array average (RMA) method, which generates background-adjusted, normalized and log-transformed perfect-match probe values[5, 6]. We used Bioconductor to perform significance analysis to determine the difference between expression levels in treated sample and control sample possesses statistical significance. The empirical Bayesian model was used with Bonferroni's multi-test correction. The cutoff of p-values produced through the analysis was determined by at least 10 times less than the p-values of the smallest p-value of control probe sets on the chip.

Significance Analysis of Gene Functional Groups.

We used GoMiner, a program developed in NIH and Georgia Tech/Emory University, to perform this analysis, Zeeberg, B. R. et al. GoMiner: a resource for biological interpretation of genomic and proteomic data. Genome Biol 4, R28 (2003). First of all, gene ontology terms of all genes on the chip were retrieved. The relative enrichment of changed genes in certain GO category was calculated as follows:

$$R_e = (n_f/n)/(N_f/N)$$

Where $n_f$ is the number of changed genes in the category; n is the total number of genes on the chip that belong to the category; $N_f$ is the number of changed genes on chip; N is the total number of genes on chip.

For each category, p-value was calculated by conducting two-sided Fisher's exact test, which reflects the statistical significance for that category being enriched in changed genes. The p-values were used to sort categories to identify those gene functional groups that have responded the most after treatments.

Promoter Analysis.

The upstream promoter region of the up- or down-regulated genes are analyzed with PAINT developed at Thomas Jefferson University (Vadigepalli, R., Chakravarthula, P., Zak, D. E., Schwaber, J. S. & Gonye, G. E. PAINT: a promoter analysis and interaction network generation tool for gene regulatory network identification. Omics 7, 235-252 (2003)). 5000 bp upstream sequences for significantly changed genes from the previous analysis were collected. The software then searched these sequences for vertebrate Transcription Regulatory Elements (TRE) to build individual interaction matrices for the individual gene lists (parameters:TRE motif finding algorithm: Match, TRANSFAC Professional—U.S.A) (Matys, V. et al. TRANSFAC: transcriptional regulation, from patterns to profiles. Nucleic Acids Res 31, 374-378 (2003)); TRE Core Similarity threshold=1.00; including TREs found on complementary strand). The software then computes p-values to look for the overrepresented TREs in the set of promoters analyzed in reference to all the genes in the PAINT database to generate filtered (p-value value<0.1) interaction matrices. The hierarchical clustering was conducted using Cluster 3.0, a modified version developed at Tokyo University, based on Michael Eisen's original software (Eisen, M. B., Spellman, P. T., Brown, P. O. & Botstein, D. Cluster analysis and display of genome-wide expression patterns. Proc Natl Acad Sci USA 95, 14863-14868 (1998)). The analysis was performed with complete linkage using similarity matrix of centered correlation.

Example 2

Evaluating Toxicity in Nanomaterial Exposed Cells

In this study, the goal was to assess if changes in gene expression in cells exposed to carbon-based nanomaterials shows a correlation to phenotypic observations. Reported here are two approaches to evaluate toxicity in nanomaterial exposed cells; (i) the measurement of phenotypic changes in large populations of cells by high content analysis and (ii) gene expression array analysis in exposed cells. Phenotypically, cells exposed to high concentrations of nanomaterials were observed to undergo apoptosis/necrosis with a concomitant reduction in proliferation indicative of an inflammation response. We found that carbon nanomaterials, generated mRNA level changes in exposed skin fibroblasts, including changes in mRNA levels from genes involved in metabolism, apoptosis, cell cycle, stress response, cellular transport, and inflammatory response. Of interest was our observation that many of the genes that increased in expression in nanomaterial-exposed cells are often associated with a type I interferon response, which are known to be activated during viral infection and lead to antiviral and anti-proliferative responses. Promoter analysis, derived from gene expression data, indicates that the primary mechanism for cell effects from MWCNO and MWCNT treatment is through the p38/ERK MAPK kinase and interferon response pathways. Of interest is the observation that MWCNTs appear to induce a greater amount of stress upon the cells than MWCNOs, even though the dosage is $1/10^{th}$ by weight/volume concentration. This may have far reaching ramification for the deployment of specific types of nanomaterials in the future. Clearly this study underscores the importance of the potential toxic side effects in this burgeoning field.

In Vitro Toxicity.

Figure 3:
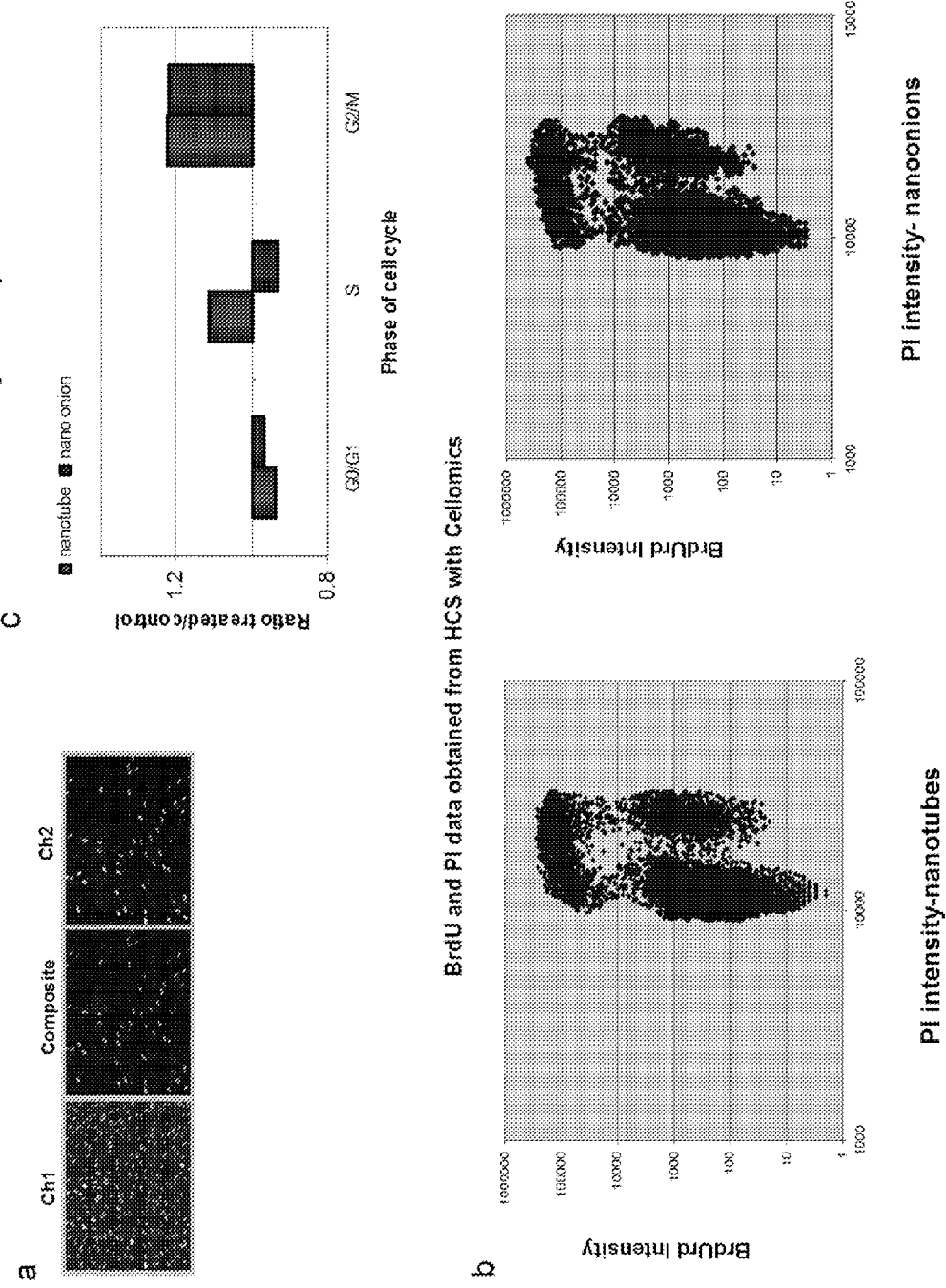
FIG. 3. Measurement of cell proliferation after treatment with carbon nanomaterials at cytotoxic doses. Cells were plated on 96-well plates, treated, pulsed with BrdU, fixed, and then stained with anti-BrdU and PI. Plates were transported to the KSR for image collection and then automated analysis was performed on the collected images. A. Images generated by the KSR. Channel 1 is images of PI stained nuclei, and this is used for cell identification, counting, and DNA content. Channel 2 represents BrdU staining and this shows cells that have pass through S-phase during the pulse with BrdU. The composite image is also shown. B. Typical scatter plot of BrdU staining intensity versus PI intensity. This is used for calculating the number of cells in G0/G1, S, and G2/M phases. C. Summary of cell cycle data for nanomaterial-treated cells as compared to controls. An average of 20,000 cells was measured for each treatment condition.
Figures 1, 5A:
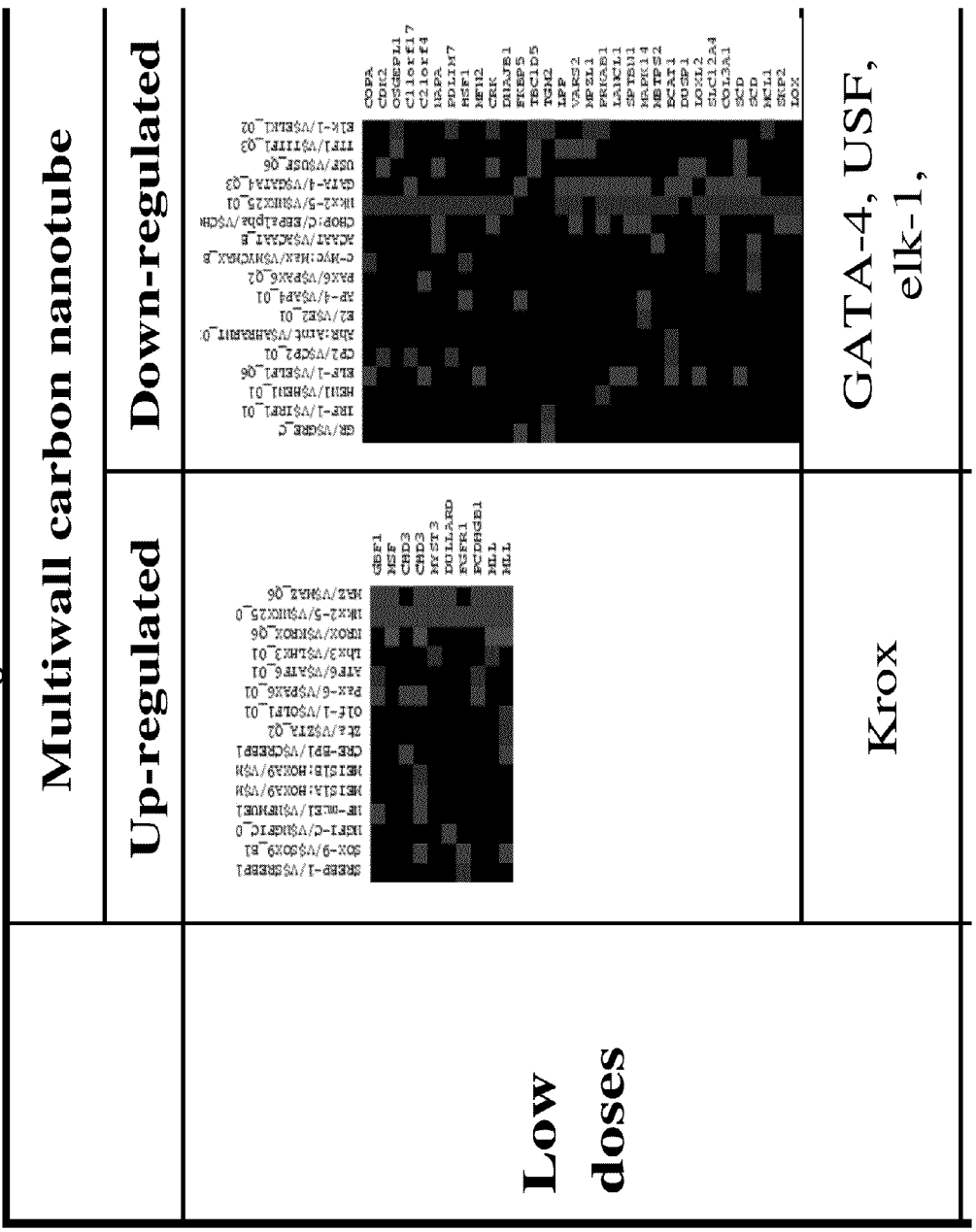
Figures 2, 5A:
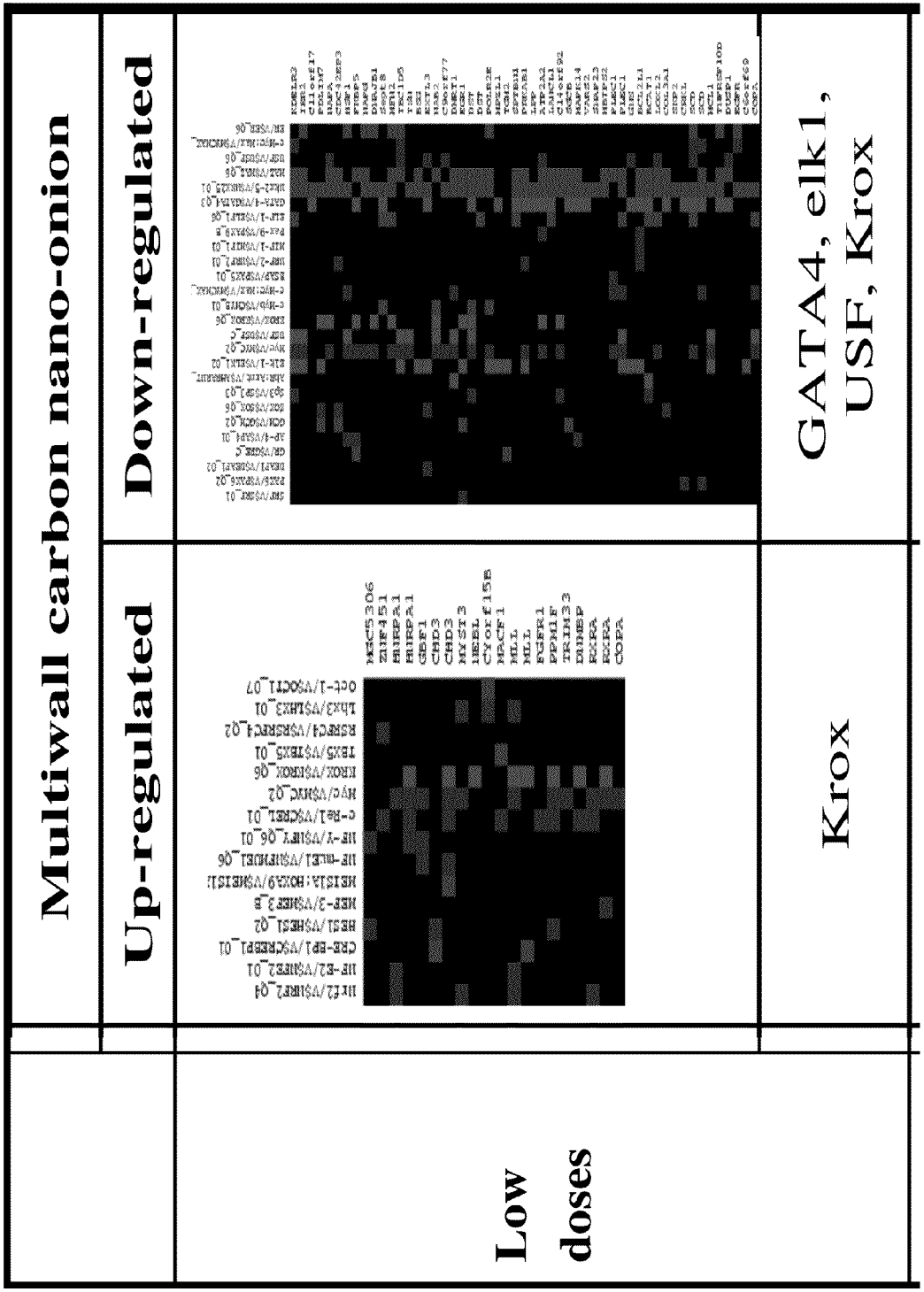
FIG. 2. Cell viability measurements after treatment with carbon nanomaterials at cytotoxic doses. A. The number of skin fibroblast cells per well 48 hours after mock treatment with ethanol or treatment with either MWCNOs (NO) or nanotubes (NT). The numbers of low doses (0.6 µg/mL for MWCNO and 0.06 µg/mL for MWCNT), and high doses (6 µg/mL for MWCNO and 0.6 µg/mL for MWCNT) represent the nanomaterials concentration used for treatment. Bars represent the mean of cell numbers from 10 imaged viewfields in 10 treated wells and error bars represent a 95% confidence interval. Each nuclei imaged by the KSR was identified with the Cell Health Profiling software in the blue channel by Hoechst staining. B and C. YO-PRO1 is visualized in the green channel and PI is visualized in the red channel, where measurement such as dye intensity and area can be made using the Cell Health Profiling algorithm. D. Average intensity of YO-PRO1 intensity and PI intensity of mock treated and treated skin fibroblasts at 48 hours. The YO-PRO1 intensity is proportional to apoptosis and the PI intensity correlates to necrosis. Bars represent the mean of cell numbers from eight treated wells and the error bars represent a 95% confidence interval. Data for lung fibroblast treated under the same condition is presented in FIG. 7.

Human skin fibroblasts (HSF42) (FIGS. 2, 3) and human embryonic lung fibroblasts (IMR-90) (FIG. 7), both untransformed cells, were used to evaluate the cytotoxic and proliferative effects of carbon nanomaterials. Lung and skin cells were selected because entry through the skin or respiratory tract is the most likely route of exposure to nanomaterials. Referring now to FIG. 2, cells were added to 96-well plates (BD Biosciences), grown to approximately 70% confluency in a $CO_2$ incubator and then exposed to several concentrations of MWCNOs and MWCNTs (FIG. 1). To determine the cytotoxic dose to be used for this study, cells were treated with serial dilutions of MWCNO and MWCNT (data not shown), and we chose doses of 0.6 mg/L and 6 mg/L for MWCNO, and doses of 0.06 mg/ml and 0.6 mg/L for MWCNT, so that the cells show approximately 2 fold increase in apoptosis/necrosis from the untreated baseline cells, and a ~50% reduction in proliferation (measured by end point cell numbers) after a treatment of 48 hours at the low dose. The 2 fold increase of apoptosis/necrosis from the baseline is an artificially defined point, an approach previously used in Ding, L. H. et al. Gene expression profiles of normal human fibroblasts after exposure to ionizing radiation: a comparative study of low and high doses. *Radiat Res* 164, 17-26 (2005). The high doses are chosen as 10 times of the low dose, so that pronounced gene expression changes can be observed to mimic the acute exposure to carbon nanomaterials. Cells were exposed for 24 or 48 hours, counted and various measurements were made to evaluate cytotoxicity and proliferation. The MWCNT seem to be ten times more toxic than the MWCNO, which is the reason that the amount of MWCNT used in our studies is only one tenth of the amount of MWCNO used, at both the low dose and high dose levels.

Cell counts were obtained by staining live cells with Hoechst 33342 (Sigma), 48 hours post treatment and then using high content imaging in the KineticScan (KSR, Cellomics, Pittsburg) to visualize the cells. Hoechst, will stain DNA in both live and dead cells, however the intensity of staining is higher in apoptotic cells because of the condensed chromosomes. The image analysis software, Cell Health Profiling (Cellomics) was then used with the images obtained with the KSR to identify and count cells. The bars in the graphs in FIG. 2A and FIG. 7 show cell numbers. This graph demonstrates that treatment with either the MWCNO(NO) or MWCNT (NT) reduces cell number in a dose-dependent fashion, with the higher concentrations of MWCNTs creating the greatest effect (FIG. 2). This reduction in cell number could result from apoptosis/necrosis and/or reduced proliferation.

Results.

Whole genome expression array analysis and high content image analysis-based phenotypic measurements were performed on human skin fibroblast cell populations exposed to multiwall carbon nano-onions (MWCNOs) and multiwall carbon nanotubes (MWCNTs). Here we demonstrate that exposing cells to MWCNOs and MWCNTs at cytotoxic doses induces cell cycle arrest and increases apoptosis/necrosis.

Gene expression changes in human skin fibroblasts serve as readout for cellular responses to the stimulus of carbon nanomaterials. By applying significance analysis with very conservative Bonferroni multi-testing correction, we found a profound number of genes with statistically significant expression level changes (FIG. 4, Tables 9-20). Treating cells at the high dose of carbon particles caused more gene expression changes than the low dose treatment (FIG. 4). However, it would be misleading to say that the responses were dose-dependent, at least for the two doses in this study. As shown in FIGS. 4B and 4C, only a small portion of genes with altered transcription were found in common between the low and high dose profiles, when treating with same type of particle. This indicates that distinct gene expression profiles were induced at low and high dose treatment. In contrast, if we compare two types of particles, they induced similar transcriptional changes in cells at the same doses (FIGS. 4D and 4E). The unique genes flanking the overlapping area in FIGS. 4D and 4E may indicate cellular responses unique to exposure with MWCNOs or MWCNTs (Tables 15, 17, 18, and 20).

Gene ontology analysis gave further evidence supporting the qualitative differences of cell responses to low and high doses of carbon nanomaterials. The percentages of over-expressed and under-expressed genes in the top 10 mostly changes gene categories were shown in Table 1. At low dose of both of MWCNO and MWCNT, genes were down-regulated in most of the categories. Many of these genes involve Golgi vesicle transport, secretory pathway, fatty acid biosynthesis, protein metabolism and G1/S transition of mitotic cell cycle. The only up-regulated category was protein ubiquitination (Table 1, Supplement Table 13). Collectively, this data suggests a reduction of cell growth and metabolism, but an acceleration of protein degradation at the low dosage. Reduction of cell growth was consistent with our phenotypic data. In contrast, a high dose of MWCNO and MWCNT resulted in the up-regulation of protein and amino acid metabolism; with additional up-regulation of genes involved in a type I IFN response (Table 1). The outcome is an increase in apoptosis and reduction in cell growth. However, the distinct gene expression profiles induced at low and high doses may indicate that different mechanisms are responsible for our phenotypic observations or that the response occurs at a different rate and we are observing two 'snap shots' of a temporal progression of a single mechanism. This observation agrees with the a previous study with gene expression changes induced by radiation and described in Ding, L. H. et al. Gene expression profiles of normal human fibroblasts after exposure to ionizing radiation: a comparative study of low and high doses. *Radiat Res* 164, 17-26 (2005).

Structure-specific cellular responses were also observed in this experiment. At high dose, only MWCNT caused over expression of a significant number of immune and inflammatory response genes (Table 1 and Table 2). Totally 25 genes in this category were over-expressed and only one gene was under-expressed, indicating a robust response of this function group (Table 1 and 2). Most of these genes are involved in innate immune response system and are induced by interferon, or interferon related proteins. Many of these genes are implicated in an interferon type I response, which is potently antiviral and anti-proliferative. Some of the genes that are typically induced by an interferon type I response include Irf7, Isgf3g, Stat1 Adar, Cxcl10, Irf1, Isgf3g, IFIT1, MX2, all found in Table 2. Interestingly the dimension of carbon tubes is similar to virus and the cellular response may mimic the response observed with viral infection. Certainly the induction of many of the same genes during viral infection is observed. Our observation fits previous report that keratinocytes (HEKs) exposed to chemically unmodified MWCNT released interleukin-8, a pro-inflammatory cytokine, which was postulated to result in the skin irritation associated with exposure[39].

In addition to the IFN type I response genes, we also observed up-regulation of intracellular aryl hydrocarbon (AHR) in MWCNT treated cells (Table 5). This gene is typically expressed in cells or animals exposed to polycyclic aromatic hydrocarbons and is believed to mediate the teratogenesis, immune suppression, epithelial disorders, and tumor production in exposed experimental animals. Transcription of Bax, driven by AHR, is part of an evolutionarily conserved cell-death signaling pathway response, responsible for ovarian failure induced by environmental toxins. Overexpression of this gene is consistent with the cell death we observed with the carbon nanomaterials. In addition, the cytokine and TNF family member, TNFRSF10B (TRAILR2) is up-regulated in cells treated with the highest concentration of nanotubes, and this protein induces apoptosis in a wide variety of cells. Additional apoptosis genes involved include BCL2L2 and MCL1. Finally, RIPK2 and TNFAIP3, genes that contribute to the induction of apoptosis, were also observed to be up-regulated in these treated cells.

Data from Tables 4 and 5 indicate that FGFR1 and EGFR are involved, in the response. We suspect that the cells are using strategies similar to a viral response when exposed to nanomaterials. Viruses are very similar in size range to the carbon nanomaterials used here, around 20 nm in diameter. FGFR, EGFR, and other RTK pathways have been implicated in viral response in numerous studies. An early step in viral infection is the targeting of the virus to cell surface receptors. Many viral receptors have been identified, including signaling receptors such as EGFR, chemokine receptor, platelet-derived growth factor receptor, fibroblast growth factor receptor, tumor necrosis factor receptor family and various integrin receptors. Usually multiple receptors are targeted by the virus for binding, signaling and entry. Virus also impinges upon the signal transduction pathway in the sense that their binding to the receptor perturbs the normal receptor-coupled signal transduction pathways. Many of receptors, e.g. EGFR, are potent stimulators of the mitogen-activated protein kinase (MAPK) signaling pathway. Chronic stimulation of EGFR and of multiple steps in the MAPK signaling pathway is involved in multiple cellular processes, especially in the interaction between viruses and tyrosine kinase pathways[91]. One interesting observation is the downregulation of EGFR by >4 fold, which indicate that the nano-onion and nanotubes might serve as therapeutics for EGFR-overexpressing epithelial cancers, such as >20% of the breast cancer. This could be a very interesting use of the cytotoxicity of the carbon nanomaterials. In addition to regulation of EGFR and FGFR1 expression, the over-expression of VEGF mRNA is also observed at both high dose experiments. The secretion of VEGF could be the cellular wound healing response to the addition of nano particles. In addition to it ability to activate epithelial proliferation, it may also be a last-resort cellular response to save the epithelial cells from apoptosis.

Figure 5B:
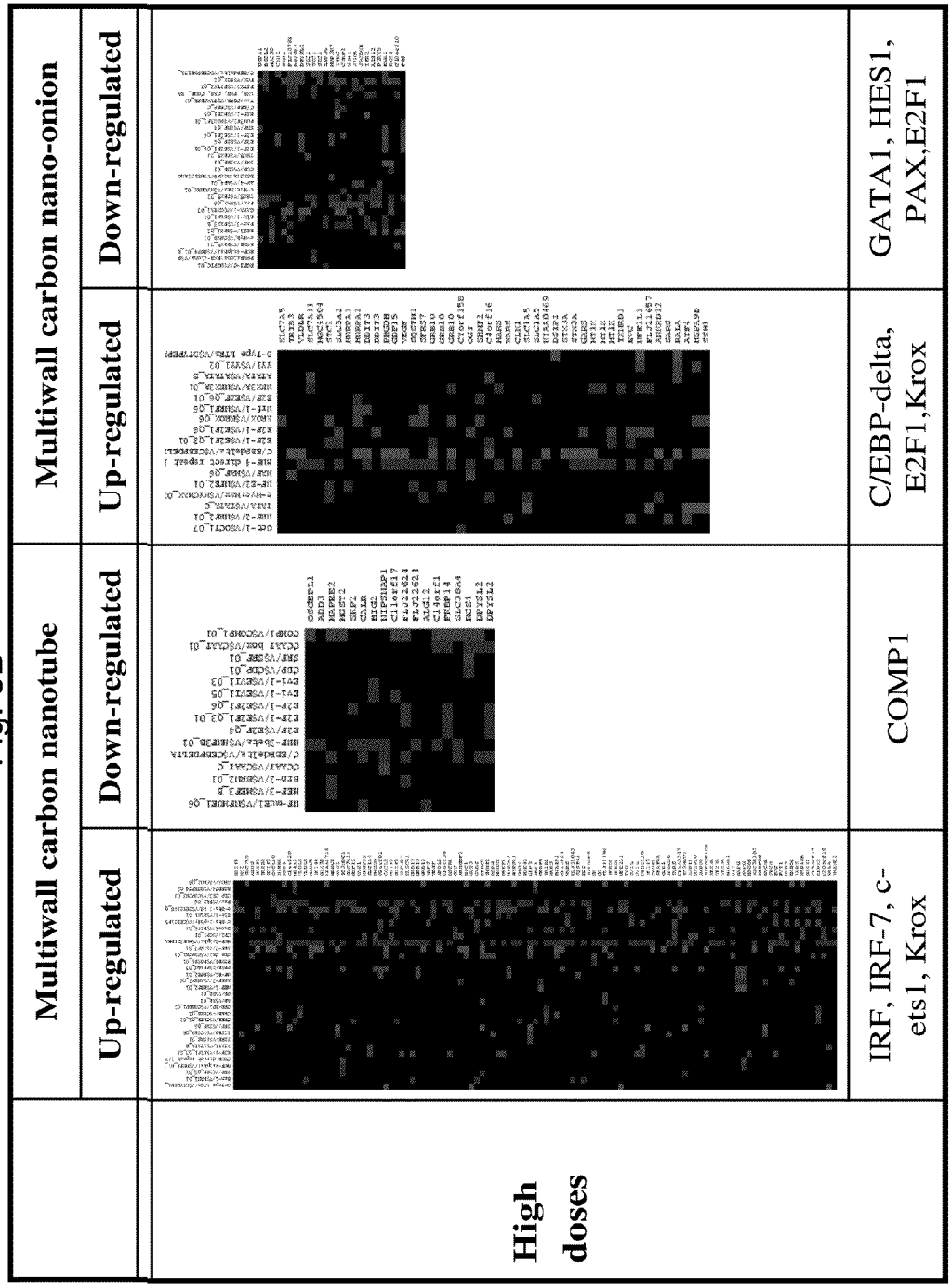
FIG. 5. Promoter analysis. The interaction matrix for the differentially expressed genes (horizontal) and transcription regulatory elements (vertical) in the up- and down-regulated gene sets at different dosage using different carbon nano-particles. Individual elements of the matrix are colored by the significance p-values: over-representation in the matrix is colored. The brightest spots represents a low p-value (most significantly over-represented). Enriched transcription regulatory elements for the nano-particle dataset are shown for low doses of carbon nano-particles (FIG. 5A) and for high doses (FIG. 5B).
Figure 6A:
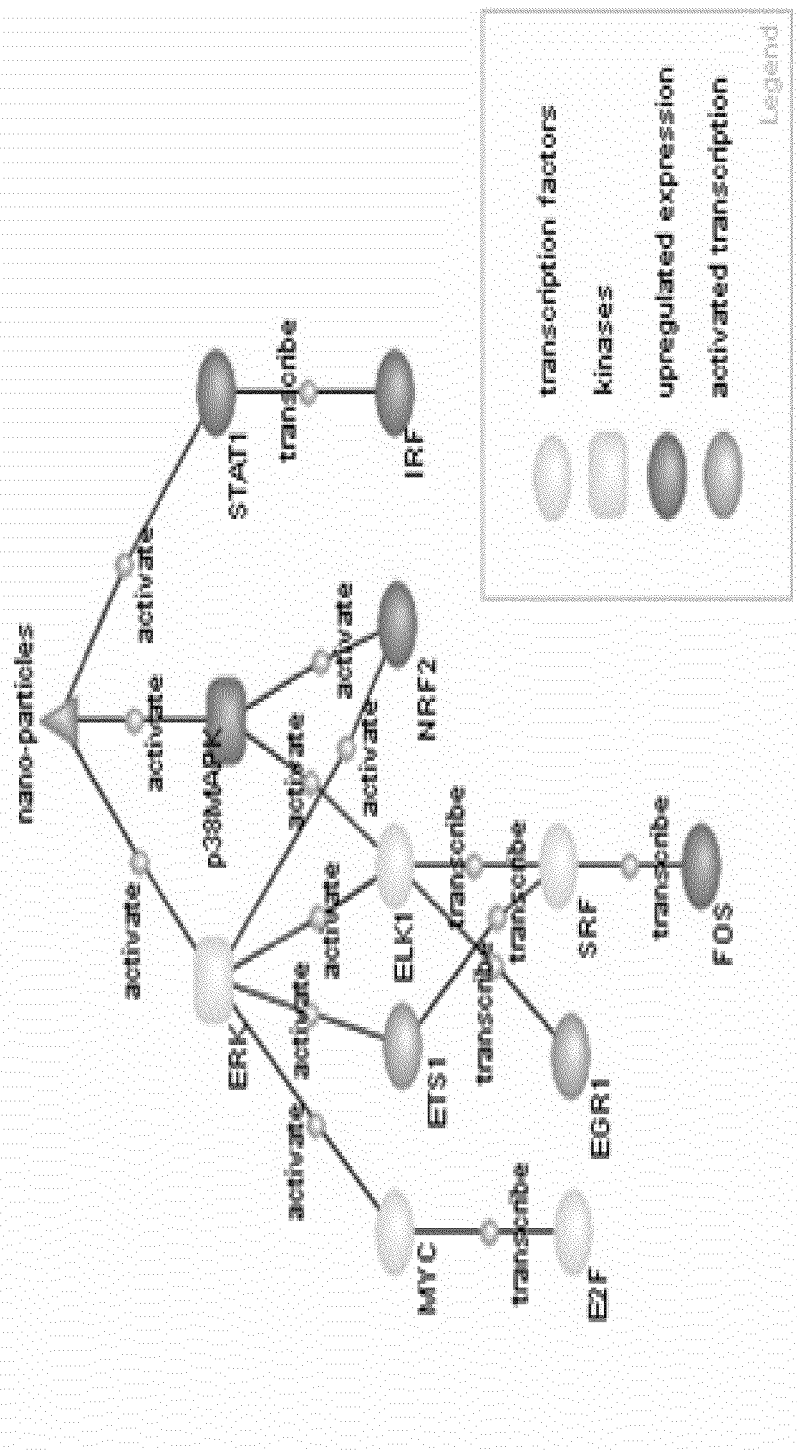
FIG. 6. A comparison of activated signal transduction networks for higher dose responses to carbon tubes and carbon onions. PathwayBuilder software (Arkin Group, LBNL) is used to analyze and create pathways differentially activated with the treatment matrix based on published literature.
Figure 6B:
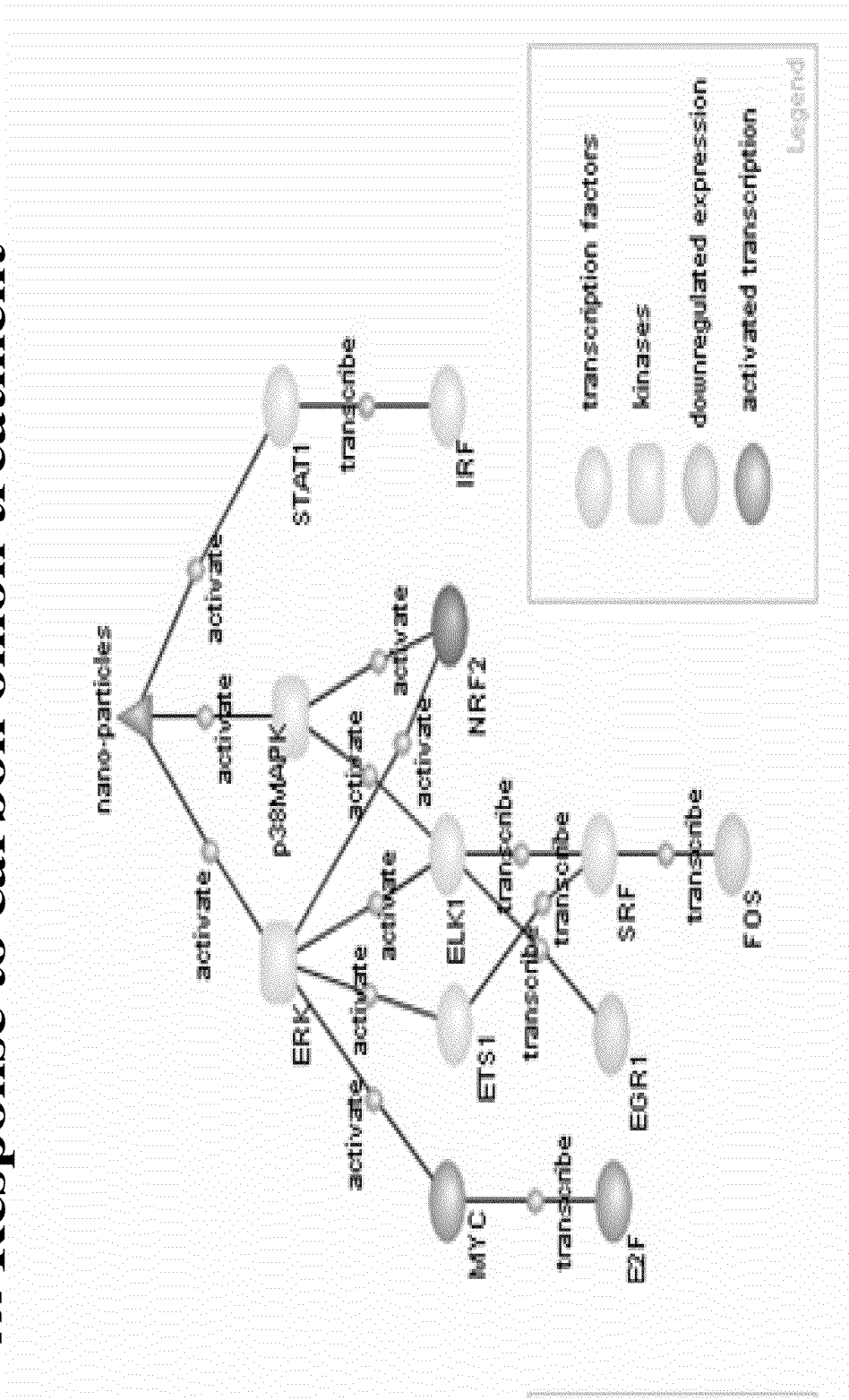

Promoter analysis identified Egr1/Krox as one of the over-represented transcription regulatory elements on up-regulated genes in almost all experimental settings (FIG. 5). In addition, with high dosage of treatment, additional transcription factors (ets1 and IRF for MWCNTs, e2f and C/EBP-delta for MWCNOs) might be involved (FIG. 5). In general, the profiles of enriched TREs are dramatically different in the individual experiments. For the down-regulated genes from MWCNT treatment, there are enrichment of GATA4, USF and elk1 at low dosage and COMP1 (cooperates with myogenic proteins 1) at higher dosage. For the carbon onions treatment, the lower dosage is correlated with enrichment of GATA4, USF, elk1 and Egr1/Knox in down-regulated genes and high dosage with enrichment of GATA1, HES1, PAX and E2F1. The upstream events leading to the different expression pattern seem to be related to ERK and p38 MAPK activities and the induction of interferon signaling. These analyses suggest that the induction of the p38/ERK pathway and the type I IFN response are the upstream signaling events (See FIG. 6 for the pathway analysis result illustration) responsible for changes in cellular transcription due to MWCNO and MWCNT treatment of cells. Indeed, the pathway responses shown here are similar to the response of human bronchial epithelial cells to combustion-derived metals.

Combined with the result from functional analysis, the examples clearly show that at high dosage, carbon particles can seriously impact the cellular functions in maintenance, growth and differentiation. Of these two nanomaterials, MWCNTs appears to induce more stress on the cells than MWCNOs. Our data suggest that there is a qualitative difference in response to low dose and high dose treatment of carbon particles in human skin fibroblasts. Carbon tubes at high dose induced innate immune responses, whereas Carbon onions did not. This indicates that cells respond differently according to the structures of nanomaterials. Our data also suggests that Carbon atoms released from nanomaterials may participate in cell metabolic pathways. It is evident from our studies that carbon nanomaterials have a toxic effect on lung and skin cells. As little as 15,000 MWCNOs per cell and a few dozen MWCNT per cell induced cell death in this study. Therefore, as this potentially revolutionary technology is further developed, specific heed must be given to minimizing unwanted effects upon both producers and consumers. The regulation of p38/ERK and the EGFR also provides for the use of carbon nano-onions and potentially other carbon nanomaterials to be exploited as a nanomedicine platform for cancer therapy, especially epithelially derived cancers.

Example 3

Evaluating Apoptosis and Necrosis in Nanomaterial Exposed Cells

Cytotoxicity was evaluated by staining live cells for 30 minutes with YO-PRO1 (Invitrogen, Molecular Probes), propidium iodide (PI, Sigma) and Hoechst. Live cells are impermeable to YO-PRO1 and PI, both of which are intercalating DNA dyes. Apoptotic cells are permeable to YO-PRO1, whilst PI only stains necrotic cells. Stained culture plates were analyzed using the KSR and images were acquired at each appropriate fluorescence channel for Hoechst, YO-PRO1, and PI. The image analysis software establishes average and total intensity for each nucleus in all channels. In the experiments pictured in FIG. 2, wells were either exposed to the indicated concentration of nanomaterials or the same volume of ethanol solvent as a control, both kept less than 1% of the total volume. Ten replicates were done for each condition with intensities for both YO-PRO1 and PI averaged by well, to obtain the bars in FIGS. 2B and 2C. Student t-tests indicated that all treatment groups demonstrated significant differences from the control group, with $p<0.01$.

The following observations were made: 1) Apoptosis and necrosis were observed for both MWCNO and MWCNT treated cells with MWCNTs having the most detrimental effect on both types of cells at the highest concentration (FIG. 2). 2) MWCNO treatment to lung fibroblasts, however, demonstrated less of an effect as compared to treatment of skin fibroblasts (FIG. 2 and FIG. 7). 3) Skin fibroblasts treated with the higher concentration of MWCNOs, demonstrated a cell count less than half of that observed in the control, more closely reflecting the results obtained with MWCNT treatment (FIG. 2). 4) The average intensity of YO-PRO1 and propidium iodide staining in the cell types treated with both MWCNOs and MWCNTs went up in a dose dependent manner (FIG. 2) with one exception. The exception is average YO-PRO1 staining in MWCNO treated skin fibroblasts, and it remains similar at both concentrations. The PI staining, however, gains intensity at the higher concentration of MWCNOs, indicating a greater number of necrotic cells. These observations indicate the induction of apoptosis and necrosis in nanomaterial-treated cells that is dose and material dependent. It cannot be ruled out that some of the reduction in cell number was a result of reduced proliferation so this was also tested.

Example 4

Cell Proliferation of Nanomaterial Exposed Cells

Proliferation was measured in skin fibroblasts by incorporating BrdU for 30 minutes, fixing cells, staining for BrdU with an antibody and then counterstaining the DNA with PI. FIG. 3A shows images from one field, generated by the KSR for image analysis, with PI staining pictured in channel 1, BrdU antibody staining in channel 2, and the composite is pictured in the middle. After images from stained culture plates were obtained using the KSR intensity measurements for both BrdU and DNA staining were made for each identified cell to generate a scatter plot with the intensity of BrdU antibody staining on the Y-axis and PI intensity on the X-axis. Analysis of these scatter plots allowed us to obtain percentages of cells in G0/G1, S, and G2/M phases during cell cycle (FIG. 3B). Data from these scatter plots is summarized in FIG. 3C as a ratio of the percentages of cells in each phase of the cell cycle in treated cells as compared to control cells. The ratio of treated to control cells in G0/G1 is very close to one suggesting that nanomaterial treatment does not induce a block in G1. Ratios of cell in S-phase of treated to control were also similar, with a student t-test demonstrating borderline significance. The p-values for both nanomaterial treatments were both slightly over 0.05. The largest difference in ratio, approximately 1:1.2 for both treatments, was in G2/M (FIG. 3C), indicating a possible G2/M block and S phase delay during cell cycle.

The results outlined above indicate that the reduction in cell number is due to both apoptosis/necrosis and a possible G2/M block. As measured by student t-test and percentage change from control, apoptosis/necrosis appears to be a more significant mechanism for the reduced cell number after nanomaterial treatment. These results are consistent with other studies done with water soluble fullerenes described in the literature and toxicity studies using MWCNTs in Shvedova, A. A. et al. Exposure to carbon nanotube material: assessment of nanotube cytotoxicity using human keratinocyte cells. *J Toxicol Environ Health A* 66, 1909-1926 (2003).

Example 5

Gene Expression in Nanomaterial Exposed Cells

Treating human skin fibroblast with carbon nanomaterials induced profound gene expression changes. Gene expression profiling was performed with the new generation Affymetrix High Throughput Array (HTA) GeneChip® system. Table in FIG. 4 lists numbers of genes whose expression levels changed after treatment with different particles and doses. We compared gene expression changes using different doses of the same particle structure (FIGS. 4B, 4C). These data indicate that, although higher doses induced a greater number of genes expression changes than low doses, there is no global dose-dependent responses to both particles. This is demonstrated by the small portion of genes that were changed commonly at both low and high doses (FIGS. 4B and 4C, Supplement Table S2 and S5). The data indicated that distinct pathways were activated in cells treated with low dose or high dose nanomaterials. This is a phenomenon reported before for other cellular stress factors, we have observed similar qualitative differences between carefully chosen low and high doses of radiation (Ding, L. H. et al. *Radiat Res* 164, 17-26 (2005)).

We also compared genes that demonstrate altered expression after treatment with different types of carbon nanomaterials (FIGS. 4D, 4E). The number of genes in the area of intersection in the Venn diagram in FIGS. 4D and 4E indicates a large percentage of genes show a common expression changes after treatment with both types of particles (Supplement Table 16 and 19). However, unique genes were also induced in response to MWCNO or MWCNT and more genes demonstrated changes in levels of expression at the lower concentration of MWCNOs than that with lower concentration MWCNT treatment (FIG. 4). Interestingly, it is the dosage of carbon nanomaterial that appears to have the greatest influence on gene expression changes in common between MWCNOs and MWCNTs, not the specific nanomaterial. This could be similar to the threshold effect that is observed after cells are treated with other insults, such as radiation Specific Transcriptional Changes.

Genes that demonstrated expression level changes after nano particle treatment were placed into functional categories, evaluated for statistical significance, and then sorted by significance (Table 1). The top ten categories are listed in Table 1 with the percentages of genes over- and under-expressed calculated. At the low dose, MWCNO and MWCNT treatment caused expression changes in similar groups of genes, including Golgi vesicle transport, secretory pathway, fatty acid biosynthesis, protein metabolism and G1/S transition of mitotic cell cycle (Table 1), with down-regulated genes dominating in all of these categories. An additional group of genes, involved in protein ubiquitination, were up-regulated (Supplement Table S13). These data suggest that when cells are treated with a low dose of carbon nanomaterials there is decreased cell growth and metabolism, but increased protein degradation. Conversely, treatment with both MWCNOs and MWCNTs at high dosages induced up-regulated genes in tRNA aminoacylation and amino acid metabolism pathways, indicating positive regulation of amino acid and protein biosynthesis.

Changes in the expression of functionally related genes were found at high doses of CMWNT treatment. These included gene involved in the inflammatory and immune response (Table 2). Most of the genes in this category can be ascribed to the innate immune system and generally are induced in response to interferon (IFN) and the defense against virus. STAT1 (for signal transduction and activator of transcription-1) (Table 5) is activated by a number of different ligands, including interferon-alpha (IFNA), interferon-gamma (IFNG), and IL6 and in turn regulates IFN7 production. Treatment with MWCNTs up-regulates STAT1 leading to an observed IRF7 induction in these cells. IFN7 was recently demonstrated to regulate all elements of IFN responses, including the systemic production of IFN in innate immunity. IRF1, also up-regulated, has been demonstrated to play an important role in transcription activation of type I IFN genes. Additionally, most of the genes in Table 2 are IFN inducible including ADAR, CXCL10, G1P2, G1P3, IFI44, IFIT1, IFIT2, IFIT36, and IFIT5 among others (Table 2). Several induced genes are also specifically associated with an antiviral response including MX1, MX2, OAS1, OAS2 and OAS3. The MX proteins are related to an interferon-regulated mouse protein induced by influenza virus and the OAS proteins have been observed to be induced as a response to the yellow fever vaccine. These data indicate that MWCNTs may interact with cells differently than MWCNOs and this type of interaction influences the cellular response. Based on the large number of genes associated with cellular response to viral infection and an IFN type I response MWCNT treatment may mimic viral infection in some respects.

Many of the genes altered in expression after treatment with the lower concentration of nanomaterials are those involved in transport, membrane fusion, and secretion (Table 3). These genes did not show discernable changes in expression with higher concentrations of MWCNOs and MWCNTs. Many of the genes in this category; SNAP23, NAPG, NAPA and GBF1 are involved in the process of docking and fusion of vesicles to their target membranes. Most of the genes in this category are under expressed indicating that the cells may be slowing secretion of proteins. Treatment of cells with the lower concentrations of nanomaterials also has an impact on the expression of cell cycle genes (Table 4) and genes involved in ubiquitination (Table 21). Again, many of these genes are down-regulated, indicating a slowing of cell proliferation and protein degradation.

Table 5 lists genes involved in apoptosis that were induced or repressed with nanomaterial treatment. A greater number of genes involved in apoptosis were observed to be up-regulated with MWCNT treatment at the higher dose, possibly explaining the greater number of apoptotic and dead cells observed with high content screening (FIG. 2). Of interest was the up-regulation of the cytokine and TNF family member, TNFRSF10B (TRAILR2) in cells treated with the highest concentration of MWCNTs, which is known to induce apoptosis. Also, the RIPK2[73] gene contributes to the induction of apoptosis and was observed to be up-regulated in these treated cells. At lower doses, many of the genes related to apoptosis listed in Table 5 are down-regulated and are anti-apoptotic; examples include EGFR, MCL1[7], BCL2L1, and CRKL. Up regulation of YARS was observed with both nano-material treatments, especially with the higher concentrations. YARS is believed to contribute to apoptosis by arresting translation and producing cytokines.

Large numbers of stimuli response genes were observed to be up-regulated with the higher concentration of nanomaterials (Table 6). These include the immune response genes pictured in Table 2. A few were down-regulated in this category, including FOS, which is related to an increase in cell proliferation. Again, most of the observed transcriptional changes were observed with treatment with MWCNTs at high concentration, although stimulus response genes were also induced with MWCNO treatment. These results points to a concerted cellular reaction to offset a cellular insult from the addition of nanomaterials, with the greatest response being observed with MWCNT treatment at the higher concentration. This is consistent with the greatest phenotypic response with respect to apoptosis, cell death, and proliferation also being observed at the higher concentration of nanomaterials.

Promoter Analysis.

According to our analysis of regulatory elements (cis elements) within the promoters of genes altered in expression upon carbon nanomaterial treatment, different pathways appear to be activated depending upon the nanomaterial dosage. As gene expression patterns observed in microarray experiments reflect the activity of transcription factors (TFs) in trans, we can trace back the regulatory cascades upstream of the physiological effect. This is performed by identifying the enriched transcription regulatory elements on the promoters of genes demonstrating altered expression profiles. These analyses were performed using the microarray data from MWCNT and MWCNO treated HSF cells at low and high dosages. Referring now to FIG. 5A, the interaction matrix is shown for the differentially expressed genes (horizontal) and transcription regulatory elements (vertical) in the up- and down-regulated gene sets at different dosage using different carbon nano-particles. The PAINT software then computes p-values to look for the overrepresented TREs in the set of promoters analyzed in reference to all the genes in the PAINT database to generate filtered (p-value value<0.01) interaction matrices. Individual elements of the matrix are colored by the significance p-values: over-representation in the matrix is colored in red. The brightest red represents low p-value (most significantly over-represented). The enriched transcription regulatory elements for the nano-particle dataset are specifically called out in the figure.

Promoter analysis of the predominantly down-regulated genes at the lower dosages points to the enrichment of EGR1 (KROX1), GATA4, ELK1 and USF regulatory elements in cells treated with MWCNO versus GATA4, ELK1 and USF regulatory elements in cells treated with MWCNTs (FIG. 5). Promoters in genes of up-regulated transcripts demonstrate the enrichment of EGR1 binding elements. However, the transcription of EGR1 is down-regulated after MWCNO treatment indicating that up-regulation of some transcripts may be a consequence of relieved repression as opposed to activation. GATA4, EGR1, USF and ELK1 TFs have all been shown to be phosphorylated and activated by ERK and p38 MAPK cascades. The down-regulation of these TFs may reflect the down-regulation of the MAPK cascades. This hypothesis is partially validated by the observation that p38 (MAPK14) expression is down-regulated in both experiments with lower dosages of MWCNOs and MWCNTs.

Treatment of cells with higher dosages of carbon particles caused a more pronounced effect on gene expression than lower dosages with more transcripts up-regulated as opposed to down-regulated (FIG. 5). The promoters of up-regulated genes in MWCNT treated cells are enriched with IRFs, ets1, PPAR and EGR1 regulatory elements whilst MWCNO treated cells are enriched with C/EBPdelta, E2F1 and EGR1 regulatory elements (FIG. 5). Mechanistically, cells treated with both of the higher doses of carbon nanomaterials appear to trigger responses from the activated p38 and ERK MAPK cascades, based on transcription factor profiling. In fact, CCAAT enhancer binding protein delta (C/EBPdelta), enriched in MWCNO treated cells, is a target of p38 MAPK and is associated with growth arrest in epithelial cells. However, the expression pattern of higher dose MWCNT treatment differs significantly from that of MWCNO treatment: For example, a robust IFN response is observed in MWCNT treated cells, but not in MWCNO treated cells. The presence of IRF elements contained within the promoters of many of the up-regulated genes may explain this response. In fact, IRF7 is one of the up-regulated genes observed (Table 2) and is believed to be central to an IFN response along with STAT1 (Table 5), another up-regulated gene discussed above, and one of the central signal transduction factors needed for an IFN response. Transcriptional regulatory elements present in the down-regulated genes of cells treated with MWCNOs, such as GATA1 may also contribute to the differences in gene transcription observed. FOS gene expression is also reduced, leading to a lowered activity of AP1 (FOS/JUN) transcription factors. These differences may be responsible for the difference in the magnitude of response between these particles, observed phenotypically by high content analysis. Additional experiments monitoring the kinase activities should give us better understanding the underlying mechanism.

Example 6

Cytotoxic and Kinetic Studies for Nanoonions for Therapeutic Use In Vivo

To determine pathophysiologic effects of nanomaterials in specific tissues/organs exhibiting profiles of distress/toxicity as determined by systemic oxidative stress and/or clinical chemistry and toxicogenomics, we will evaluate those retaining nanomaterials (as determined by imaging) or tissues/organs exhibiting altered functions over a time-course for parameters such as localized cytoxicity and cell death, oxidative stress, inflammation, vascular homeostasis, lymphatic homeostasis, IFP and evidence of auto-immunity. The specific order in which these analyses will be conducted will be determined in part by results from clinical chemistry analyses as well as results from in vivo and ex vivo imaging of nanomaterials and general health characteristics of manipulated mice. For example, if blood chemistry or hematology profiles indicate organ/tissue inflammation, 8-isoprostane levels will be examined as a marker of oxidative stress followed by assessment of the nature of inflammation, e.g., tissue retention of nanomaterial, cell death due to localized cytoxicity, altered vascular homeostasis, ischemia (Miles, A. A., and Miles, E. M. (1952). Vascular reactions to histamine, histamine-liberator and leukotaxine in the skin of guinea pigs. *Journal of Physiology* 118, 228-257) or elevated IFP (Eichten, A. E., Hyun, W. C., and Coussens, L. M. (2005). Characteristics of hematogenous and lymphatic vasculature during de novo epithelial carcinogenesis. Manuscript submitted; Boucher, Y., Brekken, C., Netti, P. A., Baxter, L. T., and Jain, R. K. (1998). Intratumoral infusion of fluid: estimation of hydraulic conductivity and implications for the delivery of therapeutic agents. *Br J Cancer* 78, 1442-1448; Tong, R. T., Boucher, Y., Kozin, S. V., Winkler, F., Hicklin, D. J., and Jain, R. K. (2004). Vascular normalization by vascular endothelial growth factor receptor 2 blockade induces a pressure gradient across the vasculature and improves drug penetration in tumors. *Cancer Res* 64, 3731-3736). These analyses will reveal if inflammation is a primary response in specific tissues where nanomaterials are retained and immunogenic, or secondary to altered vascular homeostasis, and subsequent changes in capillary permeability, impaired clearance by lymphatics and elevated IFP. If capillary permeability is found to be altered, we would assess to what degree lymphatic dysfunction follows as demonstrated by IFP, edema or enlarged lymphatics by lymphatic image analysis and/or MRI (Eichten, A. E., Shen, H.-C. J., and Coussens, L. M. (2005). Three-dimensional visualization of blood and lymphatic vasculature in tissue whole mounts using confocal microscopy. *In Current Protocols in Cytometry*, Volume 12.5, J. P. Robinson, ed. (New Jersey: John Wiley & Sons, Inc.), p. In press). To determine if inflammation or organ dysfunction may be imparting or underlying a systemic autoimmune process, we will evaluate presence of immunoglobulins in tissue sections collected from multiple organ sites (de Visser, K. E., Korets, L. V., and Coussens, L. M. (2004). Early Neoplastic Progression Is complement Independent. Neoplasia 6, 768-776; de Visser, K. E., Korets, L. V., and Coussens, L. M. (2005). De novo carcinogenesis promoted by chronic inflammation is B lymphocyte dependent. Cancer Cell In press). In combination, these studies will help to establish toxicologic, pharmacokinetic, biodistribution and pathophysiologic properties of nanomaterials in vivo in healthy mice and set the stage for further evaluation in tier 4 studies.

Toxicity:

Nanomaterials will be used in toxicity studies in healthy mice at multiple dosing levels, delivered by various routes, to determine MTD and evidence of induced organ/tissue toxicities. MTD of nanomaterial formulations will be determined in groups of 3 mice per concentration and route of compound to be tested. On the day of the experiment, mice will be randomly grouped and individually marked in appropriately labeled cages. After single exposures, survival, morbidity and body weights will be monitored. Individual body weights will be recorded 3-times/week for 14-days. All animals will be observed for signs of ill health based on body weight, appetite, rough coat, grooming, behavioral changes such as altered gait, lethargy and gross manifestations of stress. Should signs of severe toxicity or illness be observed, animals will be euthanized and necropsy performed to assess other signs of toxicity. Any and all of these findings will be recorded as raw data and the time of death will be logged as the following day.

Biodistribution/Pharmacokinetics:

Mice will receive a single exposure to saline or nanomaterial immunoliposome reconstituted in saline at the MTD. Blood, urine and organs will be collected from saline and nanomaterial treated mice at 5-min, 15-min, 1-, 3-, 6-, 12-, 24- and 48-hrs post injections. Where possible, urine will be collected from mice prior to termination and at other time points. All blood, urine and organs (liver, spleen, lung, heart, kidney and tumor if present) will be flash frozen and stored at −80° C. prior to evaluation where tissue, cells and/or plasma will be tested for total nanomaterial content by HPLC, using a method based on that of Seymour et al, in The pharmacokinetics of polymer-bound adriamycin, Biochem Pharmacol 39, 1125-1131 (1990), hereby incorporated by reference. Time points will contain a minimum of 5 age-matched animals.

In Vivo MRI of Tissue:

Animals subjected to MRI scanning prior to nanomaterial injection and at several times after injection will be performed on a Varian system equipped with a 7.0-Tesla, 18.3-cm horizontal bore magnet (300-MHz proton frequency) inside the MT Zion the barrier at UCSF. For MRI, mice will be anesthetized with sodium pentobarbital (70 mg/kg i.p) and maintained at 37° C. inside the magnet using a heated circulation water blanket, with pelvis motion minimized by a plastic support placed before insertion into a 3-cm diameter quadrature birdcage coil. Multislice images will be acquired using a T1-weighted spin echo sequence (TR/TE=880/13, field of view=30 Å~30 mm using a 128 Å~128 matrix, slice thickness=1.5 mm, and slice separation=1.0 to 1.6 mm). Each set will contain 9-25 slices and enough sets obtained to provide contiguous image data of the tissue. Tissue volume will be measured using the formula V=4/3[(D1+D2)/4]3, where D1 and D2 correspond to the longest and shortest (transverse and sagittal) diameter measured from the MRI image. Tissue volumes obtained from final MRIs will be compared with findings from direct anatomical inspection at tissue dissection/necropsy.

Example 7

Cytotoxic Studies of Semiconductor Nanocrystals

Because of the potential for semiconductor nanocrystals to provide additional information about biological process in vivo, it is important to understand the toxicology of these foreign nanomaterials. Studies so far have been limited to determining the survival rate of cells exposed to nanocrystals for less than 48 hrs. These studies have demonstrated that the surface functionalization plays the key role in nanoparticle toxicity. For example, CdSe/ZnS solubilized by a simple ligand exchange with a mercaptoacid, are less soluble and are toxic to breast cancer cells above a threshold concentration in the nM range. This is caused by the release of $Cd^{2+}$ ions into solution because of the weak and dynamic bond between the nanocrystal surface and the mercapto-surfactant. In contrast, $Cd^{2+}$ release is noticeably slowed if nanocrystals are embedded in a cross-linked shell reducing toxicity. For example, cells treated with CdSe/ZnS nanoparticles embedded in a silica shell do not show signs of toxicity, even when treated with dosages 6-12 times higher that the toxicity-inducing dosage of mercaptoacid coated CdSe/ZnS semiconductor nanocrystals. See Kirchner, C.; Liedl, T.; Kudera, S.; Pellegrino, T.; Muñoz Javier, A.; Gaub, H. E.; Stölzle, S.; Fertig, N.; Parak, W. J. *Nano Letters* 2005, 5, 331-338. These experiments have helped to illuminate some of the reasons for the toxic effects of semiconductor nanocrystals to live organisms, and have provided guidance on how to modify the nanocrystals to negate these concerns.

One question that remains to be answered is how cells respond at the molecular level after treatment with nanomaterials below the dosage causing high percentage cell death. Even minute changes may have profound effects on the integrity and viability of the cells over multiple cellular divisions. In order to address this question we examined the impact of the treatment of both human lung and skin epithelial cells to two dosages of PEG-silane semiconductor nanocrystals. Two dosages were selected, one reported to be nontoxic to breast cancer cells and a 10-fold higher dosage. Human skin (HSF-42) and lung fibroblasts (IMR-90) were selected because skin and the respiratory track is the most likely route of human exposure. Furthermore, molecular and genetic data addressing the cytotoxicity of carbon nanostructures for these cells lines is available. Presented here are measurements of phenotypic changes in large populations of cells combined with expression array analysis of exposed cells. The results indicate that both high and low doses of PEG-silane-semiconductor nanocrystals present a similar average response from the cells. We do not see adverse effect in lung epithelial cells, while in the case of skin epithelial cells, PEG-silane-semiconductor nanocrystal treatment exerts a slight repression of genes regulating cell cycle progression. In general though, only <50 genes out of more than 22,000 probed (eq. ~0.2% of total genes) show significant changes in the expression level due to the presence of the PEG-silane-Qdots. Detailed analysis allows the classification of these genes into functional categories and promoter analysis reveals affected regulatory pathways. As expected, we observe minor involvement of cell endocytosis and intracellular transport pathways. Remarkably, the global picture emerging from our study is that PEG-silica semiconductor nanocrystals have a negligible toxicological effect on these two cell lines. This study is a critical first step to characterize the toxicity of coated semiconductor nanocrystals at the molecular level in an in vitro culture system.

A detailed description of the experimental procedures and of the materials used can be found below. Here we first describe some salient features of the experimental protocol. We used silica-coated CdSe/ZnS semiconductor nanocrystals terminated with both thiol and PEG functional groups. While the core/shell semiconductor nanocrystals are only ~4-5 nm in size, the silane shell adds ~2-3 nm in thickness and thus silanized semiconductor nanocrystals are ~8-10 nm in diameter. Such semiconductor nanocrystals chemistry was observed in Kirchner, C.; Liedl, T.; Kudera, S.; Pellegrino, T.; Muñoz Javier, A.; Gaub, H. E.; Stölzle, S.; Fertig, N.; Parak, W. J. *Nano Letters* 2005, 5, 331-338, to pose minimal toxicity to breast cancer cells when the cells were exposed to a solution containing 2-10 nM of PEG-silane-semiconductor nanocrystals.[26] Human lung (IMR-90) and skin epithelial (HSF-42) cells were exposed for 48 hrs to a medium containing 8 nM or 80 nM of semiconductor nanocrystals, or to an equivalent amount of 10 mM phosphate buffer as a control.

Phenotypical measurements of cell proliferation, apoptosis, necrosis and cell cycle distribution were performed using a High Content Image Analyzer (HCA). Cells were detected and counted by staining their nucleus with Hoechst dye. Further distinction between apoptotic and necrotic cells was done using DNA dyes that transverse membrane of apoptotic and necrotic cells respectively. For instance YO-PRO-1, a green dye, can cross the slightly impermeable membranes of apoptotic cells while Propidium Iodide (PI), a red dye, crosses the membrane of necrotic cells due to their greater permeability. Cell cycle distribution was performed by adding bromo-deoxyuridine (BrdUrd) to the cell medium and subsequently staining the cells using anti-BrdUrd antibody labeled with AlexaFluor 488 and PI to obtain DNA content information. After images from stained culture plates were obtained, intensity measurements for both BrdUrd and DNA staining were made for each identified cell to generate a scatter plot with BrdUrd intensity on the Y-axis and PI intensity on the X-axis. Analysis of these scatter plots allow estimation of the percentages of these cells in G0/G1, S, and G2/M phases.

Gene expression profiling was obtained with an Affymetrix High Throughput Analysis automated Genechip system. Target preparation, washing and staining were carried out on a Affymetrix/Caliper robotic system, and scanning was performed on a CCD-based High Throughput scanner. The chip contains ~22,000 probe set, among which 18,400 are known genes or probe sets. Data analysis has been performed using Genesping, Bioconductor, GeneTraffic, Cluster 3.0, PAINT, GoMiner and Pathway Assist.

EXPERIMENTAL

Cell Culture, TGF-β1 Treatment and RNA Isolation.

The biological model system we used for evaluation is human bone marrow mesenchymal stem cells (MSCs) treated with transforming growth factor β1 (TGF-β1). MSCs can be differentiated into a variety of cell types in response to TGF-β1, with increased smooth muscle (SM) α-actin expression in MSCs (Kinner, B., Zaleskas, J. M. & Spector, M. Regulation of smooth muscle actin expression and contraction in adult human mesenchymal stem cells. *Exp Cell Res* 278, 72-83 (2002); Wang, D. et al. Proteomic profiling of bone marrow mesenchymal stem cells upon transforming growth factor beta1 stimulation. *J Biol Chem* 279, 43725-43734 (2004)). MSCs were obtained from Cambrex Corp (Walkersville, Md.). The surface markers and differentiation potential of these MSCs have been well characterized, i.e. positive for CD105, CD166, CD29, and CD44, but negative for CD34, CD14, and CD45 (FIG. S3). Maintained at 37° C. with 5% $CO_2$, MSCs were cultured in Mesenchymal Stem Cell Growth Medium (MSCGM) with 10 mM L-glutamine, 10% pre-screened fetal bovine serum (Cambrex Corp.) and 1% Penicillin-Streptomycin (Invitrogen) to allow for cell proliferation without differentiation. Cell culture products and other consumable laboratory supplies were purchased from Fisher Scientific Corp. (Fairlawn, N.J.) and VWR International (Brisbane, Calif.). MSCs up to passage 14 were used in our experiments for gene expression analysis. TGF-β1 (Sigma-Aldrich Corp.) at 5 ng/ml was used to treat MSCs for 24 hours. One 100 mm dish was used for each treatment, which was performed in triplicate. Cells in each dish were lysed with 1 mL RNA Stat 60 (Tel-Test Inc, Friendswood, Tex.). RNA was extracted using chloroform and phenol extraction steps. RNA was resuspended in DEPC-treated water and quantified using a RiboGreen® RNA quantification assay (Molecular Probes Inc, Eugene, Oreg.).

Flow Cytometry.

To confirm MSCs maintain their phenotype after expansion in culture, the cells were subjected to flow cytometry analysis. The cells were detached by trypsin treatment, followed by centrifugation and washing with PBS. After resuspension of the cells, the non-specific binding sites were blocked by incubation with 1% bovine serum albumin (Sigma) for 30 min. All incubation steps were performed at 4° C. For primary antibodies conjugated with FITC (CD14, CD34, CD45, CD105, CD166), the samples were incubated with the primary antibody for 30 min, and the expression level of each surface marker was quantified by using a Beckman-Coulter EPICS XL flow cytometer. As a negative control, cells were incubated without primary antibody in PBS. For primary antibodies without FITC conjugation (CD29 and CD44), the samples were incubated with an antibody against each of the surface markers for 30 min, and stained with a FITC-conjugated secondary antibody (Molecular Probes, Eugene, Oreg.) for 30 min, followed by flow cytometry analysis. As a negative control, cells were incubated only with the FITC-conjugated secondary antibody. The antibodies against the surface markers CD14 and CD45 were from Santa Cruz Biotechnologies (Santa Cruz, Calif.). CD34 antibody was from BD Biosciences (San Jose, Calif.). CD29 and CD105 antibodies were from Chemicon (Temecula, Calif.). CD166 antibody was from Serotec (Raleigh, N.C.). CD44 antibody was from Biosource (Camarillo, Calif.).

cRNA Generation and Biotin Labeling.

As determined by the RiboGreen® dye assay, 100 ng of total RNA was used in a MessageAmp™ II aRNA (Ambion, Austin, Tex.) reaction. (antisense RNA is referred to as cRNA). Total RNA was reversed transcribed with an oligo (dT) primer bearing a T7 promoter into first strand cDNA and used as a template for second strand cDNA synthesis. The resulting cDNA was then column purified and used in an in vitro transcription reaction with T7 RNA Polymerase to generate cRNA copies of each mRNA in the sample. For RNA labeling, 25% of the UTPs in the in vitro transcription reaction was replaced by Biotin-16-UTPs (Roche Molecular Biochemicals, Mannheim, Germany) to generate biotinylated cRNAs. The cRNA sample was then column purified, quantified with RiboGreen® dye, and qualified with the RNA 6000 Pico LabChip® assay. Successful cRNA samples showed a broad hump with no presence of ribosomal RNA.

Gene Expression Analysis Bead Panel.

For the 100-plex panel used in this manuscript, the barcoding scheme is as follows. A total of 12 equal portions of Qdots are added to the coding mixture. Each portion contains only a single color of Qdot, chosen from the emission colors of 525 nm, 545 nm, 565 nm, 585 nm, as indicated in FIG. 1. The 605 nm color used in the QBeads in FIG. 1 is not used during the decoding step in this manuscript since enough multiplexity can be achieved with just 4 colors. The combination of these 4 colors of Qdots during the barcoding gives a combination possibility of 455. Out of the 455 possibilities, 200 of the nanobarcodes are manufactured by coating the magnetic microbeads with a proprietary polymer-Qdot mixture in 12 steps.

We custom-designed probes 60 base pairs in length for each gene represented in the gene panel. Gene-specific oligonucleotide probes with a 5' amine modification were synthesized (Biosearch Technologies, Inc., Novato, Calif.), and conjugated to paramagnetic beads encoded with Qdot nanocrystals (Quantum Dot Corporation, Hayward, Calif.). Two percent 1-Ethyl-3-(3-dimethylaminopropyl) carbodiimide (EDAC) (Invitrogen Corporation, Carlsbad, Calif.) was used in an amine-carboxylic acid cross-linking reaction. 200 pmoles of the gene-specific oligonucleotide probe were conjugated to 1 million encoded beads. The final gene panel used for hybridizations contains a hundred different encoded beads. 100 different gene specific probes were conjugated to 100 different bead codes while 20 control and calibrator sequences were conjugated to another 20 different beads. Hybridization to complement gene-specific oligonucleotide targets was used to verify that the correct probe was conjugated to the expected encoded bead.

QBead System Hybridization.

Hybridizations were performed in 96-well PCR plates (Axygen Scientific Inc., Union City, Calif.), where one well contained a different sample hybridized to the 100-plex gene panel. One microgram of the biotin-labeled cRNA sample was hybridized in a 50 μL 3×SSC/0.2% SDS hybridization solution at 65° C. for 2 hours. Post-hybridization washes were performed using a 96 channel Biomek® FX Laboratory Automation Workstation (Beckman Coulter, Inc., Fullerton, Calif.). Hybridized beads were washed 5 times in a 0.5×SSC/0.05% SDS solution at room temperature, followed by 3 washes with 1×TBS/0.1% BSA/0.1% sodium azide staining buffer solution at room temperature. The quantification reporter used is a Qdot 655 Streptavidin Conjugate. A 4 nM stock of Qdot 655 Streptavidin Conjugate was added to each well that contained 50 μl of staining buffer. The beads were incubated at room temperature for 20 minutes with mixing at 4-minute intervals followed by 4 room temperature post-staining washes with 1×TBS/0.1% BSA/0.1% sodium azide solution. After that, beads were resuspended in a 5% PAA/0.1% azide in 50 mM borate scanning buffer and transferred to a 384-well glass-bottom microplate (BD Biosciences, Bedford, Mass.) for scanning.

Scanning and Data Acquisition.

The 384-well plate was sealed with a clear adhesive and scanned on the Mosaic™ Q1000 Scanner (Quantum Dot Corporation, Hayward, Calif.). The Mosaic™ scanner acquired images within each well from multiple fields of view at 9 different wavelengths. The software then measured the intensities of individual beads at the 9 different spectral wavelengths ranging from 505 nm to 655 nm followed by decoding the beads' spectral pattern to determine the identity of the specific gene (525 nm, 545 nm, 565 nm, and 585 nm) and quantify the amount of target hybridized to each bead nanobarcode (655 nm). Gene-specific results, bead results, and control bead results were generated for each sample.

Quantitative Polymerase-Chain-Reaction (qPCR).

RNA isolation and two-step reverse-transcription were performed as previously described in Ding, L. H. et al. Gene expression profiles of normal human fibroblasts after exposure to ionizing radiation: a comparative study of low and high doses. *Radiat Res* 164, 17-26 (2005), hereby incorporated by reference. qPCR was performed using SYBR-green kits and the ABI Prism® 7000 Sequence Detection System (Applied Biosystems, Foster City, Calif.). Primers for SM β-actin and 18S were designed using the ABI Prism Primer Express™ software v.2.0 (Applied Biosystems). After each experiment, the melting temperature and the dissociation curve of PCR products were obtained to corroborate the product specificity. The amount of RNA for each gene was normalized with the amount of 18S RNA in the same sample.

Affymetrix GeneChip® Microarray Hybridization and Data Acquisition.

An Affymetrix High-Throughput Automation (HTA) GeneChip® system was used for acquisition of the microarray data for the gene expression profiling[5]. Target preparation, washing, and staining have been performed on an Affymetrix GeneChip® Array Station (GCAS), and scanning was performed on a CCD-based Affymetrix High-Throughput (HT) scanner, which is a fully automated epifluorescent imaging system. More details for the HTA protocols can be found in Examples 1-5.

Results

Cellomics.

Figure 9A:
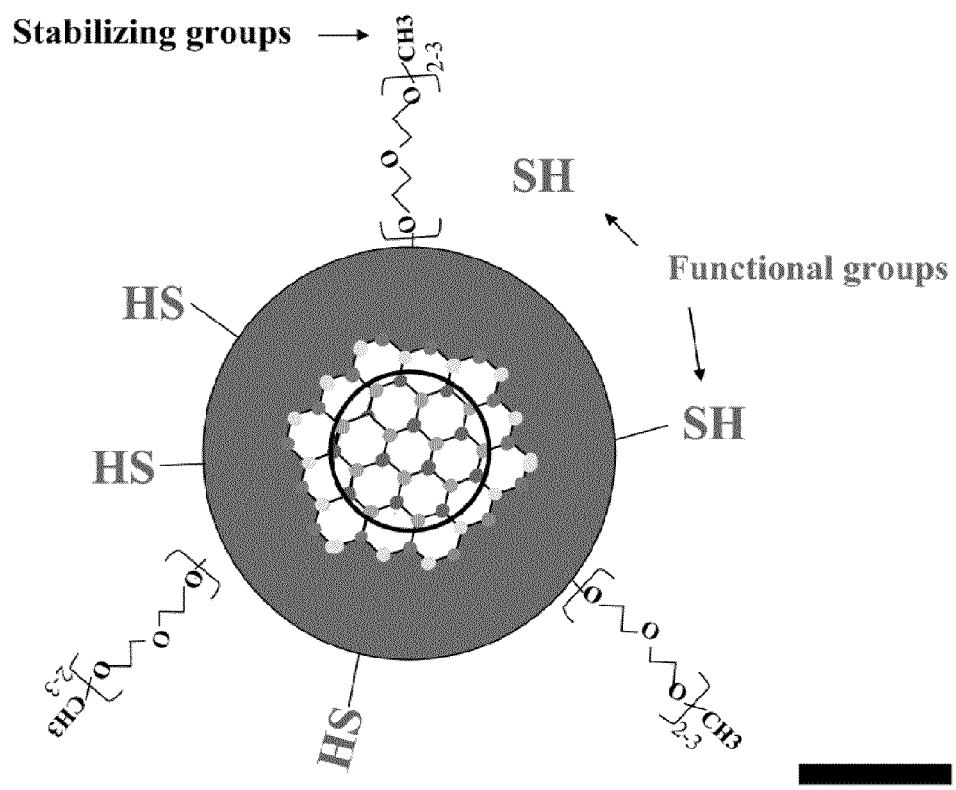
FIG. 9. A. Schematics of the PEG-silica embedded semiconductor nanocrystals. The silica shell is functionalized with —SH groups and with PEG group. The latter provide additional stability and reduced non-specific bindings. The scale bar (~3 nm) provides a qualitative comparison between the overall size of the silanized dot (~8 nm) and the size of the semiconductor core (~3 nm). B. Semiconductor nanocrystal localization in HSF42 cells, after 48 hrs of incubation. The nuclei are stained with DAPI, a blue dye. Yellow semiconductor nanocrystals are localized either in the cytoplasm or in the perinuclear region. Notice that about half of the cells in the image are in the post-mitotic stage.
Figure 9B:
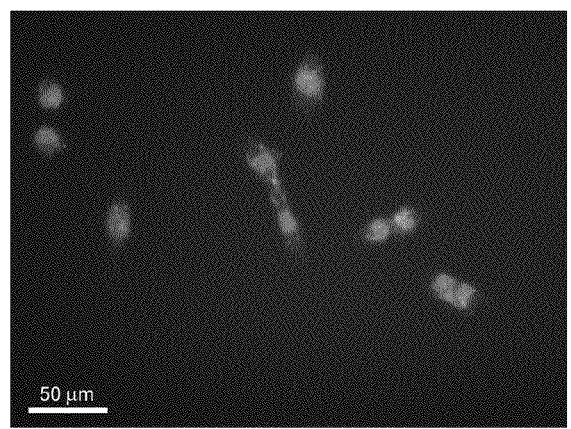

PEG-coated silanized Qdots (Qdots), schematically represented in FIG. 9A, were added to the cell culture medium. Human Skin Fibroblasts and Lung Fibroblasts were selected as model systems because entry of nanomaterials through the skin and respiratory track is the most likely route of human exposure to nanomaterials. In addition, genotoxicity data of carbon nanotubes and nano-onions are available for these cells and can be used for comparison purposes. See Ding, L.; Stilwell, J.; Zhang, T.; Elboudwarej, O.; Jiang, H.; Selegue, J. P.; Cooke, P. A.; Gray, J. W.; Chen, F. F. *Nano Letters* 2005, In press. Human Skin Fibroblast and Lung Fibroblast cells exposed to 8 nM or 80 nM of PEG-silane-Qdots for 48 hours internalize them (FIG. 9B). As shown in FIG. 1B, all cells are labeled by Qdots. The entry mechanism is likely endocytosis, as observed previously by Jaiswal et al. for Hela and *D. discoideum* cells.[30,31] The nanoparticles are stored in the perinuclear region, as most studies report,[23, 26] but we also observed PEG-silane-Qdots dispersed in the cytoplasm (FIG. 9B). A careful look at FIG. 9 and comparable images indicate a slightly elevated number of labeled cells are in the cytokinesis stage of mitotic cell cycle. This warrants further quantitative analysis of the cell cycle profile.

Cell Proliferation.

Forty-eight hrs after transfection, proliferation of cells labeled by PEG-silane-Qdots was evaluated through an automated counting method. Cells were labeled with Hoechst dye and counted with the KSR scanner. FIG. 10.I shows the average results from 10 independent runs, with error bars representing the standard deviation. For both cells lines after 48 hrs, statistically significant differences in the number of cells, either exposed to PEG-silane-Qdots or the unexposed control, are not observed regardless of the PEG-silane-Qdot dosage used for treatment. This indicates a neutral effect of treatment on both the cell proliferation rate and on the cell death rate over a period of 48 hrs, i.e. encompassing about 2 cellular division cycles.

Apoptosis/Necrosis.

Quantifying apoptotic or necrotic cells generated further information on cell cytotoxicity. Live cells are impermeable to YO-PRO1 and PI, two DNA staining dyes, but apoptotic cells are permeable to YO-PRO1 (a green dye), and necrotic cells are permeable to PI (a red dye). Thus, we could count and differentiate cells undergoing apoptosis or necrosis. The results of large scale analysis over more than 20,000 cells, replicated 10 times, are reported in FIG. 10II as the percentage of all cells exhibiting apoptosis or necrosis. Exposing human lung fibroblasts to either high or low dosages of PEG-silane-Qdots does not significantly increase the percentage of cells in an apoptotic or necrotic state compared to the control (~1.8-2% vs ~1.2-1.5%, FIG. 10.II.A). In contrast, a slight increase in both apoptosis and necrosis, from ~1-1.2% to ~2.7-2.8% is observed in human skin fibroblasts (HSF-42, FIG. 2.II.B). The increase is very modest and is independent of the dosage of PEG-silane-semiconductor nanocrystals in the medium.

Cell Cycle Profile.

Because lung fibroblasts IMR-90 do not show marked signs of cytotoxicity, we focused on the response of skin fibroblasts HSF-42 to the presence of PEG-silane-semiconductor nanocrystals in all subsequent analyses. First, we studied the proliferation profile of this cell line by incorporating BrdUrd into replicating DNA and counterstaining with PI to determine total DNA content. For each individual HSF-42 cell, the ratio of the signal intensity from antibody staining of incorporated BrdUrd versus total DNA content measured by PI staining is plotted in a scatter plot. We analyzed the cell cycle status of more than 20,000 cells, and then classified them into G0/G1, S or G2 µM phases. FIG. 10.III shows the relative percentage of treated cells compared to control cells in each of the three phases of the cell cycle. The ratio of PEG-silane-Qdot treated cells to control cells in G0/G1 is close to one, indicating that PEG-silane-Qdot treatment does not induce a block in G1. Similarly, the ratio of cells in S-phase of treated to control is ~0.94, with a student t-test demonstrating only borderline statistical significance. The largest difference in ratio occurs at the G2/M phase, where the ratio of cells treated with PEG-silane-Qdot vs control is ~1.1, possibly indicating a block in G2/M. However, because only 2 cell divisions have occurred in 24 hours this ratio either suggests no significant G2/M block or that it may only become apparent after multiples cell division cycles. An important observation based on this data is that the effect of PEG-silane-semiconductor nanocrystals on the cell proliferation, cell death and cell cycle regulation is much more subtle than the marked cytotoxic effects induced by treatment with carbon-based nanostructures, i.e. nanotubes and nanoonions, in these cell lines.[27] These observations are also consistent with gene expression results presented below.

Gene Expression.

The Affymetrix High Throughput Array (HTA) GeneChip® system was used to profile gene expression changes in Human Skin Fibroblasts labeled with PEG-silane-semiconductor nanocrystals. The results are plotted in a 2D diagram in FIG. 3 where each gene is represented by an (X,Y)-value in a log scale. The Affymetrix HG-U133Av2.0A of A GeneChip® contains 25mer oligoprobes, in sets for identification of transcripts from ~22,000 genes and ESTs in the human genome.

Each dot on the graph represents a gene where the X-value corresponds to the level of expression in control cells, while the Y-value corresponds to the level of expression of that same gene in the PEG-silane-semiconductor nanocrystals labeled cells. A dot that lands on the graph where the slope is 1 (red line) indicates no difference between the gene expression level of the treated and control samples. The two dotted lines flanking the central line indicate the cutoff for two-fold up-regulation (top line) or down-regulation (bottom line) of the sample vs. the control. Dots above or below the 2-fold box lines represent genes with a greater than two-fold change in gene expression and are discussed below.

Figure 11:
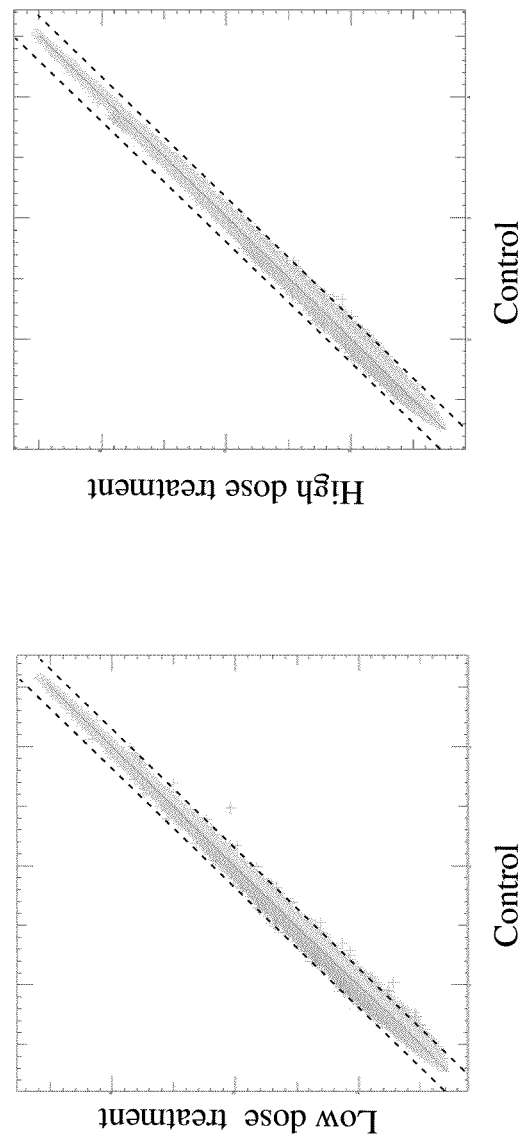
FIG. 11. A. Scatter plots for the two doses of PEG-silane-Qdot treatment, in a log 10 scale. The Y-axis represents treated cells, the X-axis represent the control. The line X=Y correspond to no difference in gene expression between the treated and control sample. The dashed lines correspond to changes of level of expression by a factor of 2. The tightness of the plot, indicates that most of the genes do not change significantly after PEG-silane-semiconductor nanocrystals treatment.
Figure 13:
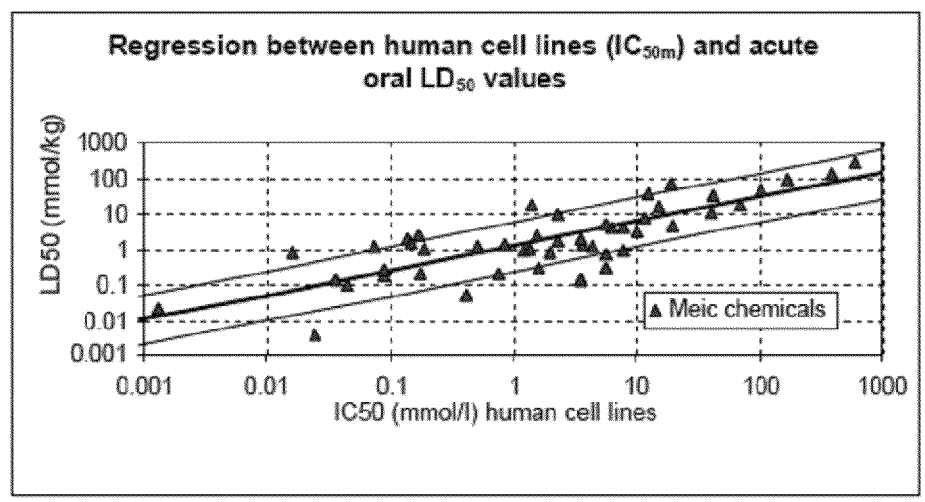
FIG. 13 is a graph showing close correlation between human cell line IC50 and acute oral LD50 value.

In FIG. 11A it is remarkably clear that most of the dots lie close to where the slope=1, with minimal dispersion up or down, indicating minimal changes in the gene expression in PEG-silane-Qdot treated cells compared to untreated. This is in strong contrast to treatment of these same cells with carbon nanotubes and nano-onions[27]. For instance, the MWCNT at a concentration of 0.6 mg/L induced significant changes in 216 genes, while the PEG-silane-Qdot induced changes in twenty times less genes at a much higher concentration of 40 mg/L (80 nM, with molecular weight approximately 500 KDa). Because there is little to no toxicity for these PEG-silane-semiconductor nanocrystals compared to other types of nanoparticles, this provides evidence that the composition and surface functionalization of the particle is the most important determinant of toxicity.

Thirty-eight genes were identified as being differentially expressed by more that 2-fold in the cells treated with a low dosage of semiconductor nanocrystals, while only 12 were identified for the higher dosage. Among these genes, 4 are shared both by low and high dosage experiments, representing approximately 20-30% of the genes analyzed. The combined number of genes demonstrating significant changes with these two treatments totals 46 genes, ~0.2% of the total number probed. We classified the genes into functional categories using the GoMiner program.[32] FIG. 11B lists the categories. The functional categories of the changed genes are consistent across the two different dosages. Genes overexpressed are mostly related to carbohydrate binding (CHI3L1, GPNMB, PRELP, TNXB), intracellular vesicle localization (CTSF, CTSH, GPNMB, PTGIS/CYP8A1) and cell membrane-associated and intracellular vesicular proteins involved in cellular response to stress (CLU, MAP2K6/MKK6, FST). Interestingly, both MAP2K6 and CLU are both implicated in the inhibition of apoptosis[33,34] and induction of senescence[35-38], while CLU is a sulfated glycoprotein on the cell surface 39. While there was some phenotypic evidence of some apoptosis, it was minimal. The 4 common genes between the low dose-induced group and the high dose-induced group are CORIN, BUB1, CHI3L1, and CLU, suggesting the interaction of PEG-silane-semiconductor nanocrystals with cell surface binding proteins (CHI3L1 and CLU).

There are far more genes observed to be down-regulated in the treated cells as compared to upregulated genes. The majority of the down-regulated genes fall into the functional categories controlling the M-phase progression in mitosis, spindle formation and cytokinesis (BUB1, CyclinA2/CCNA1, CDC20, KIF2A, KIF2C, NEK2, PLK1, PTTG, TACC3 for low dose and BUB1, MPHOSPH1 for high dose),[40-52] indicating that these proteins might account for the limited perturbation of M-phase progression by PEG-silane-semiconductor nanocrystals. In addition, the expression of the transcription factors FOXM1 and BHLHB2/Dec1 are also down-regulated in low dose treated cells. Interestingly, PEG-silane-semiconductor nanocrystals treatment does not seem to illicit any genes involved in wound healing or the immune response, contrary to both the responses we observed in human skin fibroblasts treated with carbon nano-tubes[27] and the response of dendritic cells to nanosphere treatment by others.[53] The lack of induction of these genes may underscore the negligible toxic effects of PEG-silane-Qdot treatment in this cell line. This observation also counters a widely held preconception that semiconductor nanocrystals are toxic to cells because of the presence of Cd in the nanocrystal.

One important discovery of this study was that genes associated with heavy metal exposure were not induced by PEG-silane-Qdot treatment. The gene expression changes revealed by gene expression profiling can be mostly attributed to the interaction between the cellular machinery to the PEG coating of the Qdot. The PEG silica coating is very robust under the biological conditions used in this study, greatly reducing or even eliminating the concern of Cd poisoning. Table 7 shows a comprehensive list of significantly changed genes.

Promoter Analysis.

By identifying and analyzing the enriched cis-regulatory transcription regulatory elements (TRE) on the promoters of differentially expressed genes in this experiment (FIG. 12), we were able to identify putative trans-regulating transcription factors. Data from HSF cells treated at high and low dosages of PEG-silane-semiconductor nanocrystals was included. Promoter analysis of the predominantly down-regulated genes at the higher dosage of PEG-silane-semiconductor nanocrystals suggests the enrichment of FOXO family transcription regulatory elements. Even though we did not see the under-expression of FOXM1 in the high dose treated cells in contrast to low dose treated cells, the over all transcriptional profile points to the down regulation of its activity. FOXM has been shown to activate the transcription of genes essential for mitotic progression.[54]

The promoter analysis of the down-regulated genes at the lower dosage points to the enrichment of two transcriptional regulatory elements: DEC and COMP1. Genes under-expressed in response to low-dose PEG-silane-Qdot treatment include BHLHB2/DEC1/STRA13. This gene is involved in transcriptional repression, differentiation, hypoxia-induced stress response, and circadian clock regulation. It was recently proposed to have a role in differentiation by promoting cell cycle exit.[55-58] There is not enough information about COMP1 to deduce its putative role in PEG-silane-Qdot response. The limited number of TREs identified by promoter analysis from the expression information from PEG-silane-Qdot treated cells contrasts with the large number of promoter regulatory pathways perturbed by other nanomaterials or environmental factors,[27,53,59] providing additional evidence for the minimal impact of PEG-silane-semiconductor nanocrystals on cells.

Discussion

Because of the increasing use of semiconductor nanocrystals in biomedical research, it has become extremely important to understand the impact and toxicity of semiconductor nanocrystals on cells and ultimately living organisms. Data obtained from our studies predicts that silanized CdSe/ZnS nanocrystals will have minimal, if any, impact on cellular functions. Even for the highest dosage we used, negligible phenotypic response of cells to PEG-silane-semiconductor nanocrystals and minimal global gene expression changes were observed. In fact, concentrations of 80 nM of PEG-silane-semiconductor nanocrystals (i.e. $\sim 5 \times 10^{10}$ particles/$mm^3$) in lungs or skin fibroblast cells represent a dosage that would be extreme and unlikely in cases of an accidental inhalation or exposure to semiconductor nanocrystals. Semiconductor nanocrystals solutions are typically stored in micro-molar concentrations and if inhaled will be spontaneously diluted below toxic concentrations.

When lung or skin fibroblast cells are treated with PEG-coated silanized semiconductor nanocrystals, the nanoparticles stay in vesicles in the perinuclear region or in the cytoplasm. In contrast to semiconductor nanocrystals with a nuclear localization sequence on the surface, PEG-silane-semiconductor nanocrystals are unable to cross the nuclear membrane, preventing their direct interaction with the genetic machinery in the cell nucleus. This precludes studies requiring the labeling of nuclear materials, creating a definite disadvantage.

Our data uncovers a surprising observation, that low or high dosages of Semiconductor nanocrystals during the incubation step does not induce a marked difference in the phenotypic response of cells. The higher dosage of semiconductor nanocrystals during incubation does however result in a higher degree of particle uptake as measured by a stronger fluorescent signal. It is unclear, however, if the 10-fold increase of PEG-silane-Qdot used for the incubation period results in a 10-fold increase of particle uptake. Of importance, the high concentration of semiconductor nanocrystals used in this study corresponds to an approximately 5-fold greater concentration than reported previously in toxicity studies using non-PEGalated semiconductor nanocrystals in Kirchner, C.; Liedl, T.; Kudera, S.; Pellegrino, T.; Muñoz Javier, A.; Gaub, H. E.; Stölzle, S.; Fertig, N.; Parak, W. *J. Nano Letters* 2005, 5, 331-338. Despite this high concentration, skin HSF-42 and lung IMR-90 cells only show a mild phenotypic response to PEG-silane-semiconductor nanocrystals, as measured by changes in cell proliferation, cell cycle regulation and cell death. Whether the same conclusion will hold true for treatment times covering multiple (>10) cell division cycles remains an open question. Similarly, it may seem counter-intuitive that lung fibroblast cells are less susceptible to PEG-silane-Qdot exposure than skin fibroblast cells. It is possible that the tissue-different gene expression pattern contributes to this effect. It is expected that organ-specific toxicological profiles will emerge if the semiconductor nanocrystals are administered to whole organism, and there will be issues such as clearance, transport, retention, and degradation of the PEG coating. However, the cellular-level molecular and cellomic profiling is an important first step for understanding the nanotoxicology of semiconductor nanocrystals, and the data here strongly indicate that in vitro cell imaging study can benefit from the non-toxicity of semiconductor nanocrystals.

The stimuli induced by the presence of semiconductor nanocrystals in human skin fibroblasts can be readout at the genetic level by monitoring gene expression changes in the cells. By applying significance analysis with Bonferroni multi-testing correction, we found that only a minute number of genes exhibit a statistically significant expression level changes. Out of more than 22,000 genes probes on the array, only ~50 (i.e. ~0.2%) show more than a two-fold expression change. Such mild change contrasts sharply with the much larger number of genes affected when HSF-42 are exposed to carbon nanoparticles.[27]

A careful analysis of the genes affected by the dosage of semiconductor nanocrystals reveals that 20-30% of genes affected at high dosage are also affected at low dosage. This may indicate a similar gene expression profile. In fact all functional categories of genes affected at high dosage are also affected at low dosage. The observed response in HSF-42 to semiconductor nanocrystals seems to be consisted of several aspects: reduced expression of genes involved in M-phase exit, including spindle checkpoint and cytokinesis; and increased expression of genes involved in vesicle transport and apoptosis avoidance. From the promoter analysis, we identified FOXM and BHLHB2 as the transcription factors responsible for the reduced expression, with minor biological significance. One of the main concerns in using semiconductor nanocrystals is the potential cytotoxicity generated by exposure to Cadmium. In this study, we found no evidence for altered expression of any genes involved in Cadmium ($Cd^{2+}$) and Se toxicity during the treatment. This is strong evidence for a resilient silica shell that restrains the leakage of CdSe. The altered expression of a few cytoskeletal proteins suggests that semiconductor nanocrystals may interact with the intracellular trafficking system during endocytosis and intracellular movement. This is a common mechanism used by intracellular labels that enter the cell through endocytosis. Of importance is that PEG-silane-semiconductor nanocrystals do not significantly impact cellular functions through these possible interactions. Both the high content imaging analysis (Cellomics) and high throughput gene expression profiling showed a consistent result for the PEG-silane-semiconductor nanocrystals.

Results from both high content cellomics analysis and comprehensive analysis of expression over the entire genome of cells treated with PEG-silica-coated semiconductor nanocrystals indicate minimal impact on cell health and molecular response of exposed cells. This provides evidence that proper coating and passivation of semiconductor nanocrystals allows their safe use for in vivo applications. This contradicts the commonly held belief that CdSe nanocrystals are poisonous due to Cd leakage, and may have widespread implications on the use of these particles in biomedical studies in living cells and organisms. Semiconductor nanocrystals are much less toxic than carbon nano-particles when used to treat skin fibroblasts. These studies can now be extended to determine if there are any long term effects of semiconductor nanocrystals on skin or lung cells and finally extended to animal studies. Using cells has provided us the opportunity to very carefully control our experimental conditions to obtain valid comparisons between treatment and control cells. These types of initial studies are required before moving to more complex biological systems, such as more detailed studies in small animal, and eventually, pre-clinical and clinical tests. On the other hand, longer-term fate studies in a living system, including degradation and clearance, are necessary before full clinical usages of semiconductor nanocrystals become a reality. In addition, previous studies have been done using these types of model systems, allowing us to directly compare our results to results from these studies[27]. These results demonstrate that the surface chemistry of semiconductor nanocrystals is very important for determining toxicity and further open the field for long-term labeling of live cells, and in vivo clinical imaging applications. This should provide guidance for any future improvements upon surface chemistry to reduce or eliminate the toxicity of other nanomaterials as well.

Example 7

Using Nanoonions for Therapeutic Treatment of Cancer in Mammals

This approach is designed to provide maximal drug delivery to cancer cells via a receptor-targeted and internalizing nanoparticle drug carrier that is stable, non-immunogenic, long-lived with extended blood and tissue residence times, and capable of delivering large payloads of diverse classes of drugs. Immunoliposomes (ILs) have been constructed using a modular strategy in which components (mAb fragments, conjugation method, liposome, drugs) were optimized for internalization and intracellular drug delivery (Harding, J. A., Engbers, C. M., Newman, M. S., Goldstein, N. I., and Zalipsky, S. (1997). Immunogenicity and pharmacokinetic attributes of poly(ethylene glycol)-grafted immunoliposomes. *Biochim Biophys Acta* 1327, 181-192).

Immunoliposome Conjugation:

ILs were prepared using small unilamellar liposomes (SUV; 70-100 nm) consisting of disteroyl phosphatidylcholine/cholesterol (DSPC/Chol, 3:2 molar ratio) and polyethylene glycol (PEG2000)-derivatized disteroyl phosphatidylethanolamine (PEG-PE). Anti-HER2 MAb fragments consisted of trastuzumab-Fab', scFv C6.5, scFv F5, or variants; and contained a C-terminal cysteine for covalent conjugation (a-c) or hexahistidine for chelation (d). (a) Ls-MAb linkage: MAb fragments were conjugated to maleimide moieties (M-PE) at the liposome surface. (b) PEG-MAb linkage: MAb fragments were conjugated to maleimide-terminated PEG-PE (M-PEG-PE), resulting in MAb fragments at the distal ends of PEG chains. (c) Micellar Insertion: Preformed liposomes lacking functional sites for conjugation were converted into ILs by insertion of modified MAb fragments. MAb fragments were first coupled to M-PEG-PE, forming micelles for subsequent insertion into liposomes at high efficiency under controlled heating. (d) Ni-NTA Chelation: Phage scFv were shuttled to liposomes by recombinant addition of a C-terminal hexahistidine sequence, then chelation between this sequence and nitrilotriacetic acid-nickel (Ni-NTA) complex anchored to the liposome surface. This enables "instant" ILs by mixing of scFv-containing supernatants with Ni-NTA-containing liposomal probes or drugs to expedite in vitro screens.

Multiwall Carbon Nanoonion Immunoliposomes Preparation: Multiwall carbon nanoonions made as in Example 1 are inserted into the immunoliposomes using any means known in the art which generates a high yield of multiwall carbon nanoonion immunoliposomes. Known methods include passive insertion, sonication and microemulsion or inverse microemulsion, and precipitation. If the subjects will be subject to MRI or other imaging, the multiwall carbon nanoonions are modified and conjugated to the appropriate imaging radionuclide or radiolabel.

Pathophysiologic Effects of Nanomaterials in Healthy Mice:

To assess the pathophysiologic effects of nanomaterials in vivo, toxicity, biodistribution, pharmacokinetic and physiologic studies will be conducted in healthy mice. Since strain background is an important parameter of most disease processes in mice, toxicity, biodistribution and pharmacokinetic studies will be conducted in mouse strains reflecting those strains such as, C57/BLK6, 129/DBA or FVB/n. Parameters that will be obtained include MTD, plasma half-life, volume of distribution, plasma concentrations with respect to time, organ distribution and clearance values. These analyses will be conducted in mice receiving nanomaterials at multiple doses via distinct routes of administration, e.g., intravenous, intraperitoneal, intramuscular, topical, oral and inhaled (where possible).

Once MTD is established for each route of exposure, we will assess pathophysiologic responses to nanomaterials in healthy mice where blood and cerebral spinal fluid (CSF) samples from nanomaterial versus control mice will be compared for indicators of oxidative stress by measuring 8-isoprostane, evidence of inflammation (systemic or localized) by evaluating relative presence of circulating blood cells and activation markers on resident blood cells, and signs of general organ dysfunction. Effects of nanomaterials on hematologic, renal, hepatic and cardiac function will be assessed by submitting blood, urine or CSF for specific clinical chemistry analyses, e.g., alanine aminotransferase, albumin, aspartate aminotransferase, bile acids, bilirubin, sorbitol dehydrogenase and urea nitrogen for hepatic function; alkaline phosphotase, amylase, creatinine, gamma-glutamyltransferase, magnesium and phosphorous for renal function, calcium to assess renal, adrenal and parathyroid dysfunction, electrolytes as a general indicator of renal, adrenal and gastrointestinal and/or metabolic dysfunction and glucose to assess systemic sepsis or pancreatic dysfunction. Other clinical chemistry tests available include serum iron levels, total blood protein levels, complete coagulation panels, urine chemistries, endocrine function markers, complete hematologic services and CSF analyses.

Nanomaterials emerging from Example 1 and intended for large scale use or interofation of living systems will be further assessed for their in vivo effects by toxicogenomics as assessed by mRNA expression of drug metabolism genes (genes within the cytochrome P-450 subfamily), genes that regulate toxicologic events (HSP70 and SODxc) and genes that regulate sugar and lipid metabolism as previously reported (Gerhold, D., Lu, M., Xu, J., Austin, C., Caskey, C. T., and Rushmore, T. (2001). Monitoring expression of genes involved in drug metabolism and toxicology using DNA microarrays. Physiol Genomics 5, 161-170). The rationale for this analysis is that transcriptional changes in gene expression in the liver may provide clues to mechanisms of toxic insult. Such insults may be oxidative, tumor initiating or promoting, or inflammatory for example. Analyses of livers from nanomaterial-exposed animals will be compared to livers of mice exposed to a known xenobiotic, e.g., 3-methylcholanthrene, phenobarbital, dexamethasone or clofibrate. We will isolate total RNA by standard methodology from the livers of control versus treated mice, and subject that RNA to microarray analysis. These analyses will allow us to evaluate complex transcriptional responses to nanomaterials as compared to xenobiotics and subsequently make predictions of their physiological effects in acute versus chronic disease states that will help guide additional analysis of nanomaterials in vivo in concert with results obtained by HR-MAS in collaboration.

To determine pathophysiologic effects of nanomaterials in specific tissues/organs exhibiting profiles of distress/toxicity as determined by systemic oxidative stress and/or clinical chemistry and toxicogenomics, we will evaluate those retaining nanomaterials (as determined by imaging) or tissues/organs exhibiting altered functions over a time-course for parameters such as localized cytotoxicity and cell death, oxidative stress, inflammation, vascular homeostasis, lymphatic homeostasis, IFP and evidence of auto-immunity. The specific order in which these analyses will be conducted will be determined in part by results from clinical chemistry analyses as well as results from in vivo and ex vivo imaging of nanomaterials and general health characteristics of manipulated mice. For example, if blood chemistry or hematology profiles indicate organ/tissue inflammation, 8-isoprostane levels will be examined as a marker of oxidative stress followed by assessment of the nature of inflammation, e.g., tissue retention of nanomaterial, cell death due to localized cytotoxicity, altered vascular homeostasis, ischemia (Miles, A. A., and Miles, E. M. (1952). Vascular reactions to histamine, histamine-liberator and leukotaxine in the skin of guinea pigs. *Journal of Physiology* 118, 228-257) or elevated IFP (Eichten, A. E., Hyun, W. C., and Coussens, L. M. (2005). Characteristics of hematogenous and lymphatic vasculature during de novo epithelial carcinogenesis. Manuscript submitted; Boucher, Y., Brekken, C., Netti, P. A., Baxter, L. T., and Jain, R. K. (1998). Intratumoral infusion of fluid: estimation of hydraulic conductivity and implications for the delivery of therapeutic agents. *Br J Cancer* 78, 1442-1448; Tong, R. T., Boucher, Y., Kozin, S. V., Winkler, F., Hicklin, D. J., and Jain, R. K. (2004). Vascular normalization by vascular endothelial growth factor receptor 2 blockade induces a pressure gradient across the vasculature and improves drug penetration in tumors. *Cancer Res* 64, 3731-3736). These analyses will reveal if inflammation is a primary response in specific tissues where nanomaterials are retained and immunogenic, or secondary to altered vascular homeostasis, and subsequent changes in capillary permeability, impaired clearance by lymphatics and elevated IFP. If capillary permeability is found to be altered, we would assess to what degree lymphatic dysfunction follows as demonstrated by IFP, edema or enlarged lymphatics by lymphatic image analysis and/or MRI (Eichten, A. E., Shen, H.-C. J., and Coussens, L. M. (2005). Three-dimensional visualization of blood and lymphatic vasculature in tissue whole mounts using confocal microscopy. In *Current Protocols in Cytometry*, Volume 12.5, J. P. Robinson, ed. (New Jersey: John Wiley & Sons, Inc.), p. In press.). To determine if inflammation or organ dysfunction may be imparting or underlying a systemic autoimmune process, we will evaluate presence of immunoglobulins in tissue sections collected from multiple organ sites (de Visser, K. E., Korets, L. V., and Coussens, L. M. (2004). Early Neoplastic Progression Is complement Independent. Neoplasia 6, 768-776; de Visser, K. E., Korets, L. V., and Coussens, L. M. (2005). De novo carcinogenesis promoted by chronic inflammation is B lymphocyte dependent. Cancer Cell In press). In combination, these studies will help to establish toxicologic, pharmacokinetic, biodistribution and pathophysiologic properties of nanomaterials in vivo in healthy mice and set the stage for further evaluation in tier 4 studies.

Toxicity:

Nanomaterials will be used in toxicity studies in healthy mice at multiple dosing levels, delivered by various routes, to determine MTD and evidence of induced organ/tissue toxicities. MTD of nanomaterial formulations will be determined in groups of 3 mice per concentration and route of compound to be tested. On the day of the experiment, mice will be randomly grouped and individually marked in appropriately labeled cages. After single exposures, survival, morbidity and body weights will be monitored. Individual body weights will be recorded 3-times/week for 14-days. All animals will be observed for signs of ill health based on body weight, appetite, rough coat, grooming, behavioral changes such as altered gait, lethargy and gross manifestations of stress. Should signs of severe toxicity or illness be observed, animals will be euthanized and necropsy performed to assess other signs of toxicity. Any and all of these findings will be recorded as raw data and the time of death will be logged as the following day.

Biodistribution/Pharmacokinetics:

Mice will receive a single exposure to saline or nanomaterial immunoliposome reconstituted in saline at the MTD. Blood, urine and organs will be collected from saline and nanomaterial treated mice at 5-min, 15-min, 1-, 3-, 6-, 12-, 24- and 48-hrs post injections. Where possible, urine will be collected from mice prior to termination and at other time points. All blood, urine and organs (liver, spleen, lung, heart, kidney and tumor if present) will be flash frozen and stored at −80° C. prior to evaluation where tissue, cells and/or plasma will be tested for total nanomaterial content by HPLC, using a method based on that of Seymour et al, in The pharmacokinetics of polymer-bound adriamycin, Biochem Pharmacol 39, 1125-1131 (1990), hereby incorporated by reference. Time points will contain a minimum of 5 age-matched animals.

In Vivo MRI of Tissue:

Animals subjected to MRI scanning prior to nanomaterial injection and at several times after injection will be performed on a Varian system equipped with a 7.0-Tesla, 18.3-cm horizontal bore magnet (300-MHz proton frequency) inside the MT Zion the barrier at UCSF. For MRI, mice will be anesthetized with sodium pentobarbital (70 mg/kg i.p) and maintained at 37° C. inside the magnet using a heated circulation water blanket, with pelvis motion minimized by a plastic support placed before insertion into a 3-cm diameter quadrature birdcage coil. Multislice images will be acquired using a T1-weighted spin echo sequence (TR/TE=880/13, field of view=30 Å~30 mm using a 128 Å~128 matrix, slice thickness=1.5 mm, and slice separation=1.0 to 1.6 mm). Each set will contain 9-25 slices and enough sets obtained to provide contiguous image data of the tissue. Tissue volume will be measured using the formula $V=4/3[(D1+D2)/4]3$, where D1 and D2 correspond to the longest and shortest (transverse and sagittal) diameter measured from the MRI image. Tissue volumes obtained from final MRIs will be compared with findings from direct anatomical inspection at tissue dissection/necropsy.

Human In Vivo Treatment:

Suspensions of the multi-wall carbon nanoonion immunoliposomes can be prepared by combining the nanoonion immunoliposomes and a buffer or detergent to prepare suspensions in a therapeutic concentration range. The nanoonion immunoliposomes are synthesized as described above, weighed and can be dissolved in low salt buffer through mixing and sonication. Solubilizing and delivery agents can be added to the solution. Dilutions can be made from a stock solution and the final excipient, such as 0.9% NaCl at 37° C., is added to each dose formulation just prior to dosing. The final ratio of liquid components (e.g., buffer, nanoonion immunoliposomes, and saline) can be, for example, 5:5:90, respectively. Subjects having been diagnosed with Erbβ2 cancers where Erbβ2 is detected as expressed ectopically in malignant cells, can be given a therapeutically effective amount of the solution interstitially or intratumorally. A sample dosage may be, for example, 0.1 to 0.5 ml, one to five times/week, using a syringe and a needle.

After sufficient period of nanoonion immunoliposomes administration, a noticeable decrease in the tumor cell growth and cell division should be observed.

While the present sequences, compositions and processes have been described with reference to specific details of certain exemplary embodiments thereof, it is not intended that such details be regarded as limitations upon the scope of the invention. The present examples, methods, procedures, specific compounds and molecules are meant to exemplify and illustrate the invention and should in no way be seen as limiting the scope of the invention. Any patents and publications mentioned in this specification are indicative of levels of those skilled in the art to which the invention pertains and are hereby incorporated by reference to the same extent as if each was specifically and individually incorporated by reference.

TABLE 1

| Gene Category | | P-Value | % Under Expressed | % Over Expressed |
|---|---|---|---|---|
| Carbon nano-onion 0.6 µg/ml | Golgi vesicle transport | 0.0000 | 8.51% | 2.13% |
| | membrane fusion | 0.0002 | 15.79% | 0.00% |
| | secretory pathway | 0.0003 | 4.35% | 1.09% |
| | protein ubiquitination | 0.0139 | 0.68% | 2.05% |
| | intracellular transport | 0.0166 | 1.23% | 0.62% |
| | cell growth and/or maintenance | 0.0201 | 0.66% | 0.27% |
| | fatty acid biosynthesis | 0.0208 | 5.71% | 0.00% |
| | protein metabolism | 0.0323 | 0.71% | 0.29% |
| | ubiquitin cycle | 0.0342 | 0.70% | 1.06% |
| | G1/S transition of mitotic cell cycle | 0.0361 | 4.26% | 0.00% |
| Carbon nano-tube 0.06 µg/ml | Golgi vesicle transport | 0.0007 | 4.26% | 2.13% |
| | protein metabolism | 0.0020 | 0.65% | 0.18% |
| | secretory pathway | 0.0049 | 2.17% | 1.09% |
| | fatty acid biosynthesis | 0.0076 | 5.71% | 0.00% |
| | G1/S transition of mitotic cell cycle | 0.0135 | 4.26% | 0.00% |
| | protein ubiquitination | 0.0174 | 0.68% | 1.37% |
| | mitotic cell cycle | 0.0200 | 1.95% | 0.00% |
| | ubiquitin cycle | 0.0214 | 0.70% | 0.70% |
| | cell homeostasis | 0.0228 | 3.23% | 0.00% |
| | protein prenylation | 0.0262 | 14.29% | 0.00% |
| Carbon nano-onion 6 µg/ml | L-serine metabolism | 0.0000 | 0.00% | 40.00% |
| | tRNA aminoacylation | 0.0000 | 0.00% | 23.81% |
| | amine metabolism | 0.0000 | 0.00% | 5.42% |
| | amine transport | 0.0000 | 0.00% | 12.20% |
| | dicarboxylic acid transport | 0.0020 | 0.00% | 25.00% |
| | response to extracellular stimulus | 0.0063 | 0.00% | 14.29% |
| | heterocycle metabolism | 0.0076 | 0.00% | 6.38% |
| | porphyrin metabolism | 0.0139 | 0.00% | 9.52% |
| | TGF beta receptor signaling pathway | 0.0139 | 4.76% | 4.76% |
| | pigment metabolism | 0.0194 | 0.00% | 8.00% |
| Carbon nano-tube 0.6 µg/ml | tRNA aminoacylation | 0.0000 | 0.00% | 33.33% |
| | L-serine metabolism | 0.0000 | 0.00% | 50.00% |
| | amine metabolism | 0.0000 | 0.00% | 6.90% |
| | amine transport | 0.0000 | 0.00% | 14.63% |
| | response to stimulus | 0.0000 | 0.16% | 2.86% |
| | immune response | 0.0000 | 0.18% | 4.50% |
| | water-soluble vitamin biosynthesis | 0.0024 | 0.00% | 40.00% |
| | inflammatory response | 0.0034 | 0.00% | 5.06% |
| | heterocycle metabolism | 0.0062 | 2.13% | 6.38% |
| | dicarboxylic acid transport | 0.0065 | 0.00% | 25.00% |

TABLE 2

Immune-response genes that over- or under-expressed after treating HSF42 cells with cytotoxic dose (0.6 µg/ml) of multiwall carbon nano-tubes.

| Gene Symbol | Gene Name | Fold Change[a] |
|---|---|---|
| ADAR | adenosine deaminase, RNA-specific | 1.44 |
| BDKRB1 | bradykinin receptor B1 | 1.59 |
| CEBPB | CCAAT/enhancer binding protein (C/EBP), beta | 1.53 |
| CXCL10 | chemokine (C—X—C motif) ligand 10 | 4.82 |
| CXCL3 | chemokine (C—X—C motif) ligand 3 | 2.71 |
| G1P2 | interferon, alpha-inducible protein (clone IFI-15K) | 2.51 |
| G1P3 | interferon, alpha-inducible protein (clone IFI-6-16) | 2.03 |
| IFI44 | interferon-induced protein 44 | 3.50 |
| IFIT1 | interferon-induced protein with tetratricopeptide repeats 1 | 6.99 |
| IFIT2 | interferon-induced protein with tetratricopeptide repeats 2 | 5.99 |
| IFIT3 | interferon-induced protein with tetratricopeptide repeats 3 | 5.85 |
| IFIT5 | interferon-induced protein with tetratricopeptide repeats 5 | 1.76 |
| IRF1 | interferon regulatory factor 1 | 2.02 |
| IRF7 | interferon regulatory factor 7 | 2.47 |
| ISGF3G | interferon-stimulated transcription factor 3, gamma 48 kDa | 1.55 |
| LIF | leukemia inhibitory factor (cholinergic differentiation factor) | 2.67 |
| MGST2 | microsomal glutathione S-transferase 2 | 0.67 |
| MX1 | *Homo sapiens* myxovirus (influenza) resistance 1 | 11.18 |
| MX2 | myxovirus (influenza virus) resistance 2 (mouse) | 6.88 |
| NFE2L1 | nuclear factor (erythroid-derived 2)-like 1 | 1.70 |
| NR4A2 | nuclear receptor subfamily 4, group A, member 2 | 3.26 |
| OAS1 | 2',5'-oligoadenylate synthetase 1, 40/46 kDa | 2.82 |

TABLE 2-continued

Immune-response genes that over- or under-expressed after treating HSF42 cells with cytotoxic dose (0.6 µg/ml) of multiwall carbon nano-tubes.

| Gene Symbol | Gene Name | Fold Change[a] |
| --- | --- | --- |
| OAS2 | 2'-5'-oligoadenylate synthetase 2, 69/71 kDa | 2.79 |
| OAS3 | 2'-5'-oligoadenylate synthetase 3, 100 kDa | 2.21 |
| RIPK2 | receptor-interacting serine-threonine kinase 2 | 1.45 |
| TNFAIP6 | tumor necrosis factor, alpha-induced protein 6 | 1.82 |

[a]Fold changes represent the ratio of mRNA amount of treated samples divided by those of control samples.

TABLE 3

| Gene category | Gene Symbol | Gene Name | Fold change of gene expression for onion 0.6 µg/ml |
| --- | --- | --- | --- |
| Golgi vesicle transport | COPA | coatomer protein complex, subunit alpha | 0.57 |
| | SNAP23 | synaptosomal-associated protein | 0.30 |
| | GBF1 | golgi-specific brefeldin A resistance factor 1 | 2.45 |
| | NAPG | N-ethylmaleimide-sensitive factor attachment protein, gamma | 0.48 |
| | NAPA | N-ethylmaleimide sensitive fusion protein attachment protein alpha | 0.60 |
| membrane fusion | NAPA | N-ethylmaleimide sensitive fusion protein attachment protein alpha | 0.60 |
| | NAPG | N-ethylmaleimide-sensitive factor attachment protein, gamma | 0.48 |
| | SNAP23 | synaptosomal-associated protein | 0.30 |
| secretory pathway | NAPA | N-ethylmaleimide sensitive fusion protein attachment protein alpha | 0.60 |
| | COPA | coatomer protein complex, subunit alpha | 0.57 |
| | GBF1 | golgi-specific brefeldin A resistance factor 1 | 2.45 |
| | NAPG | N-ethylmaleimide-sensitive factor attachment protein, gamma | 0.48 |
| | SCD | stearoyl-CoA desaturase | 0.19 |
| | SNAP23 | synaptosomal-associated protein | 0.30 |
| intracellular transport | GBF1 | golgi-specific brefeldin A resistance factor 1 | 2.45 |
| | DST | dystonin | 0.40 |
| | NAB2 | NGFI-A binding protein 2 | 0.43 |
| | SNAP23 | synaptosomal-associated protein | 0.30 |
| | KDELR3 | KDEL (Lys-Asp-Glu-Leu) endoplasmic reticulum protein retention receptor 3 | 0.76 |
| | NAPG | N-ethylmaleimide-sensitive factor attachment protein, gamma | 0.48 |
| | COPA | coatomer protein complex, subunit alpha | 0.57 |
| | HNRPA1 | heterogeneous nuclear ribonucleoprotein A 1 | 2.49 |
| | NAPA | N-ethylmaleimide sensitive fusion protein attachment protein alpha | 0.60 |
| nucleocytoplasmic transport | NAB2 | NGFI-A binding protein 2 | 0.43 |
| | HNRPA1 | heterogeneous nuclear ribonucleoprotein A 1 | 2.49 |
| | | | Fold change of gene expression for tube 0.06 µg/ml |
| Golgi vesicle transport | COPA | coatomer protein complex, subunit alpha | 0.57 |
| | NAPA | N-ethylmaleimide sensitive fusion protein attachment protein alpha | 0.60 |
| | GBF1 | golgi-specific brefeldin A resistance factor 1 | 2.45 |
| membrane fusion | NAPA | N-ethylmaleimide sensitive fusion protein attachment protein alpha | 0.60 |
| secretory pathway | COPA | coatomer protein complex, subunit alpha | 0.57 |
| | NAPA | N-ethylmaleimide sensitive fusion protein attachment protein alpha | 0.60 |
| | SCD | stearoyl-CoA desaturase | 0.19 |
| | GBF1 | golgi-specific brefeldin A resistance factor 1 | 2.45 |
| intracellular transport | GBF1 | golgi-specific brefeldin A resistance factor 1 | 2.45 |
| | NAPA | N-ethylmaleimide sensitive fusion protein attachment protein alpha | 0.60 |
| | COPA | coatomer protein complex, subunit alpha | 0.57 |

TABLE 4

| Gene category | Gene Symbol | Gene Name | Fold change of gene expression for nano-onion |
|---|---|---|---|
| cell proliferation | EXTL3 | exostoses (multiple)-like 3 | 0.44 |
| | FGFR1 | fibroblast growth factor receptor 1 (fms-related tyrosine kinase 2, Pfeiffer syndrome) | 1.72 |
| | NAB2 | NGFI-A binding protein 2 (EGR1 binding protein 2) | 0.43 |
| cell cycle | DUSP1 | dual specificity phosphatase 1 | 0.17 |
| | TRIM33 | tripartite motif-containing 33 | 1.60 |
| | HSF1 | heat shock transcription factor 1 | 0.52 |
| | BCAT1 | branched chain aminotransferase 1, cytosolic | 0.17 |
| regulation of cell cycle | SKP2 | S-phase kinase-associated protein 2 (p45) | 0.21 |
| | MCL1 | myeloid cell leukemia sequence 1 (BCL2-related) | 0.19 |
| | EGFR | epidermal growth factor receptor (erythroblastic leukemia viral (v-erb-b) oncogene homolog, avian) | 0.24 |
| | MAPK14 | mitogen-activated protein kinase 14 | 0.25 |
| | CRKL | v-crk sarcoma virus CT10 oncogene homolog (avian)-like | 0.20 |
| cell cycle arrest | MACF1 | microtubule-actin crosslinking factor 1 | 1.81 |
| | DST | dystonin | 0.40 |
| cell differentiation | PDLIM7 | PDZ and LIM domain 7 (enigma) | 0.60 |
| | BSG | basigin (OK blood group) | 0.44 |
| | NAPA | N-ethylmaleimide sensitive fusion protein attachment protein alpha | 0.60 |
| | EGR1 | early growth response 1 | 0.39 |
| | | | Fold change of gene expression for nanotube |
| cell proliferation | FGFR1 | fibroblast growth factor receptor 1 (fms-related tyrosine kinase 2, Pfeiffer syndrome) | 1.72 |
| cell cycle | DUSP1 | dual specificity phosphatase 1 | 0.23 |
| | BCAT1 | branched chain aminotransferase 1, cytosolic | 0.24 |
| | CDK2 | cyclin-dependent kinase 2 | 0.58 |
| regulation of cell cycle | SKP2 | S-phase kinase-associated protein 2 (p45) | 0.18 |
| | MCL1 | myeloid cell leukemia sequence 1 (BCL2-related) | 0.18 |
| | MAPK14 | mitogen-activated protein kinase 14 | 0.30 |
| | CRK | v-crk sarcoma virus CT10 oncogene homolog (avian) | 0.53 |
| | SLC12A4 | solute carrier family 12 (potassium/chloride transporters), member 4 | 0.23 |
| cell differentiation | PDLIM7 | PDZ and LIM domain 7 (enigma) | 0.62 |
| | NAPA | N-ethylmaleimide sensitive fusion protein attachment protein alpha | 0.62 |

TABLE 5

| Gene symbol | Gene Name | Fold change of gene expression for 0.6 μg/ml MWCNO |
|---|---|---|
| EGFR | epidermal growth factor receptor (erythroblastic leukemia viral (v-erb-b) oncogene homolog, avian) | 0.17 |
| MCL1 | myeloid cell leukemia sequence 1 (BCL2-related) | 0.19 |
| BCL2L1 | BCL2-like 1 | 0.24 |
| PPM1F | protein phosphatase 1F (PP2C domain containing) | 1.63 |
| TGM2 | transglutaminase 2 (C polypeptide, protein-glutamine-gamma-glutamyltransferase) | 0.35 |
| FGFR1 | fibroblast growth factor receptor 1 (fms-related tyrosine kinase 2, Pfeiffer syndrome) | 1.72 |
| CRKL | v-crk sarcoma virus CT10 oncogene homolog (avian)-like | 0.20 |
| EXTL3 | exostoses (multiple)-like 3 | 0.44 |
| MAPK14 | mitogen-activated protein kinase 14 | 0.31 |
| MACF1 | microtubule-actin crosslinking factor 1 | 1.81 |

TABLE 5-continued

| Gene symbol | Gene Name | Fold change of gene expression for 0.06 μg/ml MWCNT |
|---|---|---|
| TGM2 | transglutaminase 2 (C polypeptide, protein-glutamine-gamma-glutamyltransferase) | 0.40 |
| MCL1 | myeloid cell leukemia sequence 1 (BCL2-related) | 0.18 |
| FGFR1 | fibroblast growth factor receptor 1 (fms-related tyrosine kinase 2, Pfeiffer syndrome) | 1.72 |
| CRK | v-crk sarcoma virus CT10 oncogene homolog (avian) | 0.48 |
| MAPK14 | mitogen-activated protein kinase 14 | 0.30 |
| | | Fold change of gene expression for 6 μg/ml MWCNO |
| YARS | tyrosyl-tRNA synthetase | 1.62 |
| | | Fold change of gene expression for 0.6 μg/ml MWCNT |
| YARS | tyrosyl-tRNA synthetase | 1.75 |
| MX1 | myxovirus (influenza virus) resistance 1, interferon-inducible protein p78 (mouse) | 11.55 |
| BIRC3 | baculoviral IAP repeat-containing 3 | 2.16 |
| RIPK2 | receptor-interacting serine-threonine kinase 2 | 1.38 |
| STAT1 | signal transducer and activator of transcription 1, 91 kDa | 2.22 |
| TNFAIP3 | tumor necrosis factor, alpha-induced protein 3 | 1.95 |
| AHR | aryl hydrocarbon receptor | 1.68 |
| TNFRSF10B | tumor necrosis factor receptor superfamily, member 10b | 1.62 |

TABLE 6

| Gene Category | Gene symbol | Gene Name | MWCNO 6 mg/ml |
|---|---|---|---|
| immune response | EGR1 | early growth response 1 | 0.37 |
| | FOS | v-fos FBJ murine osteosarcoma viral oncogene homolog | 0.14 |
| Stress response | DDIT3 | DNA-damage-inducible transcript 3 | 2.39 |
| | SLC3A2 | solute carrier family 3 (activators of dibasic and neutral amino acid transport), member 2 | 2.46 |
| | STC2 | stanniocalcin 2 | 2.38 |
| | VEGF | vascular endothelial growth factor | 2.18 |
| | DDIT3 | DNA-damage-inducible transcript 3 | 2.39 |
| | FOS | v-fos FBJ murine osteosarcoma viral oncogene homolog | 0.14 |
| | SQSTM1 | sequestosome 1 | 2.00 |
| | VEGF | vascular endothelial growth factor | 2.18 |
| | | | MWCNT 0.6 mg/ml |
| immune response | CXCL10 | chemokine (C—X—C motif) ligand 10 | 4.82 |
| | IFIT2 | interferon-induced protein with tetratricopeptide repeats 2 | 5.99 |
| | IFIT3 | interferon-induced protein with tetratricopeptide repeats 3 | 5.85 |
| | IRF1 | interferon regulatory factor 1 | 2.02 |
| | IRF7 | interferon regulatory factor 7 | 2.47 |
| | CXCL3 | chemokine (C—X—C motif) ligand 3 | 2.71 |
| | MX2 | myxovirus (influenza virus) resistance 2 (mouse) | 6.88 |
| | NR4A2 | nuclear receptor subfamily 4, group A, member 2 | 2.62 |
| | PLSCR1 | phospholipid scramblase 1 | 2.38 |
| response to DNA damage stimulus | DDIT3 | DNA-damage-inducible transcript 3 | 2.70 |
| | IRF7 | interferon regulatory factor 7 | 2.47 |
| Stress response | CXCL10 | chemokine (C—X—C motif) ligand 10 | 4.82 |
| | CXCL3 | chemokine (C—X—C motif) ligand 3 | 2.71 |
| | DDIT3 | DNA-damage-inducible transcript 3 | 2.70 |
| | IRF7 | interferon regulatory factor 7 | 2.47 |
| | MKNK2 | MAP kinase interacting serine/threonine kinase 2 | 2.11 |
| | MX2 | myxovirus (influenza virus) resistance 2 (mouse) | 6.88 |
| | NR4A2 | nuclear receptor subfamily 4, group A, member 2 | 2.62 |
| | OAS1 | 2',5'-oligoadenylate synthetase 1, 40/46 kDa | 2.82 |
| | OAS2 | 2'-5'-oligoadenylate synthetase 2, 69/71 kDa | 2.79 |
| | OAS3 | 2'-5'-oligoadenylate synthetase 3, 100 kDa | 2.21 |

TABLE 6-continued

| Gene Category | Gene symbol | Gene Name | |
|---|---|---|---|
| | PLSCR1 | phospholipid scramblase 1 | 2.38 |
| | SLC3A2 | solute carrier family 3 (activators of dibasic and neutral amino acid transport), member 2 | 2.58 |
| | STAT1 | signal transducer and activator of transcription 1, 91 kDa | 2.22 |
| | VEGF | vascular endothelial growth factor | 2.24 |

TABLE 7

| | | Low Dose (8 nM) | | High Dose (80 nM) | |
|---|---|---|---|---|---|
| | GO category | Number of Genes | List of Genes | Number of Genes | List of Genes |
| Down-regulated | M phase of mitotic cell cycle | 8 | BUB1, CCNA2, CDC20, CDCA3, KIF4A, NEK2, PTTG1 | 2 | BUB1, MPHOSPH1 |
| | Spindle | 5 | BUB1, CDC20, KIF4A, NEK2, TACC3 | 2 | BUB1, MPHOSPH1 |
| | Cytokinesis | 7 | BUB1, CCNA2, CDC20, CDCA3, KIF4A, NEK2, PTTG1 | 1 | BUB1 |
| | Microtubule cytoskeleton | 7 | BUB1, CORIN, KIF2C, KIF4A, CDC20, TACC3, NEK2 | 4 | BUB1, CORIN, FLNB, MPHOSPH1 |
| | Nucleus | 11 | BHLHB2, BUB1, CCNA2, CDC20, CLU, FOXM1, KIF2C, KIF4A, NEK2, PLK1, PSMC3IP, PTTG1 | 4 | BUB1, CLU, H2BB, MPHOSPH1 |
| Up-regulated | Carbohydrate binding | 4 | CHI3L1, GPNMB, PRELP, TNXB | 1 | CHI3L1 |
| | intracellular organelle | 5 | CTSF, CTSH, GPNMB, GSCR2_HUMAN, PTGIS | 1 | H2BB |
| | response to stress | 2 | CLU, FST, MAP2K6 | 1 | CLU |
| | Interphase of mitotic cell cycle | 1 | CCND2 | | |

TABLE 8

| Gene symbol | Gene Name | Fold change of gene expression in log2 |
|---|---|---|
| | 8 nM Qdots | |
| CHI3L1 | chitinase 3-like 1 (cartilage glycoprotein-39) | 4.79653 |
| CLU | clusterin (complement lysis inhibitor, SP-40,40, sulfated glycoprotein 2, testosterone-repressed prostate message 2 | 3.23731 |
| IGFBP2 | insulin-like growth factor binding protein 2, 36 kDa | 2.87535 |
| PTGIS | prostaglandin I2 (prostacyclin) synthase /// prostaglandin I2 (prostacyclin) synthase | 2.63813 |
| CCND2 | cyclin D2 | 2.03349 |
| PRELP | proline arginine-rich end leucine-rich repeat protein | 1.9751 |
| MAP2K6 | mitogen-activated protein kinase kinase 6 | 1.975 |
| TNXB | tenascin XB | 1.93589 |
| FMOD | fibromodulin | 1.72529 |
| FST | follistatin | 1.70054 |
| HCA112 | hepatocellular carcinoma-associated antigen 112 | 1.69136 |
| CTSH | cathepsin H | 1.58153 |
| GPNMB | glycoprotein (transmembrane) nmb | 1.50888 |
| GLTSCR2 | glioma tumor suppressor candidate region gene 2 | 1.31639 |
| CTSF | cathepsin F | 1.23353 |
| PTTG1 | pituitary tumor-transforming 1 | −1.05541 |
| TBPIP | TBP-1 interacting protein | −1.08364 |
| DDA3 | differential display and activated by p53 | −1.15054 |
| TK1 | thymidine kinase 1, soluble | −1.22634 |
| POSTN | periostin, osteoblast specific factor | −1.30694 |

TABLE 8-continued

| Gene symbol | Gene Name | Fold change of gene expression in log2 |
|---|---|---|
| ITGA6 | integrin, alpha 6 | −1.34346 |
| TACC3 | transforming, acidic coiled-coil containing protein 3 | −1.35367 |
| FOXM1 | forkhead box M1 | −1.36322 |
| HCAP-G | chromosome condensation protein G | −1.40545 |
| KIF2C | kinesin family member 2C | −1.48635 |
| NEK2 | NIMA (never in mitosis gene a)-related kinase 2///NIMA (never in mitosis gene a)-related kinase 2 | −1.52081 |
| CDCA3 | cell division cycle associated 3 //// cell division cycle associated 3 | −1.5265 |
| KIF4A | kinesin family member 4A | −1.58766 |
| CDC20 | CDC20 cell division cycle 20 homolog (*S. cerevisiae*) | −1.59272 |
| CCNA2 | cyclin A2 | −1.60045 |
| PLK1 | polo-like kinase 1 (*Drosophila*) | −1.64545 |
| BM039 | uncharacterized bone marrow protein BM039 | −1.66054 |
| SLC4A4 | solute carrier family 4, sodium bicarbonate cotransporter, member 4 | −1.80529 |
| BUB1 | BUB1 budding uninhibited by benzimidazoles 1 homolog (yeast) | −1.81555 |
| SERPINB7 | serine (or cysteine) proteinase inhibitor, clade B (ovalbumin), member 7 | −1.8309 |
| BHLHB2 | basic helix-loop-helix domain containing, class B, 2 | −1.9595 |
| KISS1 | KiSS-1 metastasis-suppressor | −2.45044 |
| CORIN | corin, serine protease | −3.4274 |
| 80 nM QDots | | |
| EGFL6 | EGF-like-domain, multiple 6 | 4.28111 |
| CHI3L1 | chitinase 3-like 1 (cartilage glycoprotein-39) | 4.04108 |
| CLU | clusterin (complement lysis inhibitor, SP-40,40, sulfated glycoprotein 2, testosterone-related kinase 2 | 3.26671 |
| RARRES3 | retinoic acid receptor responder (tazarotene induced) 3 | 2.38346 |
| HIST1H2BD | histone 1, H2bd | 1.73794 |
| MPHOSPH1 | M-phase phosphoprotein 1 | −1.21531 |
| SPHK1 | sphingosine kinase 1 | −1.23641 |
| KLF6 | Kruppel-like factor 6 | −1.62409 |
| FLNB | filamin B, beta (actin binding protein 278) | −1.64077 |
| KLF6 | Kruppel-like factor 6 | −1.6771 |
| BUB1 | BUB1 budding uninhibited by benzimidazoles 1 homolog (yeast) | −1.71227 |
| CORIN | corin, serine protease | −3.41574 |

TABLE 9

Top 20 genes in FIG. 4B Area I

| | | Fold Change of Gene Expression | |
|---|---|---|---|
| Gene Symbol | Gene Name | Onion 0.6 µg/ml | Onion 6 µg/ml |
| KIAA0220 | PI-3-kinase-related kinase SMG-1-like | 3.67 | 1.47 |
| MGC5306 | hypothetical protein MGC5306 | 2.71 | 1.73 |
| ZNF451 | zinc finger protein 451 | 2.64 | 1.36 |
| GBF1 | golgi-specific brefeldin A resistance factor 1 | 2.45 | 1.08 |
| CHD3 | chromodomain helicase DNA binding protein 3 | 2.27 | 1.00 |
| MYST3 | MYST histone acetyltransferase 3 | 2.01 | 1.12 |
| NEBL | nebulette | 1.98 | 1.28 |
| MACF1 | microtubule-actin crosslinking factor 1 | 1.81 | 1.19 |
| KIAA0809 | KIAA0809 protein | 1.81 | 1.05 |
| FGFR1 | fibroblast growth factor receptor 1 | 1.72 | 1.14 |
| SKP2 | S-phase kinase-associated protein 2 (p45) | 0.21 | 0.60 |
| CRKL | v-crk sarcoma virus CT10 oncogene homolog-like | 0.20 | 0.74 |
| SCD | stearoyl-CoA desaturase (delta-9-desaturase) | 0.19 | 0.77 |
| MCL1 | myeloid cell leukemia sequence 1 (BCL2-related) | 0.19 | 1.01 |
| MAPK14 | mitogen-activated protein kinase 14 | 0.18 | 0.89 |
| SKP2 | S-phase kinase-associated protein 2 (p45) | 0.18 | 0.68 |
| TNFRSF10D | tumor necrosis factor receptor superfamily, member 10d | 0.17 | 1.17 |
| EGFR | epidermal growth factor receptor | 0.17 | 0.98 |
| C6orf69 | chromosome 6 open reading frame 69 | 0.16 | 0.82 |
| COPA | coatomer protein complex, subunit alpha | 0.14 | 0.66 |

TABLE 10

Genes in Area II of FIG. 4B. Common genes changed in both the high and low dose treatment with carbon nano-onions.

| Gene Symbol | Gene Name | Fold Change of Gene Expression | |
|---|---|---|---|
| | | Onion 0.6 µg/ml | Onion 6 µg/ml |
| HNRPA1 | heterogeneous nuclear ribonucleoprotein A1 | 2.49 | 2.43 |
| CYorf15B | chromosome Y open reading frame 15B | 1.93 | 1.88 |
| IER2 | immediate early response 2 | 0.66 | 0.55 |
| EGR1 | early growth response 1 | 0.39 | 0.37 |

TABLE 11

Top 20 genes in FIG. 4B Area III

| Gene Symbol | Gene Name | Fold Change of Gene Expression | |
|---|---|---|---|
| | | Onion 0.6 µg/ml | Onion 6 µg/ml |
| SLC7A5 | solute carrier family 7, member 5 | 1.50 | 5.37 |
| TRIB3 | tribbles homolog 3 (*Drosophila*) | 1.14 | 4.01 |
| VLDLR | very low density lipoprotein receptor | 1.09 | 3.26 |
| SLC7A11 | solute carrier family 7, member 11 | 1.46 | 2.95 |
| MGC4504 | hypothetical protein MGC4504 | 1.11 | 2.67 |
| STC2 | stanniocalcin 2 | 1.55 | 2.63 |
| SLC3A2 | solute carrier family 3, member 2 | 0.92 | 2.46 |
| MTHFD2 | methylene tetrahydrofolate dehydrogenase | 1.10 | 2.45 |
| DDIT3 | DNA-damage-inducible transcript 3 | 1.16 | 2.39 |
| PHGDH | phosphoglycerate dehydrogenase | 1.10 | 2.38 |
| TFRC | transferrin receptor (p90, CD71) | 0.89 | 0.60 |
| CSRP2 | cysteine and glycine-rich protein 2 | 1.04 | 0.59 |
| SIM1 | single-minded homolog 1 (*Drosophila*) | 1.12 | 0.58 |
| JUNB | jun B proto-oncogene | 0.71 | 0.56 |
| JMJD2B | jumonji domain containing 2B | 0.97 | 0.56 |
| ALG12 | asparagine-linked glycosylation 12 homolog | 0.86 | 0.55 |
| P2RY5 | purinergic receptor P2Y, G-protein coupled, 5 | 0.96 | 0.54 |
| CSRP2 | cysteine and glycine-rich protein 2 | 0.90 | 0.54 |
| RGS4 | regulator of G-protein signalling 4 | 0.82 | 0.45 |
| C10orf10 | chromosome 10 open reading frame 10 | 0.88 | 0.42 |

TABLE 12

Top 20 genes in FIG. 4C Area I

| Gene Symbol | Gene Name | Fold Change of Gene Expression | |
|---|---|---|---|
| | | Tube 0.06 µg/ml | Tube 0.6 µg/ml |
| GBF1 | golgi-specific brefeldin A resistance factor 1 | 2.54 | 1.14 |
| MSF | MLL septin-like fusion | 2.35 | 1.21 |
| CHD3 | chromodomain helicase DNA binding protein 3 | 2.20 | 1.19 |
| MYST3 | MYST histone acetyltransferase 3 | 2.10 | 1.30 |
| DULLARD | dullard homolog (*Xenopus laevis*) | 1.77 | 1.12 |
| FGFR1 | fibroblast growth factor receptor 1 | 1.72 | 1.20 |
| KIAA0809 | KIAA0809 protein | 1.72 | 1.28 |
| hspc193 | SMAD, mothers against DPP homolog 3 | 1.61 | 1.08 |
| PCDHGB1 | protocadherin gamma subfamily B, 1 | 1.60 | 1.14 |
| MPZL1 | myelin protein zero-like 1 | 0.34 | 0.72 |
| LANCL1 | LanC lantibiotic synthetase component C-like 1 | 0.32 | 0.75 |
| SPTBN1 | spectrin, beta, non-erythrocytic 1 | 0.32 | 0.73 |
| MAPK14 | mitogen-activated protein kinase 14 | 0.30 | 0.77 |
| MBTPS2 | membrane-bound transcription factor protease, site 2 | 0.29 | 0.73 |
| CDK2 | *Homo sapiens* mRNA for d-HSCDK2, complete cds. | 0.28 | 0.65 |
| BCAT1 | branched chain aminotransferase 1, cytosolic | 0.27 | 1.03 |
| LOXL2 | lysyl oxidase-like 2 | 0.23 | 0.58 |
| BCAT1 | branched chain aminotransferase 1, cytosolic | 0.22 | 0.92 |
| SCD | stearoyl-CoA desaturase (delta-9-desaturase) | 0.21 | 0.60 |
| MCL1 | myeloid cell leukemia sequence 1 (BCL2-related) | 0.18 | 0.77 |

TABLE 13

Genes in FIG. 4C, Area II.

| Gene Symbol | Gene Name | Fold Change of Gene Expression | |
|---|---|---|---|
| | | Tube 0.06 µg/ml | Tube 0.6 µg/ml |
| OSGEPL1 | O-sialoglycoprotein endopeptidase-like 1 | 0.69 | 0.70 |
| C11orf17 | chromosome 11 open reading frame 17 | 0.66 | 0.64 |
| C21orf4 | chromosome 21 open reading frame 4 | 0.63 | 0.62 |

TABLE 14

Top 20 genes in FIG. 4C Area III

| Gene Symbol | Gene Name | Fold Change of Gene Expression | |
|---|---|---|---|
| | | Tube 0.06 μg/ml | Tube 0.6 μg/ml |
| DDIT4 | DNA-damage-inducible transcript 4 | 1.07 | 7.89 |
| MX2 | myxovirus (influenza virus) resistance 2 (mouse) | 1.14 | 6.88 |
| SLC7A5 | solute carrier family 7, member 5 | 1.12 | 6.43 |
| ASNS | asparagine synthetase | 0.94 | 6.13 |
| IFIT2 | interferon-induced protein with tetratricopeptide repeats 2 | 0.54 | 5.99 |
| TRIB3 | tribbles homolog 3 (*Drosophila*) | 1.01 | 5.93 |
| IFIT3 | interferon-induced protein with tetratricopeptide repeats 3 | 1.19 | 5.85 |
| CXCL10 | chemokine (C—X—C motif) ligand 10 | 1.00 | 4.82 |
| INHBE | inhibin, beta E | 1.07 | 4.78 |
| PCK2 | phosphoenolpyruvate carboxykinase 2 (mitochondrial) | 1.29 | 4.72 |
| SKP2 | S-phase kinase-associated protein 2 (p45) | 1.19 | 0.65 |
| CALR | calreticulin | 0.85 | 0.65 |
| HIG2 | hypoxia-inducible protein 2 | 1.14 | 0.64 |
| NIPSNAP1 | nipsnap homolog 1 (*C. elegans*) | 0.83 | 0.64 |
| FLJ22624 | FLJ22624 protein | 0.89 | 0.60 |
| ALG12 | asparagine-linked glycosylation 12 homolog | 0.81 | 0.56 |
| FKBP14 | FK506 binding protein 14, 22 kDa | 0.71 | 0.54 |
| SLC38A4 | solute carrier family 38, member 4 | 1.20 | 0.51 |
| RGS4 | regulator of G-protein signalling 4 | 0.97 | 0.49 |
| DPYSL2 | dihydropyrimidinase-like 2 | 0.83 | 0.48 |

TABLE 15

Top 20 genes in FIG. 4D Area I

| Gene Symbol | Gene Name | Fold Change of Gene Expression | |
|---|---|---|---|
| | | Onion 0.6 μg/ml | Tube 0.06 μg/ml |
| DKFZp547E087 | PI-3-kinase-related kinase SMG-1-like | 3.67 | 2.89 |
| MGC5306 | hypothetical protein MGC5306 | 2.71 | 1.62 |
| ZNF451 | zinc finger protein 451 | 2.64 | 1.94 |
| HNRPA1 | heterogeneous nuclear ribonucleoprotein A1 | 2.49 | 1.68 |
| NEBL | nebulette | 1.98 | 1.31 |
| CYorf15B | chromosome Y open reading frame 15B | 1.93 | 1.38 |
| MACF1 | microtubule-actin crosslinking factor 1 | 1.81 | 1.38 |
| PPM1F | protein phosphatase 1F (PP2C domain containing) | 1.63 | 1.49 |
| TRIM33 | tripartite motif-containing 33 | 1.60 | 1.52 |
| DNMBP | dynamin binding protein | 1.52 | 1.44 |
| SNAP23 | synaptosomal-associated protein, 23 kDa | 0.30 | 0.33 |
| PLEC1 | plectin 1, intermediate filament binding protein 500 kDa | 0.27 | 0.33 |
| GNS | glucosamine (N-acetyl)-6-sulfatase | 0.26 | 0.29 |
| BCL2L1 | BCL2-like 1 | 0.24 | 0.30 |
| SKP2 | S-phase kinase-associated protein 2 (p45) | 0.21 | 0.25 |
| CRKL | v-crk sarcoma virus CT10 oncogene homolog (avian)-like | 0.20 | 0.28 |
| MAPK14 | mitogen-activated protein kinase 14 | 0.18 | 0.22 |
| TNFRSF10D | tumor necrosis factor receptor superfamily, member 10d | 0.17 | 0.18 |
| EGFR | epidermal growth factor receptor oncogene homolog | 0.17 | 0.21 |
| C6orf69 | chromosome 6 open reading frame 69 | 0.16 | 0.20 |

TABLE 16

Top 20 genes in FIG. 4D, Area II.

| Gene Symbol | Gene Name | Fold Change of Gene Expression | |
|---|---|---|---|
| | | Onion 0.6 μg/ml | Tube 0.06 μg/ml |
| GBF1 | golgi-specific brefeldin A resistance factor 1 | 2.45 | 2.54 |
| CHD3 | chromodomain helicase DNA binding protein 3 | 2.27 | 2.20 |
| MYST3 | MYST histone acetyltransferase (monocytic leukemia) 3 | 2.01 | 2.10 |
| KIAA0809 | KIAA0809 protein | 1.81 | 1.72 |
| FGFR1 | fibroblast growth factor receptor 1 | 1.72 | 1.72 |

TABLE 16-continued

Top 20 genes in FIG. 4D, Area II.

| Gene Symbol | Gene Name | Fold Change of Gene Expression | |
| --- | --- | --- | --- |
| | | Onion 0.6 µg/ml | Tube 0.06 µg/ml |
| SPTBN1 | spectrin, beta, non-erythrocytic 1 | 0.35 | 0.32 |
| PRKAB1 | protein kinase, AMP-activated, beta 1 non-catalytic subunit | 0.35 | 0.35 |
| MPZL1 | myelin protein zero-like 1 | 0.34 | 0.34 |
| LANCL1 | LanC lantibiotic synthetase component C-like 1 (bacterial) | 0.33 | 0.32 |
| MAPK14 | mitogen-activated protein kinase 14 | 0.31 | 0.30 |
| FNTB | farnesyltransferase, CAAX box, beta | 0.31 | 0.33 |
| VARS2 | valyl-tRNA synthetase 2 | 0.30 | 0.38 |
| MBTPS2 | membrane-bound transcription factor protease, site 2 | 0.27 | 0.29 |
| BCAT1 | branched chain aminotransferase 1, cytosolic | 0.24 | 0.22 |
| LOXL2 | lysyl oxidase-like 2 | 0.23 | 0.23 |
| COL3A1 | collagen, type III, alpha 1 | 0.22 | 0.22 |
| SCD | stearoyl-CoA desaturase (delta-9-desaturase) | 0.19 | 0.21 |
| MCL1 | myeloid cell leukemia sequence 1 (BCL2-related) | 0.19 | 0.18 |
| SKP2 | S-phase kinase-associated protein 2 (p45) | 0.18 | 0.18 |
| COPA | coatomer protein complex, subunit alpha | 0.14 | 0.15 |

TABLE 17

Top 20 genes in FIG. 4D Area III.

| Gene Symbol | Gene Name | Fold Change of Gene Expression | |
| --- | --- | --- | --- |
| | | Onion 0.6 µg/ml | Tube 0.06 µg/ml |
| MSF | MLL septin-like fusion | 2.21 | 2.35 |
| DULLARD | dullard homolog (*Xenopus laevis*) | 1.66 | 1.77 |
| hspc193 | SMAD, mothers against DPP homolog 3 (*Drosophila*) | 1.58 | 1.61 |
| PCDHGB1 | protocadherin gamma subfamily B, 1 | 1.55 | 1.60 |
| CDK2 | *Homo sapiens* mRNA for d-HSCDK2, complete cds. | 0.86 | 0.89 |
| OSGEPL1 | O-sialoglycoprotein endopeptidase-like 1 | 0.71 | 0.69 |
| C21orf4 | chromosome 21 open reading frame 4 | 0.67 | 0.63 |
| CRK | *Homo sapiens* v-crk avian sarcoma virus CT10 oncogene homolog | 0.53 | 0.48 |
| CDK2 | *Homo sapiens* mRNA for d-HSCDK2, complete cds. | 0.32 | 0.28 |
| BCAT1 | branched chain aminotransferase 1, cytosolic | 0.30 | 0.27 |
| SLC12A4 | solute carrier family 12, member 4 | 0.25 | 0.23 |
| LOX | | 0.19 | 0.18 |

TABLE 18

Top 20 genes in FIG. 4E Area I.

| Gene Symbol | Gene Name | Fold Change of Gene Expression | |
| --- | --- | --- | --- |
| | | Onion 0.6 µg/ml | Tube 0.06 µg/ml |
| STC2 | stanniocalcin 2 | 2.13 | 1.80 |
| SFRS7 | splicing factor, arginine/serine-rich 7, 35 kDa | 1.95 | 1.56 |
| CYorf15B | chromosome Y open reading frame 15B | 1.88 | 1.39 |
| OGT | O-linked N-acetylglucosamine (GlcNAc) transferase | 1.82 | 1.54 |
| HK2 | hexokinase 2 | 1.78 | 1.62 |
| WARS | tryptophanyl-tRNA synthetase | 1.73 | 1.65 |
| KIAA0469 | KIAA0469 gene product | 1.66 | 1.42 |
| MT1K | metallothionein 1K | 1.61 | 1.36 |
| TXNRD1 | thioredoxin reductase 1 | 1.61 | 1.34 |
| TIPARP | TCDD-inducible poly(ADP-ribose) polymerase | 1.58 | 1.11 |
| TFRC | transferrin receptor (p90, CD71) | 0.60 | 1.14 |
| TFRC | transferrin receptor (p90, CD71) | 0.60 | 1.05 |
| SIM1 | single-minded homolog 1 (*Drosophila*) | 0.58 | 0.73 |
| JUNB | jun B proto-oncogene | 0.56 | 0.88 |
| JMJD2B | jumonji domain containing 2B | 0.56 | 0.60 |
| IER2 | immediate early response 2 | 0.55 | 0.87 |

TABLE 18-continued

Top 20 genes in FIG. 4E Area I.

| | | Fold Change of Gene Expression | |
|---|---|---|---|
| Gene Symbol | Gene Name | Onion 0.6 μg/ml | Tube 0.06 μg/ml |
| P2RY5 | purinergic receptor P2Y, G-protein coupled, 5 | 0.54 | 0.64 |
| EGR1 | early growth response 1 | 0.46 | 1.12 |
| EGR1 | early growth response 1 | 0.27 | 0.67 |
| FOS | v-fos FBJ murine osteosarcoma viral oncogene homolog | 0.14 | 0.31 |

TABLE 19

Top 20 genes in FIG. 4E Area II.

| | | Fold Change of Gene Expression | |
|---|---|---|---|
| Gene Symbol | Gene Name | Onion 6 μg/ml | Tube 0.6 μg/ml |
| DDIT4 | DNA-damage-inducible transcript 4 | 6.05 | 7.89 |
| SLC7A5 | solute carrier family 7, member 5 | 5.37 | 6.43 |
| PSAT1 | phosphoserine aminotransferase 1 | 5.10 | 5.67 |
| ASNS | asparagine synthetase | 4.55 | 6.13 |
| TRIB3 | tribbles homolog 3 (*Drosophila*) | 4.01 | 5.93 |
| PCK2 | phosphoenolpyruvate carboxykinase 2 (mitochondrial) | 3.35 | 4.72 |
| VLDLR | very low density lipoprotein receptor | 3.26 | 4.50 |
| SLC7A11 | solute carrier family 7, member 11 | 2.95 | 3.36 |
| MGC4504 | hypothetical protein MGC4504 | 2.67 | 3.79 |
| STC2 | stanniocalcin 2 | 2.63 | 2.29 |
| MGST2 | microsomal glutathione S-transferase 2 | 0.67 | 0.67 |
| DPYSL2 | dihydropyrimidinase-like 2 | 0.64 | 0.48 |
| CDKN2C | cyclin-dependent kinase inhibitor 2C (p18) | 0.60 | 0.54 |
| CSRP2 | cysteine and glycine-rich protein 2 | 0.59 | 0.60 |
| ALG12 | asparagine-linked glycosylation 12 homolog | 0.55 | 0.56 |
| THRAP5 | thyroid hormone receptor associated protein 5 | 0.55 | 0.56 |
| CSRP2 | cysteine and glycine-rich protein 2 | 0.54 | 0.52 |
| SLC38A4 | solute carrier family 38, member 4 | 0.52 | 0.51 |
| RGS4 | regulator of G-protein signalling 4 | 0.45 | 0.49 |
| C10orf10 | chromosome 10 open reading frame 10 | 0.42 | 0.45 |

TABLE 20

Top 20 genes in FIG. 4E Area III

| | | Fold Change of Gene Expression | |
|---|---|---|---|
| Gene Symbol | Gene Name | Onion high dose (6 μg/ml) | Tube high dose (0.6 μg/ml) |
| MX2 | myxovirus (influenza virus) resistance 2 (mouse) | 1.60 | 6.88 |
| IFIT2 | interferon-induced protein with tetratricopeptide repeats 2 | 1.68 | 5.99 |
| CXCL10 | chemokine (C—X—C motif) ligand 10 | 1.34 | 4.82 |
| INHBE | inhibin, beta E | 1.82 | 4.78 |
| C1orf29 | chromosome 1 open reading frame 29 | 1.12 | 4.60 |
| NR4A2 | nuclear receptor subfamily 4, group A, member 2 | 1.19 | 4.53 |
| HERC5 | hect domain and RLD 5 | 1.37 | 4.46 |
| IFI44 | interferon-induced protein 44 | 1.35 | 4.34 |
| DDX58 | DEAD (Asp-Glu-Ala-Asp) box polypeptide 58 | 1.38 | 3.63 |
| KIAA1718 | KIAA1718 protein | 2.36 | 3.54 |
| HERC6 | hect domain and RLD 6 | 1.29 | 3.53 |
| OAS2 | 2'-5'-oligoadenylate synthetase 2, 69/71 kDa | 1.20 | 3.49 |
| ZC3HDC1 | zinc finger CCCH type domain containing 1 | 1.66 | 3.36 |
| OAS1 | 2',5'-oligoadenylate synthetase 1, 40/46 kDa | 1.19 | 3.31 |
| NR4A2 | nuclear receptor subfamily 4, group A, member 2 | 1.06 | 2.88 |
| IFI44 | interferon-induced protein 44 | 0.92 | 2.65 |
| PLSCR1 | phospholipid scramblase 1 | 1.32 | 2.49 |
| IRF7 | interferon regulatory factor 7 | 1.07 | 2.47 |
| NR4A2 | nuclear receptor subfamily 4, group A, member 2 | 1.04 | 2.36 |
| OAS1 | 2',5'-oligoadenylate synthetase 1, 40/46 kDa | 1.31 | 2.33 |

TABLE 21

Genes changed by onion but fall in the category of protein ubiquitination and ubiquitin cycle.

| Gene Category | Gene symbol | Gene Name | Fold change of gene expression MWCNO 0.6 µg/ml |
|---|---|---|---|
| Ubiquitination | CHD3 | chromodomain helicase DNA binding protein 3 | 2.27 |
| | MYST3 | MYST histone acetyltransferase (monocytic leukemia) | 2.01 |
| | SKP2 | S-phase kinase-associated protein 2 (p45) | 0.21 |
| | TGM2 | transglutaminase 2 (C polypeptide, protein-glutamine-gamma-glutamyltransferase) | 0.35 |
| | TRIM33 | tripartite motif-containing 33 | 1.60 |

| Gene Category | Gene symbol | Gene Name | Fold change of gene expression MWCNT 0.06 µg/ml |
|---|---|---|---|
| Ubiquitination | TGM2 | transglutaminase 2 (C polypeptide, protein-glutamine-gamma-glutamyltransferase) | 0.40 |
| | MYST3 | MYST histone acetyltransferase (monocytic leukemia) | 2.10 |
| | SKP2 | S-phase kinase-associated protein 2 (p45) | 0.18 |
| | CHD3 | chromodomain helicase DNA binding protein 3 | 2.20 |

What is claimed is:

1. A composition, comprising: a multiwall carbon nanoonion having a diameter from 10-50 nm, wherein said nanoonion is conjugated to a tumor-targeting antibody and a magnetic resonance imaging reagent, further comprising an immunoliposome bound to or encapsulating the multiwall carbon nanoonion wherein said immunoliposome comprises a lipid comprised of phosphatidylethanolamine and/or phosphatidylcholine.

2. The composition of claim 1 wherein the multiwall carbon nanoonion has a diameter of about 30 nm.

3. The composition of claim 1 wherein the tumor-targeting antibody is a monoclonal antibody.

4. The composition of claim 3 wherein the monoclonal antibody is specific for Erbβ2.

5. The composition of claim 1 wherein the magnetic resonance imaging reagent is Gd-DPTA, $^{19}F$, $^{1}H$, or $^{125}I$.

6. The composition of claim 1, wherein the immunoliposomes comprise disteroyl phosphatidylcholine/cholesterol (DSPC/Chol, 3:2 molar ratio) and PEG2000-derivatized disteroyl phosphatidylehtanolamine (PEG-PE), and wherein the tumor-targeting antibody comprises anti-HER2 MAb fragments.

7. A method of treating cancer comprising delivering the composition of claim 1 to a subject in an effective therapeutic amount.

8. The method of claim 7, wherein the effective therapeutic amount does not induce greater than 25% overexpression or underexpression of a gene following treatment.

* * * * *